United States Patent
Davidson et al.

(10) Patent No.: US 10,059,987 B2
(45) Date of Patent: *Aug. 28, 2018

(54) MODIFIED PROTEINS AND METHODS OF MAKING AND USING SAME

(71) Applicant: Life Technologies Corporation, Carlsbad, CA (US)

(72) Inventors: John Davidson, Guilford, CT (US); Wolfgang Hinz, Killingworth, CT (US); Jonathan Rothberg, Guilford, CT (US); Richard Whitaker, Lynnfield, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,800

(22) Filed: Jun. 16, 2017

(65) Prior Publication Data

US 2017/0292156 A1    Oct. 12, 2017

Related U.S. Application Data

(60) Division of application No. 14/724,354, filed on May 28, 2015, now Pat. No. 9,714,915, which is a continuation of application No. 13/036,623, filed on Feb. 28, 2011, now abandoned, which is a continuation-in-part of application No. 13/035,177, filed on Feb. 25, 2011, now abandoned.

(60) Provisional application No. 61/308,863, filed on Feb. 26, 2010.

(51) Int. Cl.
*C12N 9/12* (2006.01)
*C12Q 1/6869* (2018.01)
*G01N 27/414* (2006.01)

(52) U.S. Cl.
CPC ......... *C12Q 1/6869* (2013.01); *C12N 9/1252* (2013.01); *C12Y 207/07007* (2013.01); *G01N 27/4145* (2013.01)

(58) Field of Classification Search
None
See application file for complete search history.

(56) References Cited

U.S. PATENT DOCUMENTS

| | | | |
|---|---|---|---|
| 5,576,204 A | 11/1996 | Blanco et al. | |
| 6,013,451 A | 1/2000 | Wong et al. | |
| 6,485,909 B1 | 11/2002 | Hong et al. | |
| 7,972,828 B2 | 7/2011 | Ward et al. | |
| 8,114,591 B2 | 2/2012 | Toumazou et al. | |
| 9,714,915 B2 | 7/2017 | Davidson et al. | |
| 2003/0138834 A1 | 7/2003 | Dawson | |
| 2006/0035360 A1 | 2/2006 | Farchaus, III | |
| 2006/0199214 A1 | 9/2006 | Jack et al. | |
| 2006/0240439 A1 | 10/2006 | Smith et al. | |
| 2008/0108082 A1 | 5/2008 | Rank et al. | |
| 2008/0166727 A1 | 7/2008 | Esfandyarpour et al. | |
| 2009/0026082 A1 | 1/2009 | Rothberg et al. | |
| 2011/0165652 A1 | 7/2011 | Hardin et al. | |
| 2011/0262903 A1 | 10/2011 | Davidson et al. | |
| 2011/0318748 A1 | 12/2011 | Davidson et al. | |
| 2012/0202276 A1 | 8/2012 | Davidson et al. | |

FOREIGN PATENT DOCUMENTS

| | | |
|---|---|---|
| GB | 2461128 | 12/2009 |
| JP | 4193997 | 12/2008 |
| WO | 1994/016107 | 7/1994 |
| WO | 2007/076057 | 7/2007 |
| WO | 2008/076406 | 6/2008 |
| WO | 2010/111674 | 9/2010 |
| WO | 2011/106629 | 9/2011 |
| WO | 2011/106634 | 9/2011 |
| WO | 2011/106766 | 9/2011 |
| WO | 2011/106770 | 9/2011 |

OTHER PUBLICATIONS

Anderson et al., "A system for multiplexed direct electrical detection of DNA synthesis", *Sensors and Actuators B Chem.*, vol. 129, 2008, 79-86.

Anderson et al., "Incorporation of reporter-labeled nucleotides by DNA polymerases", *BioTechniques*, vol. 38, No. 2, 2005, 257-264.

AU2011220536, Search Information Statement (SIS) completion, May 10, 2012.

EP11748135.8, Extended European Search Report, dated Feb. 7, 2013, 1-7.

EP11748228.1, Extended European Search Report, dated Feb. 13, 2013, 1-7.

EP14179490, European Search Report, dated Oct. 30, 2014,1-4.

EP15192848, , Extended European Search Report, dated Jun. 8, 2016, 1-9.

Ishino et al., "English Translation of JP 4193997 B1", Abstract and Claims only, 1-3.

Kim et al., "Enhancing thermostability of *Escherichia coli* phytase AppA2 by error-prone PCR", *Appl. Microbiol. Biotechnol.*, vol. 79, 2008, 69-75.

Lohet al., "Highly Tolerated Amino Acid Substitutions Increase the Fidelity of *Escherichia coli* DNA Polymerase I", *The Journal of Biological Chemistry*, vol. 282, No. 16, Apr. 2007, 12201-12209.

Olthuis et al., "Characterization of proteins by means of their buffer capacity, measured with an ISFET-based coulometric sensor-actuator system", *Biosensors & Bioelectronics*, vol. 9, No. 9-10, 1994, 743-751.

(Continued)

*Primary Examiner* — Richard G Hutson
(74) *Attorney, Agent, or Firm* — Life Technologies Corporation; Karen Zachow

(57) ABSTRACT

Methods, compositions, systems, apparatuses and kits comprising modified proteins, particularly modified nucleic acid-binding proteins with altered buffering properties are provided. For example, in some embodiments, methods of forming modified proteins including one or more amino acid modifications to achieve desired pKa values are described. Furthermore, the invention provides methods for using such modified proteins in ion-producing reactions, such as ion-based nucleic acid sequencing reactions.

20 Claims, 6 Drawing Sheets

Specification includes a Sequence Listing.

(56) References Cited

OTHER PUBLICATIONS

Pace et al., "Protein Ionizable Groups: pK Values and Their Contribution to Protein Stability and Solubility", *Journal of Biological Chemistry*, vol. 284, No. 20, May 15, 2009, 13285-13289.
PCT/US2011/026228, International Search Report and Written Opinion, dated Feb. 22, 2012.
PCT/US2011/026450, International Search Report and Written Opinion, dated Feb. 22, 2012.
PCT/US2011026219, International Search Report and Written Opinion, dated Nov. 28, 2011.
Pourmand et al., "Direct electrical detection of DNA synthesis", *PNAS*, vol. 103(17), 2006, 6466-6470.
Purushothaman et al., "Towards Fast Solid State DNA Sequencing", *IEEE ISCAS 2002 Proceedings*, Circuits and Systems, vol. 4, 2002, pp. IV-169-IV-172.
Riggs et al., "Construction of single amino acid substitution mutants of cloned Bacillus stearothermophilus DNA polymerase I which lack 5'-3' exonuclease activity", *Biochimica et Biophysica Acta*, vol. 1307, 1996, 178-186.
Sakata et al., "DNA Sequencing Based on Intrinsic Molecular Charges", *Angewandte Chemie International Edition 2006*, vol. 118, 2006, 2283-2286.
Sakurai et al., "Real-Time Monitoring of DNA Polymerase Reactions by a Micro ISFET pH Sensor", *Anal Chem*, vol. 64(17), 1992, pp. 1996-1997.
Zhang et al., "Mutagenic nucleotide incorporation and hindered translocation by a food carcinogen C8-dG adduct in Sulfolobus solfataricus P2 DNA polymerase IV (Dpo4): modeling and dynamics studies", *Nucleic Acids Research*, vol. 34, No. 11, 2006, 3326-3337.

MAKMAFTLAD RVTEEMLADK AALVVEVVEE NYHDAPIVGI 40
AVVNEHGRFF LRPETALADP QFVAWLGDET KKKSMFDSKR 80
AAVALKWKGI ELCGVSFDLL LAAYLLDPAQ GVDDVAAAAK 120
MKQYEAVRPD EAVYGKGAKR AVPDEPVLAE HLVRKAAAIW 160
ELERPFLDEL RRNEQDRLLV ELEQPLSSIL AEMEFAGVKV 200
DTKRLEQMGK ELAEQLGTVE QRIYELAGQE FNINSPKQLG 240
VILFEKLQLP VLKKKTKTGYS TSADVLEKLA PYHEIVENIL 280
HYRQLGKLQS TYIEGLLKVV RPDTKKVHTI FNQALTQTGR 320
LSSTEPNLQN IPIRLEEGRK IRQAFVPSES DWLIFAADYS 360
QIELRVLAHI AEDDNLMEAF RRDLDIHTKT AMDIFQVSED 400
EVTPNMRRQA KAVNFGIVYG ISDYGLAQNL NISRKEAAEF 440
IERYFESFPG VKRYMENIVQ EAKQKGYVTT LLHRRRYLPD 480
ITSRNFNVRS FAERMAMNTP IQGSAADIIK KAMIDLNARL 520
KEERLQAHLL LQVHDELILE APKEEMERLC RLVPEVMEQA 560
VTLRVPLKVD YHYGSTWYDA K SEQ ID NO: 1

```
b103   ---MPRKMFSCDFETTTKLDDCRVWAYGYMEIGNLDNYKIGNSLDEFMQWVMEIQADLYF  57
phi29  MKHMPRKMYSCAFETTTKVEDCRVWAYGYMNIEDHSEYKIGNSLDEFMAWVLKVQADLYF  60
          *: ***.:****** * :::**** b103   HNLKFDGAFIVWWLEHHGFKWSNEGLPNTYNTIISKMGQWYMIDIEFGYKGKRKIHTVIY  117
phi29  HNLKFAGAFIINWLERNGFKWSADGLPNTYNTIISRMGQWYMIDICLGYKGKRKIHTVIY  120
       ***.:* :***:.*********:***** *********** b103   DSLKKLPFVKKIAKDFQLPLLKGDIDYHAERPVGHEITPEEYEVIKNDIEIIARALDIQ  177
phi29  DSLKKLPFVKKIAKDFKLTVLKGDIDYHKERPVGYKITPEEYAYIKNDIQIIAEALLIQ  180
       ****************:*.:*****:*::.* **:* b103   FKQGLDRMTAGSDSLKGFKDILSTKKFNKVFPKLSLPMDKEIRRAYRGGFTWLNDKYKEK  237
phi29  FKQGLDRMTAGSDSLKGFKDIITKKFKKVFPTLSLGLDKEVRYAYRGGFTWLNDRFKEK  240
       ******************:::: *  : *******:: * b103   EIGEGMVFDVNSLYPSQMYSRPLPYGAPIVFQGKYEKDEQYPLYIQRIRFEFELKEGYIP  297
phi29  EIGEGMVFDVNSLYPAQMYSRLLPYGEPIVFEGKYVWDEDYPLHIQHIRCEFELKEGYIP  300
       *************:*     :*:: ********** b103   TIQIKKNPFFKGMEYLKNSGAEPVELYLTNVDLELIQEHYEMYNVEYIDGFKFREKTGLF  357
phi29  TIQIKRSRFYKGMEYLKSSGGEIADLWLSNVDLELMKEHYDLYNVEYISGLKFKATTGLF  360
       ***:. :*****.:*.*: *: *:** .: **.*:* ::* b103   KEFIDKWTYVKTHEKGAKKQLAKLMFDSLYGKFASNPDVTGKVPYLKEDGSLGFRVGDEE  417
phi29  KDFIDKWTYIKTTSEGAIKQLAKLMLNSLYGKFASNPDVTGKVPYLKENGALGFRLGEEE  420
       *:*******:**. :**:*******:. *******************:*. ****:*:**

b103   YKDPVYTPMGVFITAWARFTTTIAAQACYDRIIYCDTDSIHLTGTEVPELIKDIVDPKKL  477
phi29  TKDPVYTPMGVFITAWARYTTTIAAQACYDRIIYCDTDSIHLTGTEIPDVIKDIVDPKKL  480
       .***************:**************************:..******* b103   GYWAHESTFKRAKYLRQKTYIQDIYAKEVDGKLIECSPDEATTTKFSVKCAGMTDTIKKK  537
phi29  GYWAHESTFKRAKYLRQKTYIQDIYMKEVDGKLVEGSPDDYTDIKFSVKCAGMTDKIKKE  540
       *************************  ***** :.*  : *  *********** ***:

b103   VTFDNFRVGFSSTGKPKPVQVNGGVVLVDSVFTIK  572
phi29  VTFENFKVGFSRKMKPKPVQVPGGVVLVDDTFTIK  575
       ***::**:*** . ******.*******: ****
```

| Run No | Bead wells | live beads | Library Keypass | 50Q17 | 100Q17 | Live/Bead | Keypass/Live | 50Q17/Keypass | 100Q17/Keypass | IE | CF |
|---|---|---|---|---|---|---|---|---|---|---|---|
| 1 | 887653 | 459845 | 409575 | 139189 | 18070 | 0.52 | 0.89 | 0.3398 | 0.0441 | 0.89 | 1.22 |
| 2 | 869601 | 327546 | 298701 | 103027 | 6203 | 0.38 | 0.91 | 0.3449 | 0.0208 | 0.89 | 1.38 |
| 3 | 833990 | 314603 | 278195 | 85550 | 4256 | 0.38 | 0.88 | 0.3075 | 0.0153 | 0.94 | 1.46 |
| 4 | 784442 | 308623 | 266385 | 78011 | 4568 | 0.39 | 0.86 | 0.2929 | 0.0171 | 0.91 | 1.46 |
| 5 | 888552 | 415350 | 361947 | 34240 | 180 | 0.47 | 0.87 | 0.0946 | 0.0005 | 0.99 | 1.77 |
| 6 | 970019 | 369179 | 325557 | 33223 | 47 | 0.38 | 0.88 | 0.1020 | 0.0001 | 1.06 | 1.83 |
| 7 | 760317 | 362074 | 314624 | 14454 | 8 | 0.48 | 0.87 | 0.0459 | 0.0000 | 1.06 | 1.87 |

FIG. 6

SEQUENCE LISTING

<160> NUMBER OF SEQ ID NOS: 21

<210> SEQ ID NO 1
<211> LENGTH: 581
<212> TYPE: PRT
<213> ORGANISM: Bacillus stearothermophilus

<400> SEQUENCE: 1

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Gly Glu Asn Tyr
                20                  25                  30

His Asp Ala Pro Ile Val Gly Ile Ala Val Val Asn Glu His Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
        130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
```

```
                165                 170                 175
Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
            210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

His Glu Ile Val Glu Asn Ile Leu His Tyr Arg Gln Leu Gly Lys Leu
                275                 280                 285

Gln Ser Thr Tyr Ile Glu Gly Leu Leu Lys Val Val Arg Pro Asp Thr
                290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
                340                 345                 350

Leu Ile Phe Ala Ala Asp Tyr Ser Gln Ile Glu Leu Arg Val Leu Ala
                355                 360                 365

His Ile Ala Glu Asp Asp Asn Leu Met Glu Ala Phe Arg Arg Asp Leu
                370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
                420                 425                 430

Ser Arg Lys Glu Ala Ala Glu Phe Ile Glu Arg Tyr Phe Glu Ser Phe
                435                 440                 445

Pro Gly Val Lys Arg Tyr Met Glu Asn Ile Val Gln Glu Ala Lys Gln
                450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
                500                 505                 510

Met Ile Asp Leu Asn Ala Arg Leu Lys Glu Glu Arg Leu Gln Ala His
                515                 520                 525

Leu Leu Leu Gln Val His Asp Glu Leu Ile Leu Glu Ala Pro Lys Glu
                530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr His Tyr Gly Ser Thr
                565                 570                 575

Trp Tyr Asp Ala Lys
            580
```

<210> SEQ ID NO 2
<211> LENGTH: 581
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala

```
              355                 360                 365

His Ile Ala Glu Asp Asp Asn Leu Met Glu Ala Phe Arg Arg Asp Leu
        370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 3
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Ala Lys Met Lys Gln Tyr Glu Ala Val Arg
        115                 120                 125
```

```
Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
450                 455                 460

Lys Gly Tyr Val Thr Thr Leu Leu Arg Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
```

```
              545                 550                 555                 560

Val Thr Leu Arg Val Pro Leu Lys Val Asp Tyr Arg Tyr Gly Ser Thr
                        565                 570                 575

Trp Tyr Asp Ala Lys
                        580

<210> SEQ ID NO 4
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
                35                  40                  45

Phe Phe Leu Arg Pro Glu Thr Ala Leu Ala Asp Pro Gln Phe Val Ala
            50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
                100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
                195                 200                 205

Gly Lys Glu Leu Ala Glu Gln Leu Gly Thr Val Glu Gln Arg Ile Tyr
            210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

Arg Glu Ile Val Glu Asn Ile Leu Ala Tyr Arg Gln Leu Gly Lys Leu
        275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320
```

```
Leu Ser Ser Thr Glu Pro Asn Leu Gln Asn Ile Pro Ile Arg Leu Glu
            325                 330                 335

Glu Gly Arg Lys Ile Arg Gln Ala Phe Val Pro Ser Glu Ser Asp Trp
        340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
        370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
            405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
        450                 455                 460

Lys Gly Tyr Val Thr Thr Leu Leu Arg Arg Arg Arg Phe Leu Pro Asp
465                 470                 475                 480

Ile Thr Ser Arg Asn Phe Asn Val Arg Ser Phe Ala Glu Arg Met Ala
            485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
        530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
            565                 570                 575

Trp Tyr Asp Ala Lys
            580

<210> SEQ ID NO 5
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95
```

```
Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
            130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510
```

-continued

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 6
<211> LENGTH: 774
<212> TYPE: PRT
<213> ORGANISM: Thermococcus kodakaraensis

<400> SEQUENCE: 6

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

```
Asp Ile Pro Phe Ala Lys Arg Tyr Leu Ile Asp Lys Gly Leu Val Pro
            115                 120                 125
Met Glu Gly Asp Glu Glu Leu Lys Met Leu Ala Phe Asp Ile Glu Thr
    130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
    290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Arg Gln Ser Tyr
    370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
```

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Val Thr Lys Lys
            580                 585                 590

Lys Tyr Ala Val Ile Asp Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 7
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

```
His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Arg Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
            290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
            355                 360                 365

Thr His Glu Lys Gly Ala Lys Lys Gln Leu Ala Lys Leu Met Leu Asn
            370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Lys Phe Ser Val Lys Cys Ala
            515                 520                 525
```

```
Gly Met Thr Asp Thr Ile Lys Lys Val Thr Phe Asp Asn Phe Arg
            530             535             540
Val Gly Phe Ser Ser Thr Gly Lys Pro Lys Pro Val Gln Val Asn Gly
545             550             555             560
Gly Val Val Leu Val Asp Ser Val Phe Thr Ile Lys
            565             570

<210> SEQ ID NO 8
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
    50                  55                  60
Ala Phe Ile Val Asn Trp Leu Glu His His Gly Phe Lys Trp Ser Asn
65                  70                  75                  80
Glu Gly Leu Pro Asn Thr Tyr Asn Thr Ile Ile Ser Lys Met Gly Gln
                85                  90                  95
Trp Tyr Met Ile Asp Ile Cys Phe Gly Tyr Lys Gly Lys Arg Lys Leu
            100                 105                 110
His Thr Val Ile Tyr Asp Ser Leu Lys Lys Leu Pro Phe Pro Val Lys
        115                 120                 125
Lys Ile Ala Lys Asp Phe Gln Leu Pro Leu Leu Lys Gly Asp Ile Asp
    130                 135                 140
Tyr His Ala Glu Arg Pro Val Gly His Glu Ile Thr Pro Glu Glu Tyr
145                 150                 155                 160
Glu Tyr Ile Lys Asn Asp Ile Glu Ile Ala Arg Ala Leu Asp Ile
                165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
        195                 200                 205
Pro Lys Leu Ser Leu Pro Met Asp Lys Glu Ile Arg Arg Ala Tyr Arg
    210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
        275                 280                 285
Phe Glu Leu Lys Glu Gly Tyr Ile Pro Thr Ile Gln Ile Lys Lys Asn
    290                 295                 300
Pro Phe Phe Lys Gly Asn Glu Tyr Leu Lys Asn Ser Gly Ala Glu Pro
305                 310                 315                 320
```

Val Glu Leu Tyr Leu Thr Asn Val Asp Leu Glu Leu Ile Gln Glu His
            325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
            355                 360                 365

Thr His Glu Lys Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Arg
        530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 9
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
            85                  90                  95

Trp Tyr Met Ile Asp Ile Cys Phe Gly Tyr Lys Gly Lys Arg Lys Leu

-continued

```
                100                 105                 110
His Thr Val Ile Tyr Asp Ser Leu Lys Lys Leu Pro Phe Pro Val Lys
            115                 120                 125
Lys Ile Ala Lys Asp Phe Gln Leu Pro Leu Leu Lys Gly Asp Ile Asp
            130                 135                 140
Tyr His Ala Glu Arg Pro Val Gly His Glu Ile Thr Pro Glu Glu Tyr
145                 150                 155                 160
Glu Tyr Ile Lys Asn Ala Ile Glu Ile Ala Arg Ala Leu Asp Ile
            165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
            195                 200                 205
Pro Lys Leu Ser Leu Pro Met Asp Lys Glu Ile Arg Arg Ala Tyr Arg
            210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
                260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
            290                 295                 300
Pro Phe Phe Lys Gly Asn Glu Tyr Leu Lys Asn Ser Gly Ala Glu Pro
305                 310                 315                 320
Val Glu Leu Tyr Leu Thr Asn Val Asp Leu Glu Leu Ile Gln Glu His
                325                 330                 335
Tyr Glu Met Tyr Asn Val Glu Tyr Ile Asp Gly Phe Lys Phe Arg Glu
            340                 345                 350
Lys Thr Gly Leu Phe Lys Glu Phe Ile Asp Lys Trp Thr Tyr Val Lys
            355                 360                 365
Thr His Glu Lys Gly Ala Lys Lys Gln Leu Ala Lys Leu Met Leu Asn
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Ala Lys Glu Val Asp Gly Lys Leu Ile Glu
            500                 505                 510
Cys Ser Pro Asp Glu Ala Thr Thr Thr Lys Phe Ser Val Lys Cys Ala
            515                 520                 525
```

```
Gly Met Thr Asp Thr Ile Lys Lys Val Thr Phe Asp Asn Phe Arg
        530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570
```

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 10

Asp Xaa Ser Xaa Xaa Glu
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(7)
<223> OTHER INFORMATION: Any amino acid

<400> SEQUENCE: 11

Lys Xaa Xaa Xaa Xaa Xaa Xaa Tyr Gly
1               5
```

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus

<400> SEQUENCE: 12

Val His Asp Glu
1
```

```
<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(3)
<223> OTHER INFORMATION: Any amino acid

<400> SEQUENCE: 13
```

```
Asp Xaa Xaa Ser Leu Tyr Pro Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 14

```
Lys Xaa Xaa Xaa Asn Ser Xaa Tyr Gly
1               5
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus

<400> SEQUENCE: 15

```
Tyr Gly Asp Thr Asp Ser
1               5
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (6)..(6)
<223> OTHER INFORMATION: Phe or Tyr

<400> SEQUENCE: 16

```
Asp Xaa Xaa Xaa Xaa Xaa
1               5
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES -continued

```
<222> LOCATION: (7)..(7)
<223> OTHER INFORMATION: Ser or Ala

<400> SEQUENCE: 17

Phe Xaa Gly Xaa Xaa Xaa Xaa
1               5

<210> SEQ ID NO 18
<211> LENGTH: 575
<212> TYPE: PRT
<213> ORGANISM: Bacillus sp.
<220> FEATURE:
<223> OTHER INFORMATION: Bacteriophage Phi29

<400> SEQUENCE: 18

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Ala Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
```

```
                    325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
Leu Val Glu Gly Ser Pro Asp Asp Tyr Thr Asp Ile Lys Phe Ser Val
                515                 520                 525
Lys Cys Ala Gly Met Thr Asp Lys Ile Lys Lys Glu Val Thr Phe Glu
                530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 19
<211> LENGTH: 145
<212> TYPE: PRT
<213> ORGANISM: Escherichia coli

<400> SEQUENCE: 19

Ala Ser Arg Gly Val Asn Lys Val Ile Leu Val Gly Asn Leu Gly Gln
1               5                   10                  15
Asp Pro Glu Val Arg Tyr Met Pro Asn Gly Gly Ala Val Ala Asn Ile
                20                  25                  30
Thr Leu Ala Thr Ser Glu Ser Trp Arg Asp Lys Ala Thr Gly Glu Met
            35                  40                  45
Lys Glu Gln Thr Glu Trp His Arg Val Val Leu Phe Gly Lys Leu Ala
        50                  55                  60
Glu Val Ala Ser Glu Tyr Leu Arg Lys Gly Ser Gln Val Tyr Ile Glu
65                  70                  75                  80
Gly Gln Leu Arg Thr Arg Lys Trp Thr Asp Gln Ser Gly Gln Asp Arg
                85                  90                  95
Tyr Thr Thr Glu Val Val Asn Val Gly Gly Thr Met Gln Met Leu
                100                 105                 110
Gly Gly Arg Gln Gly Gly Gly Ala Pro Ala Gly Asn Ile Gly Gly
            115                 120                 125
```

```
Gly Gln Pro Gln Gly Gly Trp Gly Gln Pro Gln Gln Pro Gln Gly Gly
    130                 135                 140

Asn
145

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid

<400> SEQUENCE: 20

Tyr Xaa Asp Asp
1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(8)
<223> OTHER INFORMATION: Any amino acid

<400> SEQUENCE: 21

Gly Xaa Xaa Xaa Xaa Xaa Xaa Xaa Lys
1               5
```

MODIFIED PROTEINS AND METHODS OF MAKING AND USING SAME

This application is a divisional of U.S. application Ser. No. 14/724,354 filed May 28, 2015, now allowed, which is a Continuation of U.S. application Ser. No. 13/036,623, filed Feb. 28, 2011, now abandoned, which is a Continuation-in-Part of U.S. application Ser. No. 13/035,177, filed Feb. 25, 2011, now abandoned, which claims the benefit under 35 U.S.C. § 119 of U.S. Provisional Application No. 61/308,863, filed Feb. 26, 2010, all of which forgoing applications are herein incorporated by reference in their entireties. This application also claims the benefit of foreign priority to International Application Nos. PCT/US2011/026228, filed Feb. 25, 2011, and PCT/US2011/026468, filed Feb. 28, 2011, both of which applications are incorporated herein by reference in their entireties.

This application contains nucleotide sequence and/or amino acid sequence disclosure in computer readable form and a written sequence listing, the entire contents of both of which are expressly incorporated by reference in their entirety as though fully set forth herein.

BACKGROUND

The direct detection of chemical moieties, such as ions, has tremendous potential to simplify assay design and cost. For example, in some instances, such techniques can reduce or eliminate the need for costly labeling reagents; similarly, they can also eliminate the requirement for complex detection steps that may otherwise be necessary. The utility of such techniques can be illustrated by their application in the field of DNA sequence analysis, for which several chemical detection schemes have been described. These include the detection of polymerase extension by detecting physico-chemical byproducts of the extension reaction, such as pyrophosphate, hydrogen ion, charge transfer, heat, and the like, as disclosed, for example, in Pourmand et al, Proc. Natl. Acad. Sci., 103: 6466-6470 (2006); Purushothaman et al., IEEE ISCAS, IV-169-172; Rothberg et al, U.S. Patent Publication No. 2009/0026082; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Ion-based reactions, i.e., reactions involving the generation and detection of ions, are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-based sequencing (also referred to as "pH-based" nucleic acid sequencing) exploits the direct detection of hydrogen ions produced as a byproduct of nucleotide incorporation. In one exemplary system for ion-based sequencing, the nucleic acid to be sequenced is captured in a microwell, and nucleotides are floated across the well, one at a time, under nucleotide incorporation conditions. The polymerase incorporates the appropriate nucleotide into the growing strand, and the hydrogen ion that is released changes the pH in the solution, which is detected by an ion sensor. This technique does not require labeling of the nucleotides or expensive optical components, and allows for far more rapid completion of sequencing runs. Examples of such ion-based nucleic acid sequencing methods including the Ion Torrent PGM™ sequencer (Life Technologies Corporation).

For ion-based reactions, including ion-based nucleic acid sequencing, it is important to detect as many released ions as possible in order to achieve as high a signal, and a correspondingly high signal to noise ratio, as possible. Obtaining sufficient signal can be challenging given the rapid diffusion of ions away from the reaction site, as well as the buffering effects of other reaction components and the material of the container wall. For example, the buffering effects of proteins in an ion-based sequencing reaction can hinder the efficient detection of hydrogen ions.

There is a therefore a need for methods and compositions for reducing the buffering effects of protein reaction components, particularly for use in ion-based nucleic acid sequencing methods and systems.

SUMMARY

In some embodiments, the disclosure relates generally to compositions, methods, systems, apparatuses and kits comprising modified proteins having reduced buffering capacities as compared to their unmodified counterparts, as well as methods for making and using the modified proteins in a wide range of chemical reactions. In some embodiments, the disclosure relates generally to methods, compositions, systems and kits comprising modified proteins (e.g., nucleic acid binding proteins) for use in ion-based nucleic acid sequence determination. In some embodiments, the disclosure relates generally to compositions, methods, systems, kits and apparatuses for carrying out a plurality of label-free DNA sequencing reactions on a large-scale array of electronic sensors, for example field effect transistors ("FETs").

In some embodiments, the disclosure relates generally to a modified protein comprising one or more modifications that reduce the buffering capacity of the modified protein relative to the corresponding unmodified protein. Optionally, the one or more modifications reduce the buffering capacity of the modified protein within the range of about pH 4 to about pH 10. In some embodiments, the one or more modifications reduce the buffering capacity of the modified protein relative to the corresponding unmodified protein within the range of about pH 7 to about pH 9. In some embodiments, the one or more modifications include one or more amino acid additions, substitutions, deletions, additions or chemical modifications. In some embodiments, the modified protein includes one or more amino acid substitutions, which are not included in the unmodified protein.

In some embodiments, the disclosure relates generally to an isolated protein comprising one or more amino acid substitutions that reduce the buffering capacity of the protein relative to the corresponding wild-type protein within the range of about pH 4 to about pH 10. In some embodiments, the one or more amino acid substitutions reduce the buffering capacity of the protein relative to the corresponding wild-type protein within the range of about pH 7 to about pH 9.

In some embodiments, the modified protein is a nucleic acid binding protein. For example, the protein can have DNA- or RNA-binding activity. In various embodiments, the protein is selected from the group consisting of DNA polymerases, helicases, ligases, nucleases, single stranded DNA binding proteins and polymerase accessory proteins.

In some embodiments, the one or more amino acid substitutions substantially reduce the buffering capacity of said protein within the range of about pH 7 to pH 9. In some embodiments, at least one of the one or more amino acid substitutions is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the protein is a DNA polymerase. In some embodiments, the disclosure relates generally to an isolated DNA polymerase comprising one or more conservative amino acid substitutions that substantially reduce its buffering capacity relative to the corresponding wild-type protein within the range of about pH 7 to about pH 9. In some embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Bst polymerase, Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator™ polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 which is incorporated by reference herein.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 2 or Table 3. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the Bst DNA polymerase comprises one or more conservative amino acid substitutions, wherein the one or more amino acid substitutions includes a substitution of alanine at position 2 with Met, Asn, Gln, Leu, Ile, Phe, or Trp, the numbering of amino acid residues being in accordance with that of SEQ ID NO: 1.

In some embodiments, the disclosure relates generally to an isolated Bst DNA polymerase comprising an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the disclosure relates generally to an isolated variant of a protein comprising the amino acid sequence shown in SEQ ID NO: 2, wherein the variant comprises an amino acid sequence that is at least 95% identical to SEQ ID NO: 2.

In some embodiments, the disclosure relates generally to a Bst DNA polymerase comprising the amino acid sequence of SEQ ID NO: 3. In some embodiments, the disclosure relates generally to an isolated variant of a protein comprising the amino acid sequence shown in SEQ ID NO: 3, wherein the variant comprises an amino acid sequence that is at least 95% identical to SEQ ID NO: 3.

In some embodiments, the disclosure relates to a Bst DNA polymerase comprising the amino acid sequence of SEQ ID NO: 4. In other embodiments, the disclosure relates generally to an isolated variant of a protein comprising the amino acid sequence shown in SEQ ID NO: 4, wherein the variant comprises an amino acid sequence that is at least 95% identical to SEQ ID NO: 4.

In some embodiments, the DNA polymerase is a Therminator™ DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments, the isolated protein comprising one or more amino acid substitutions that reduce the buffering capacity of said protein relative to the corresponding wild-type protein within the range of about pH 4 to about pH 10 is a single stranded DNA binding protein (SSB).

In some embodiments, the SSB comprises one or more conservative amino acid substitutions that substantially reduce its buffering capacity within the range of pH 7 to pH 9. In further embodiments, the one or more conservative amino acid substitutions are selected from the group consisting of histidine to arginine, glutamic acid to glutamine, aspartic acid to asparagine, lysine to arginine, and tyrosine to phenylalanine. In some embodiments, the SSB is *E. coli* SSB. In further embodiments, the one or more conservative amino acid substitutions are of one or more amino acid residues shown in Table 4. In some embodiments, the SSB comprises the amino acid substitution K7R.

In some embodiments, the disclosure relates generally to an isolated protein comprising one or more amino acid substitutions that reduce the buffering capacity of said protein relative to the corresponding wild-type protein within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, Lys, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid modifications includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid modifications includes a substitution of an amino acid residue with an alanine residue.

In some embodiments, at least one of the one or more amino acid substitutions includes a substitution of an amino acid residue that is at least 30% solvent exposed in the corresponding wild-type protein with another amino acid residue.

In some embodiments, the disclosure relates generally to an isolated protein comprising one or more chemical amino acid modifications that reduce the buffering capacity of said protein relative to the corresponding wild-type protein within the range of about pH 4 to about pH 10. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In some embodiments, the amine-reactive reagent includes an acylating agent or an activated ester.

In some embodiments, the disclosure relates generally to an isolated polymerase protein comprising one or more amino acid additions, substitutions, deletions or chemical modifications that reduce the buffering capacity of said protein relative to the corresponding wild-type protein within the range of about pH 4 to about pH 10, wherein the isolated protein retains polymerase activity.

In other embodiments, the disclosure relates generally to an isolated protein of any of the embodiments described above, further including an affinity tag, a label, a chemical moiety, a radionuclide, an enzyme, a fluorescent marker, a chemiluminescent marker, or a combination thereof. In other embodiments, the isolated protein is coupled to a polymer, a support, or a sensor.

In other embodiments, the disclosure relates generally to an isolated nucleic acid that is at least 80% identical to a nucleic acid encoding a protein of any of the embodiments described above. In further embodiments, the disclosure relates generally to a vector comprising the isolated nucleic acid. In further embodiments, the disclosure relates generally to a host cell comprising the vector. In some embodiments, the host cell is a bacterial cell. In some embodiments, the bacterial cell has a reduced activity of methionine aminopeptidase (MAP) relative to a corresponding wild-type bacteria cell.

In other embodiments, the disclosure relates generally to a kit comprising an isolated protein of any of the embodiments described above.

In some embodiments, the disclosure relates generally to an isolated protein comprising one or more amino acid additions, substitutions, deletions or chemical modifications that reduce the buffering capacity of said protein relative to the corresponding wild-type protein within the range of about pH 4 to about pH 10, wherein the one or more amino acid substitutions substantially reduce the average number of sequencing errors obtained from an ion-based sequencing reaction using said protein, relative to the number of sequencing errors obtained from an ion-based sequencing reaction using the corresponding wild-type protein.

In some embodiments, the disclosure relates generally to an isolated nucleic acid binding polypeptide of claim comprising one or more amino acid substitutions, deletions or chemical modifications that reduce the buffering capacity of said protein relative to the corresponding wild-type protein within the range of about pH 4 to about pH 10, wherein the one or more amino acid substitutions, deletions or chemical modifications increase the average length of sequencing reads having at least 90% accuracy obtained from an ion-based sequencing reaction using said, relative to average length of sequencing reads having 90% accuracy obtained from an ion-based sequencing reaction using the corresponding wild-type protein.

In some embodiments, the disclosure relates generally to a method for incorporating at least one nucleotide into a primer, comprising: contacting a nucleic acid duplex including a template nucleic acid and a primer with a polymerase comprising one or more amino acid substitutions, deletions or chemical modifications that reduce the buffering capacity of said polymerase relative to the corresponding wild-type polymerase within the range of about pH 4 to about pH 10 in the presence of one or more nucleotides, and incorporating at least one nucleotide into the primer in a template-dependent fashion using said polymerase.

In some embodiments, the disclosure relates generally to methods for sequencing a nucleic acid using the modified proteins. In one exemplary embodiment, the disclosure relates generally to a method for obtaining sequence information from a nucleic acid template, comprising:

(a) providing a template nucleic acid hybridized to a sequencing primer and bound to a polymerase, wherein the polymerase comprises one or more amino acid substitutions that substantially reduce its buffering capacity within the range of about pH 4 to about pH 10;

(b) synthesizing a new nucleic acid strand by sequentially incorporating one or more nucleotides at the 3' end of the sequencing primer, wherein a hydrogen ion byproduct is generated when the nucleotide is complementary to corresponding nucleotides in the template nucleic acid; and (c) detecting the incorporation of the one or more nucleotides into the sequencing primer by detecting the release of hydrogen ions.

In some embodiments, the polymerase is a Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is E. coli SSB. In further embodiments, the one or more conservative amino acid substitutions in the SSB are of one or more amino acid residues shown in Table 4.

In another embodiment, the disclosure relates generally to a method for sequencing a nucleic acid, comprising: (a) disposing a plurality of template nucleic acids into a plurality of reaction chambers, wherein one or more of the reaction chambers are in contact with a field effect transistor (FET), and contacting at least one of the template nucleic acids with a polymerase including one or more conservative amino acid substitutions that substantially reduce its buffering capacity within the range of pH 7 to pH 9; (b) synthesizing a new nucleic acid strand by sequentially incorporating one or more nucleotides into a nucleic acid molecule and generating one or more hydrogen ions as a byproduct of such nucleotide incorporation; and (c) detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET is selected from the group consisting of: ion-sensitive FET (isFET) and chemically-sensitive FET (chemFET).

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is E. coli SSB. In further embodiments, the one or more conservative amino acid substitutions in the SSB are of one or more amino acid residues shown in Table 4.

In another embodiment, the disclosure relates generally to a method for sequencing a nucleic acid comprising:

(a) disposing a plurality of solid or semi-solid supports into a plurality of reaction chambers on a sensor array formed in a semiconductor substrate, at least one reaction chamber including a polymerase, a sequencing primer and a single solid or semi-solid support attached to a plurality of template nucleic acids having at least 80% sequence identity to each other, wherein the polymerase comprises one or more amino acid substitutions that substantially remove its buffering capacity within the range of pH 7 to pH 9, and each reaction chamber is in contact with or capacitively coupled to a sensor including a FET configured to provide at least one output representing the presence of one or more hydrogen ions in the reaction chamber;

(b) introducing at least one nucleotide into the at least one reaction chamber and incorporating the at least one nucleotide into the primer using the polymerase, thereby generating one or more hydrogen ion byproducts;

(c) detecting the incorporation of the at least one nucleotides by detecting the presence of the hydrogen ion byproducts.

In some embodiments, the method further includes repeating steps (a) through (c) until the nucleic acid is sequenced.

In some embodiments, the method further includes a step of washing unincorporated nucleotides from the at least one reaction chambers.

In some embodiments, the method further includes repeating steps (a) through (c) as well as the washing step until the nucleic acid is sequenced.

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is *E. coli* SSB. In further embodiments, the one or more conservative amino acid substitutions in the SSB are of one or more amino acid residues shown in Table 4.

In a further embodiment, the disclosure relates generally to a method for reducing the buffering capacity of a protein used in a DNA sequencing or amplification reaction, comprising making one or more amino acid substitutions in the protein sequence that substantially reduce the protein's buffering capacity within the range of about pH 4 to about pH 10.

In some embodiments, the amino acid substitutions substantially reduce the protein's buffering capacity within the range of about pH 7 to about pH 9.

In some embodiments, at least one of the one or more amino acid substitutions includes a substitution of an amino acid residue having a pKa in the range of about 4 to about 10 with an amino acid residue having a pKa less than about 4 or greater than about 10.

In some embodiments, the protein is a DNA- or RNA-binding protein.

In various embodiments, the protein is a DNA polymerase selected from the group consisting of a In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase; a B family DNA polymerase selected from the group consisting of Bst polymerase, Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase; a mixed-type polymerase selected from the group consisting of EX-Taq polymerase, LA-Taq polymerase, Expand polymerase series, and Hi-Fi polymerase; an unclassified DNA polymerase selected from the group consisting of Tbr polymerase, Tfl polymerase, Tru polymerase, Tac polymerase, Tne polymerase, Tma polymerase, Tih polymerase, and Tfi polymerase; and an RT polymerase selected from the group consisting of HIV reverse transcriptase, M-MLV reverse transcriptase and AMV reverse transcriptase.

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is *E. coli* SSB. In further embodiments, the one or more conservative amino acid substitutions in the SSB are of one or more amino acid residues shown in Table 2.

In a further embodiment, the disclosure relates generally to a method of detecting a nucleotide incorporation, comprising:

(a) performing a nucleotide incorporation using a modified polymerase and generating one or more hydrogen ions as a by-product of the nucleotide incorporation, where the modified polymerase includes one or more amino acid substitutions that reduce the buffering capacity of the modified polymerase relative to the unmodified polymerase; and (b) detecting the presence of the one or more hydrogen ions generated as a by-product of the nucleotide incorporation, thereby detecting the nucleotide incorporation.

In some embodiment, the modified polymerase includes one or more amino acid substitutions that reduce the buffering capacity of the modified polymerase within the pH range of about 4 to about 10 relative to the unmodified polymerase.

In some embodiments the detecting comprises using an ion-sensitive field effect transistor (ISFET). In some embodiments the ISFET is in an ISFET array.

In some embodiments the reaction is performed in a reaction chamber comprising or capacitively coupled to a chemFET.

In some embodiments, the reaction is in the presence of an agent that alters the value of a pKa of at least an amino acid in the modified polypeptide from within the range of about 6 to about 8 to less than about 6 or greater than about 8. In some embodiments, the agent is a phospholipid, a sulfonic acid surfactant, a polyanionic electrolyte or a salt thereof, a polycationic electrolyte or a salt thereof, tetramethyl ammonium or a salt thereof, or a combination thereof.

In some embodiments, the method further comprises repeating steps a)-b).

In a further aspect, the disclosure relates generally to a method of detecting a change in ion concentration during a chemical reaction, comprising:

(a) performing a chemical reaction in the presence of a modified polypeptide having one or more amino acid substitutions, wherein the concentration of at least one type of ion changes during the course of the chemical reaction; and (b) detecting a signal indicating the change in ion concentration, wherein the signal is increased relative to a signal that is detected from a chemical reaction performed in the presence of the unmodified polypeptide but under otherwise identical reaction conditions.

In some embodiments the modified polypeptide includes one or more amino acid substitutions that reduce the buffering capacity of the modified polypeptide relative to the unmodified polypeptide.

In some embodiments at least one of the one or more amino acid substitutions includes the substitution of an amino acid residue having a pKa of between about 4 and 10 with another amino acid residue having a pKa less than about 4 or greater than about 10.

In some embodiments the modified polypeptide is a modified polymerase, and the chemical reaction includes a nucleotide incorporation.

In some embodiments the detecting comprises using a chemFET. In some embodiments the chemFET is an ISFET. In some embodiments, the ISFET is in an ISFET array.

In some embodiments, the chemical reaction is performed in a reaction chamber comprising or capacitively coupled to a chemFET.

In some embodiments, the chemical reaction is in the presence of an agent that alters the value of a pKa of at least an amino acid in the modified polypeptide from within the range of about 6 to about 8 to less than about 6 or greater than about 8. In some embodiments, the agent is a phospholipid, a sulfonic acid surfactant, a polyanionic electrolyte or a salt thereof, a polycationic electrolyte or a salt thereof, tetramethyl ammonium or a salt thereof, or a combination thereof.

In some embodiments, the at least one type of ion is hydrogen ion.

In some embodiments, the reaction is an enzymatic reaction or a binding reaction.

In some embodiments, the chemical reaction is an enzymatic reaction. In some embodiments the enzymatic reaction is a nucleotide incorporation reaction.

In some embodiments, the method further comprises repeating steps a)-b).

BRIEF DESCRIPTION OF THE FIGURES

FIG. 1 shows the amino acid sequence of the large fragment of the Bst DNA polymerase. The conserved polymerase motifs are highlighted and underlined, and the invariant residues within these motifs are shown in bold.

FIG. 2 shows a sequence alignment of the amino acid sequences of the bacteriophage B103 DNA polymerase (SEQ ID NO:8) and the Phi29 DNA polymerase (SEQ ID NO:18).

FIG. 6 shows some exemplary data obtained from an ion-based sequencing reaction using a modified polymerase having the amino acid sequence of SEQ ID NO: 2 ("ion") and a reference polymerase having the amino acid sequence of SEQ ID NO: 1. The first four runs (Run Nos. 1-4) were performed using a modified polymerase having the amino acid sequence of SEQ ID NO: 1, while the last three runs (Run Nos. 5-7) were performed using the reference (unmodified) Bst polymerase having the amino acid sequence of SEQ ID NO: 1.

DETAILED DESCRIPTION

Figure 3:
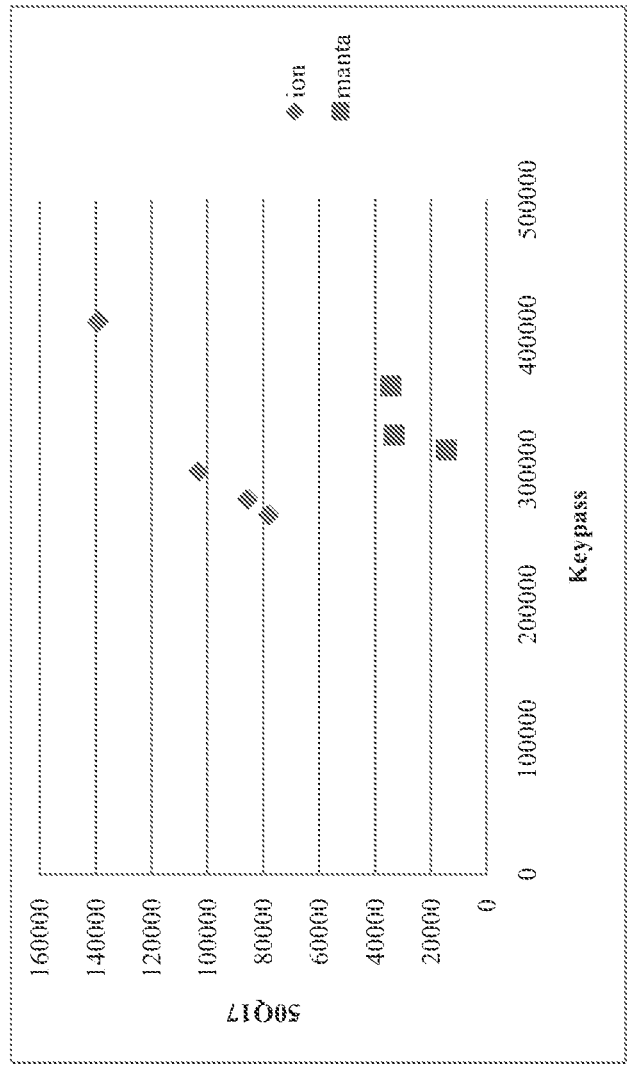
FIG. 3 shows the 50Q17 vs. Keypass for a sequencing reaction using the unmodified Bst DNA polymerase having the amino acid sequence of SEQ ID NO: 1 ("manta") and the modified Bst DNA polymerase having the amino acid sequence of SEQ ID NO: 2 ("ion").

All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

Unless otherwise defined, all terms of art, notations and other scientific terms or terminology used herein are intended to have the meanings commonly understood by those of skill in the arts to which this disclosure pertains. In some cases, terms with commonly understood meanings are defined herein for clarity and/or for ready reference, and the inclusion of such definitions herein should not necessarily be construed to represent a substantial difference over what is generally understood in the art.

Throughout this disclosure, various amino acid mutations, including, for example, amino acid substitutions are referenced using the amino acid single letter code, and indicating the position of the residue within a reference amino acid sequence. In the case of amino acid substitutions, the identity of the substituent is also indicated using the amino acid single letter code. For example, a reference to the hypothetical amino acid substitution "D166A, wherein the numbering is relative to the amino acid sequence of SEQ ID NO: 7" indicates an amino acid substitution wherein an alanine (A) residue is substituted for the normally occurring aspartic acid (D) residue at amino acid position 166 of the amino acid sequence of SEQ ID NO: 7. Many of the amino acid sequences disclosed herein begin with a methionine residue ("M"), which is typically introduced at the beginning of nucleic acid sequences encoding peptides desired to be expressed in bacterial host cells. However, it is to be understood that the disclosure also encompasses all such amino acid sequences beginning from the second amino acid residue onwards, without the inclusion of the first methionine residue.

As used herein, the term "amino acid" and its variants include without exception naturally occurring and synthetic amino acids, as well as amino acid analogs and amino acid mimetics that function in a manner similar to the naturally occurring amino acids. Naturally occurring amino acids are those encoded by the genetic code, including selenomethionine, as well as those amino acids that are modified after incorporation into a polypeptide, e.g., hydroxyproline, γ-carboxyglutamate, O-phosphoserine, and cystine. "Amino acid analog" refers to compounds that have the same basis chemical structure as a naturally occurring amino acid, i.e., an α-carbon that is bound by a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetic" refers to chemical compounds that have a structure that is different from the general chemical structure of an amino acid, but that functions in a manner similar to a naturally occurring amino acid. Amino acids may be referred to herein by either their commonly known three letter symbols or by their one letter symbols.

As used herein, the term "percent (%) amino acid sequence identity" and its variants, when used in reference to one or more polypeptide sequences, is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the terms "polynucleotide" and "oligonucleotide" and their variants, which can be used interchangeably, include a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Whenever a polynucleotide or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

As used herein, the term "primer" and its variants include any polynucleotide, either natural or synthetic that is capable, upon forming a duplex with a polynucleotide template, of acting as a point of initiation of nucleic acid synthesis and being extended from its 3' end along the template so that an extended duplex is formed. The primer need not exhibit 100% complementarity with the polynucleotide template, and may hybridize only partially with the nucleic acid template in order to be capable of initiating nucleic acid synthesis. Extension of a primer is usually carried out with a nucleic acid polymerase, such as a DNA or RNA polymerase. The sequence of nucleotides added in the extension process is typically determined by the sequence of the template polynucleotide. In some embodiments, template-dependent nucleotide incorporation proceeds according to standard base-pairing paradigms, such as the Watson-Crick paradigm wherein A nucleotides typically pair with T or U, and G typically pairs with C. In other embodiments, the order of nucleotide incorporation can be governed by any other, non-traditional base pairing paradigm.

In some embodiments, primers can be extended by a DNA polymerase or an RNA polymerase. The primers can optionally have a length in the range of from 14 to 40 nucleotides, or in the range of from 18 to 36 nucleotides. Primers can be employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2$^{nd}$ Edition (Cold Spring Harbor Press, New York, 2003).

In some embodiments, the disclosure relates generally to modified proteins having altered, e.g., increased or reduced, buffering capacities. Such modified proteins have utility, for example, in ion-sensitive reactions that involve the detection and/or quantification of ion byproducts (e.g., H+ ion or OH– ion byproducts) in the presence of the protein. Detection of such ion byproducts can be complicated by the intrinsic buffering capacity of the protein, which may result in binding of the protein to one or more ion byproducts, thereby reducing the number of ion byproducts available for detection and/or quantification. Use of a modified protein having a reduced buffering capacity can reduce or eliminate such complications, thereby increasing the amount of ions available for detection and/or quantification.

As used herein, the terms "buffering capacity" and its variants refer, among other things, to the ability of a composition to bind a particular type of ion (typically H+ ions or OH– ions) in solution. The greater the degree to which the particular type ion can be, or is, bound by composition, the higher the buffering capacity of the composition. For example, in some embodiments the buffering capacity of a particular composition (e.g., a protein) can be defined as the total mass of H+ ions (in moles or millimoles) absorbed by a unit mass (e.g., moles or millimole) of the composition (e.g., protein) under defined reaction conditions. Proteins typically exhibit a buffering capacity, which can be influenced by the number and type of side chains in the amino acid residues within the protein. In other embodiments, the buffering capacity of a composition can be measured as the composition's resistance to pH change upon addition of acid or base in solution. In such embodiments, the buffering capacity of a protein may be determined by performing a conventional pH titration on a known quantity of the candidate protein and determining the characteristics of the titration curve in the pH range of interest.

Typically, the modified proteins include one or more amino acid modifications, while the reference protein lacks at least one of these modifications. In some embodiments, the one or more amino acid modifications can alter (e.g., increase or reduce) the buffering capacity of the modified protein relative to the buffering capacity of the reference protein. The one or more modifications can include one or more amino acid substitutions, deletions, additions or chemical modifications. In one typical embodiment, the modified protein and the reference proteins are polymerases.

The reference protein can be any suitable protein whose buffering capacity can be measured and compared to the activity of a modified protein of the present disclosure. In some embodiments, the modified proteins include one or more amino acid modifications, while the reference protein lacks at least one of these modifications but is otherwise identical to the modified protein. In some embodiments, the reference protein can be the unmodified counterpart of the modified protein; for example, the reference protein can be the wild-type counterpart of the modified protein. In some embodiments, the reference protein is a naturally occurring protein.

In some embodiments, the modified proteins of the disclosure can exhibit reduced buffering capacity in a desired pH range. For example, in some embodiments, the reduced buffering capacity is manifested, or can be observed, within the range of from about pH 4 to about pH 10, or from about pH 5.5 to about pH 9.5, or from about pH 7 to about pH 9.

In some embodiments, the modified proteins of the disclosure can exhibit reduced buffering capacity such that relative small changes in concentration of hydrogen ions in a solution comprising the protein will produce relatively large changes in measured pH; such changes are typically greater than the changes in measured pH observed using the unmodified counterpart of the modified protein.

In some embodiments, the disclosure relates generally to modified proteins that have reduced buffering capacity relative to the corresponding unmodified (e.g., wild type protein).

In some embodiments, the modified protein comprises one or more amino acid substitutions that reduce the buffering capacity of the modified protein relative to the corresponding wild-type protein within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid modifications includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid modifications includes a substitution of an amino acid residue with an alanine residue.

In some embodiments, at least one of the one or more amino acid substitutions includes a substitution of an amino acid residue that is at least 30% solvent exposed in the corresponding wild-type protein with another amino acid residue.

In some embodiments of the method, the polymerase comprises one or more chemical amino acid modifications that reduce the buffering capacity of said protein relative to the corresponding wild-type protein within the range of about pH 4 to about pH 10. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In some embodiments, the amine-reactive reagent includes an acylating agent or an activated ester.

In some embodiments, at least one of the one or more amino acid modifications of the modified protein includes a substitution of an amino acid residue having a pKa of between about 4.0 and about 10.0 with an amino acid residue having a pKa that is greater than about 10.0 or less than about 4.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid modifications of the modified protein includes a substitution of an amino acid residue having a pKa within the range of about 6.0 to about 8.0 with another amino acid residue. The pKa can optionally be the solution pKa or the whole-protein pKa of the amino acid residue.

In some embodiments, at least one of the one or more amino acid modifications of the modified protein includes a substitution of an amino acid residue having a pKa of between about 6.0 and about 8.0 with an amino acid residue having a pKa that is greater than about 8.0 or less than about 6.0. In some embodiments, the amino acid to be substituted is His, Glu, Asp, Tyr or Lys.

In some embodiments, the modified protein includes at least one conservative amino acid substitution selected from the group consisting of His to Arg, Glu to Gln, Asp to Asn, Lys to Arg, and Tyr to Phe.

In some embodiments, at least one of the one or more amino acid modifications includes a substitution of an amino acid with an alanine residue.

In some embodiments, at least one of the one or more amino acid modifications includes a deletion of an amino acid. In some embodiments, at least one of the one or more deleted amino acids includes an amino acid residue having a pKa of between about 4.0 and about 10.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more deleted amino acids is an amino acid residue having a pKa within the range of about 6.0 to about 8.0 with another amino acid residue. In some embodiments, the deleted amino acid is His, Glu, Asp, Tyr or Lys.

The buffering capacity of a composition can be measured in various ways. In some embodiments, the buffering capacity of a composition can be measured in terms of the effect of the composition upon the concentrations of one or more types of ions in a solution. For example, the buffering capacity of a protein can be measured by measuring the H+ ion concentration in an aqueous solution that includes the protein. The solution can optionally include other components such as salts, nucleotides, and the like, which may or may not independently have buffering capacity. In other embodiments, the buffering capacity of a composition can be measured in terms of the amount of strong acid or base required to change the pH of a composition a given amount. Van Slyke (J. Biol. Chem. 52: 525-570 (1922)) provided a widely used conventional quantitative measure of buffering capacity, according to which, for a solution, buffering capacity is expressed as the amount of strong acid or base required to change the pH of one liter of the solution by one pH unit under standard conditions of temperature and pressure.

In some embodiments, the modified protein includes one or more modifications that increase or decrease the buffering capacity of the modified protein for a particular ion (e.g., H+ ions or OH– ions). For example, the one or more modifications can reduce the buffering capacity of the modified protein for hydrogen ions (e.g., $H^+$ ions). Optionally, the reduction in buffering capacity for $H^+$ ions is manifested over a particular pH range. In some embodiments, the one or more modifications can increase the intensity of the signal detected in an H+ ion-sensitive reaction, where the signal indicates the amount of H+ ions present in the ion-sensitive reaction. The H+ ion-sensitive reaction can be a nucleic acid sequencing reaction, wherein one or more H+ ions are released as a byproduct of nucleotide incorporation by a polymerase. In some embodiments, the signal indicating the amount of H+ ions present in the ion-sensitive reaction can be generated using a suitable field-effect transistor (FET), for example a chemFET or an isFET, as described in further detail below.

In some embodiments, the reduction in buffering capacity of the modified protein is determined by measuring the buffering capacity of the modified protein for a particular ion of interest (e.g., hydrogen ions), measuring the buffering capacity of a reference protein for the same ion, and comparing the buffering capacity of the modified protein to the buffering capacity of the reference protein. For example, an increase or decrease in the buffering capacity for hydrogen ions of particular modified protein can be determined by measuring the H+ ion concentration in a solution ("test solution") including the modified protein and comparing it to the H+ ion concentration in a solution ("reference solution") including the reference protein. In some embodiments, the modified protein is a mutant polymerase exhibiting reduced buffering capacity for H+ ions relative to a reference polymerase (for example, the corresponding wild-type version of the mutant polymerase) and the reduction in buffering capacity is determined by measuring the amount of H+ ions detected in a polymerase reaction solution including the modified protein, which is then compared to the amount of H+ ions measured in a polymerase reaction solution including the reference polymerase in lieu of the modified polymerase. In some embodiments, the amount of H+ ions present in test and/or reference solutions is measured using a FET, for example a chemFET or an isFET.

As used herein, the terms "buffer", "buffering agent" and their variants include any substance that binds H+ ions or OH– ions in solution. Typically, such buffers or buffering agents prevent or reduce any change in the acidity of a solution when an acid or base is added to the solution. For example, aqueous buffers typically scavenge H+ or OH– ions in an aqueous solution. Buffers can in some embodiments comprising a conjugate acid-base pair that scavenges the H+ or OH– ions in the solution. Any buffer will have a pKa value, the pH at which the buffer has its maximum buffering capacity. The buffering action of the buffer typically manifests over a pH range including from at least about one or two pH units below its pKa to at least about one or two pH units above its pKa value.

As used herein, the terms "non-buffering" and "bufferless" and their variants, when used in reference to a protein, refer to a protein having reduced, slight or no buffering capacity for a given type of ion (e.g., $H^+$ ions or $OH^-$ ions) in a given pH range. Such proteins can be useful for ion-based reactions requiring detection of the ion type in the presence of the protein. For example, a small change in the ion concentration can increase the amplitude of a signal indicating the ion concentration in a reaction including the modified protein, relative to a reaction including a protein having a higher buffering capacity. Typically, such non-buffering proteins include modified proteins that exhibit reduced buffering capacities for a given type of ion (e.g., $H^+$ ions, $OH^-$ ions) relative to their unmodified counterparts.

In some embodiments, the disclosure relates generally to use of modified proteins having reduced buffering capacity in nucleic acid sequencing or amplification reactions. The modified proteins may include both DNA and RNA binding proteins. Such proteins may or may not be directly involved in nucleic acid extension in such reactions, and may include nucleic acid polymerases, single stranded DNA binding proteins, ligases, helicases, nucleases, and polymerase accessory proteins. In some embodiments, the modified protein having altered (e.g., increased or decreased) buffering capacity is a polymerase. The polymerase can be a DNA polymerase or an RNA polymerase. As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion.

In some embodiments, the modified polymerases can be used to sequence nucleic acids in an ion-based sequencing reaction. One exemplary system is the Ion Torrent PGM™ sequencer (Life Technologies), which is an ion-based sequencing system that sequences nucleic acid templates by detecting ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer detects the nucleotide incorporations by detecting the hydrogen ion byproducts of the nucleotide incorporations. The Ion Torrent PGM™ sequencer includes a plurality of nucleic acid templates to be sequenced, each template disposed within a respective sequencing reaction well in an array. The wells of the array are each coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor provides output signals indicative of nucleotide incorporation which can be represented as voltage changes whose magnitude correlates with the $H^+$ ion concentration in a respective well or reaction chamber. Different nucleotide types are flowed serially into the reaction chamber, and are incorporated by the polymerase into an extending primer (or polymerization site) in an order determined by the sequence of the template. Each nucleotide incorporation is accompanied by the release of $H^+$ ions in the reaction well, along with a concomitant change in the localized pH. The release of $H^+$ ions is registered by the FET of the sensor, which produces signals indicating the occurrence of the nucleotide incorporation. Nucleotides that are not incorporated during a particular nucleotide flow will not produce signals. The amplitude of the signals from the FET may also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474, 897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In some embodiments, the disclosure relates generally to use of the modified proteins of the present disclosure in methods of ion-based sequencing. Typically, the modified protein is a polymerase including one or more amino acid substitutions that reduce the buffering capacity of the polymerase for $H^+$ ions relative to an unmodified (e.g., wild-type) counterpart under sequencing reaction conditions. Use of such modified polymerases having reduced buffering capacities in ion-based sequencing reactions is particularly advantageous because the intrinsic buffering capacity of the polymerase can reduce the number of $H^+$ ions available for detection by the FET sensor and thus reduce the magnitude of the signal, as well as decrease the signal-to-noise ratio, associated with nucleotide incorporation. Such signal interference resulting from the polymerase's buffering properties can result in sequencing errors and reduce the average error-free read length in an ion-based sequencing system.

In some embodiments, use of modified polymerases having reduced buffering capacities reduces or eliminates such effects, thereby increasing the magnitude of the voltage change associated with a particular nucleotide incorporation in an ion-based sequencing system.

In some embodiments, use of modified polymerases having reduced buffering capacities for $H^+$ ions can increase the magnitude of the signal indicating a nucleotide incorporation and/or decrease the signal-to-noise ratio for the signal obtained in an ion-based sequencing system.

In some embodiments, use of the modified polymerases having reduced buffering capacities for $H^+$ ions increases the average length of error-free sequencing reads having an error rate of no greater than 1 error per 100 nucleotides in an ion-based sequencing system.

In some embodiments, use of the modified polymerases having reduced buffering capacities for $H^+$ ions decreases the average sequencing error rate in an ion-based sequencing system.

In some embodiments, the modified polymerases exhibit reduced buffering capacities in for $H^+$ ions in a pH range of from about pH 4 to about pH 10. Sequencing reactions are typically performed at pH values of from about pH 6 to about pH 8. In some embodiments, the modified polymerases exhibit reduced buffering capacities in for $H^+$ ions in a pH range of from about pH 6 to about pH 8.

In some embodiments, the polymerases of the present disclosure can include without limitation naturally occurring polymerases and any subunits and truncations thereof, mutant polymerases, variant polymerases, recombinant, fusion or otherwise engineered polymerases, chemically modified polymerases, synthetic molecules or assemblies, and/or any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29-type DNA polymerase, reverse transcriptases and *E. coli* DNA polymerase) and RNA polymerases. In some embodiments, the modified polymerase can be a fusion protein comprising at least two portions linked to each other, where the first portion comprises a first polypeptide that can catalyze the polymerization of nucleotides into a nucleic acid strand, where the first portion is linked to a second portion that comprises a second polypeptide, such as, for example, a reporter enzyme or a processivity-enhancing domain One exemplary embodiment of such a polymerase is Phusion® DNA polymerase (New England Biolabs), which comprises a *Pyrococcus*-like polymerase fused to a processivity-enhancing domain as described, for example, in U.S. Pat. No. 6,627,424.

In some embodiments, the modified polymerase is derived from a known DNA polymerase. The DNA polymerases have been classified into seven different families, based upon both amino acid sequence comparisons and three-dimensional structure analyses. The DNA polymerase I (pol I) or type A polymerase family includes the repair polymerases *E. coli* DNA pol I, *Thermus aquaticus* pol I, and *Bacillus stearothermophilus* pol I, replicative DNA polymerases from some bacteriophages (T3, T5 and T7) and eukaryotic mitochondrial DNA polymerases. The DNA polymerase α (pol α) or type B polymerase family includes all eukaryotic replicating DNA polymerases as well as archaebacterial DNA polymerases, viral DNA polymerases, DNA polymerases encoded in mitochondrial plasmids of various fungi and plants, and the polymerases from bacteriophages T4 and RB69 Family C polymerases are the primary bacterial chromosome replicative enzymes. These are sometimes considered a subset of family Y, which contains the eukaryotic polymerase pol β, as well as other eukaryotic polymerases such as pol α, pol λ, pol μ, and terminal deoxynucleotidyl transferase (TdT) Family D polymerases are all found in the Euryarchaeota subdomain of Archaea and are thought to be replicative polymerases. The family Y polymerases are called translesion synthesis (TLS) polymerases due to their ability to replicate through damaged DNA. They are also known as error-prone polymerases since they have a low fidelity on undamaged templates. This family includes Pol η, Polζ, Pol ι (iota), Pol κ (kappa), and Rev1, and Pol IV and PolV from *E coli*. Finally, the reverse transcriptase family includes reverse transcriptases from retroviruses and eukaryotic polymerases, usually restricted to telomerases. These polymerases use an RNA template to synthesize the DNA strand, and are also known as RNA-dependent DNA polymerases.

In some embodiments, the modified polymerase includes one or more amino acid mutations that are located outside the catalytic domains of the polymerase. The catalytic domains of the A family DNA polymerases, B family DNA polymerases and reverse transcriptases, as well as the RNA-dependent RNA polymerases are well known; all share a common overall structure and catalytic mechanism. The catalytic domains of all these polymerases have a shape that has been compared to a right hand and consists of "palm", "thumb" and "finger" domains. The palm domain typically contains the catalytic site for the phosphoryl transfer reaction. The thumb is thought to play a role positioning the duplex DNA and in processivity and translocation. The fingers interact with the incoming nucleotide as well as the template base with which it is paired. The palm domains are homologous in the A, B and RT families, but the arrangements of the fingers and thumb are different. The thumb domains of the different polymerase families do share common features, containing parallel or anti-parallel α-helices, with at least one α-helix interacting with the minor groove of the primer-template complex. The fingers domain also conserves an α-helix positioned at the blunt end of the primer-template complex. This helix contains highly conserved side chains (the B motif).

Three conserved motifs, A, B, and C were originally identified for the A family polymerases. The A and C motifs were also found to be conserved in both the B family polymerases and the RT polymerases. (Delarue et al., Protein Engineering 3: 461-467 (1990)).

For the A family polymerases, the A motif comprises the consensus sequence:

```
                                            (SEQ ID NO: 10)
DXSXXE.
The B motif comprises the consensus sequence:
                                            (SEQ ID NO: 11)
KXXXXXXYG
The C motif comprises the consensus sequence
                                            (SEQ ID NO: 12)
VHDE
For the B family polymerases, the A motif
comprises the consensus sequence:
                                            (SEQ ID NO: 13)
DXXSLYPS.
The B motif comprises the consensus sequence:
                                            (SEQ ID NO: 14)
KXXXNSXYG
The C motif comprises the consensus sequence
                                            (SEQ ID NO: 15)
YGDTDS
```

The residues in bold indicate invariant residues. In some embodiments, the modified polymerase includes amino acid mutations (e.g., amino acid substitutions, deletions, additions or chemical modifications located at any position other than the invariant residues.

The A and C motifs are part of the palm domain, and each contains a strictly conserved aspartic acid residue, which are involved in the catalytic mechanism common to all the DNA polymerases. DNA synthesis is mediated by transfer of a phosphoryl group from the incoming nucleotide to the 3' OH of the DNA, releasing a polyphosphate moiety and forming a new DNA phosphodiester bond. This reaction is catalyzed by a mechanism involving two metal ions, normally $Mg^{2+}$, and the two conserved aspartic acid residues.

The conserved glutamic acid residue in motif A of the A family DNA polymerases plays an important role in incorporation of the correct nucleotide, as does the corresponding conserved tyrosine in B family members (Minnick et al., Proc. Natl. Acad. Sci USA 99: 1194-1199 (2002); Parsell et al, Nucleic Acids Res. 35: 3076-3086 (2002). Mutations at the conserved Leu of motif A affect replication fidelity (Venkatesan et al., J. Biol. Chem. 281: 4486-4494 (2006)).

The B motif contains conserved lysine, tyrosine and glycine residues. The B motif of *E coli* pol I has been shown to bind nucleotide substrates and contains a conserved tyrosine which has been shown to be in the active site.

The B family polymerases contain six conserved motifs, of which regions I and II correspond to the A and C motifs of the A family Region III is involved in nucleotide binding and is functionally homologous to motif B. Regions I, II and III converge at the center of the active site from the palm (I), the fingers (II), and base of the thumb (III) to produce a contiguous conserved surface. Within these regions, a set of highly conserved residues form three chemically distinct clusters consisting of exposed aromatic residues (Y416, Y567, and Y391), negatively charged residues (D621, D623, D411, D684, and E686), and a positively charged cluster (K560, R482, and K486). These three clusters encompass the region in which the primer terminus and the incoming nucleotide would be expected to bind. (Wang et al, Cell 89: 1087-1099 (1997)).

The RT polymerases contain four conserved sequence motifs (Poch et al., EMBO J. 12: 3867-3874 (1989)), with motifs A and C containing the conserved catalytic aspartates. The integrity of motif B is also required for reverse transcriptase function.

```
                                            (SEQ ID NO: 16)
The consensus sequence for motif A is DXXXXF/Y
                                            (SEQ ID NO: 17)
The consensus sequence for motif B is FXGXXXS/A
                                            (SEQ ID NO: 20)
The consensus sequence for motif C is YXDD
                                            (SEQ ID NO: 21)
The consensus sequence for motif D is GXXXXXXXK.
```

Mutations in the YXDD motif (motif C) (SEQ ID NO:20), the most highly conserved of these motifs, can abolish polymerase activity and alter the processivity and fidelity. (Sharma et al., Antiviral Chemistry and Chemotherapy 16: 169-182 (2005). In addition, the conserved lysine residue in motif D, a loop that is unique to the RT polymerases, is an invariant residue important for nucleotide binding (Canard et al., J. Biol. Chem. 274: 35768-35776 (1999).

In some embodiments, in addition to their polymerase domains, the modified polymerase can include one or more additional functional domains, including domains required for 3'→5' (reverse) exonuclease activity that mediates proofreading of the newly synthesized DNA strand, or for 5'→3' (forward) exonuclease activity that mediates nick translation during DNA repair. In some embodiments, the modified polymerase has strand-displacing activity, and can catalyze nucleic acid synthesis by polymerizing nucleotides into the 3' end of a nick within a double stranded nucleic acid template while simultaneously displacing the nucleic acid located downstream of the nick.

The 3' to 5' exonuclease proofreading domains of both A and B family DNA polymerases contain three conserved motifs, called Exo I, Exo II and Exo III, each of which contains an invariant aspartic acid residue essential for metal binding and exonuclease function. Alterations of these conserved aspartic acid residues result in proteins which retain polymerase activity, but are deficient in exonuclease activity. (Hall et al., J. Gen. Virol. 76: 2999-3008 (1995)). Conserved motifs in the 5' to 3' exonuclease domains and amino acid alterations that affect exonuclease activity have also been identified (U.S. Pat. No. 5,466,591).

Representative examples of A family enzymes are *E. coli*. Pol I, or the Klenow fragment of *E coli*. Pol I, Bst DNA polymerase, Taq DNA polymerase, T7 DNA polymerase and Tth DNA polymerase. A family enzymes also include the Platinum Taq DNA polymerase series. Examples of suitable polymerases in this family include Phi-29 DNA polymerase, B103 DNA polymerase, and the like.

It is generally thought that A family enzymes achieve high DNA elongation rates but have poor fidelity because of the lack of 3'-5' exonuclease activity, whereas B family enzymes have high fidelity owing to their 3'-5' exonuclease activity but achieve low DNA elongation rates. It is possible to form mixed-type enzymes by mixing and it is generally thought that A family enzymes achieve high DNA elongation rates but have poor fidelity because of the lack of 3'-5' exonuclease activity.

Unclassified types of enzymes include, for example, Tbr polymerase, Tfl polymerase, Tru polymerase, Tac polymerase, Tne polymerase, Tma polymerase, Tih polymerase, Tfi polymerase and the like. RT polymerases include HIV reverse transcriptase, Moloney Murine Leukemia Virus (M-MLV) reverse transcriptase, Avian Myeloblastosis Virus (AMV) reverse transcriptase or Rous Sarcoma Virus (RSV) reverse transcriptase. Variants, modified products and derivatives thereof are also usable.

Of these enzymes, Taq, Platinum Taq, Tth, Tli, Pfu, Pfutubo, Pyrobest, Pwo and KOD, VENT, DEEPVENT, EX-Taq, LA-Taq, Therminator™, the Expand series and Platinum Taq Hi-Fi are all commercially available. The other enzymes can be readily isolated from specific bacteria by those of ordinary skill in the art.

One exemplary polymerase, *E coli* DNA polymerase I ("Pol I") possesses three enzymatic activities: a 5' to 3' DNA polymerase activity; a 3' to 5' exonuclease activity that mediates proofreading; and a 5' to 3' exonuclease activity mediating nick translation during DNA repair. The Klenow fragment is a large protein fragment produced when *E. coli* Pol I is proteolytically cleaved by subtilisin. It retains the polymerase and proofreading exonuclease activities, but lacks the 5' to 3' exonuclease activity. An exo-Klenow fragment which has been mutated to remove the proofreading exonuclease activity is also available. The structure of the Klenow fragment shows that highly conserved residues that interact with DNA include N675, N678, K635, R631, E611, T609, R835, D827, S562 and N579 (Beese et al, Science 260: 352-355 (1993)).

Arg682 in the Klenow fragment of *E. coli* DNA polymerase I (pol I) is important for the template-dependent nucleotide-binding function, and appears to maintain high processivity of the DNA polymerase. Pandey et al., European Journal of Biochemistry, 214:59-65 (1993).

In some embodiments, the modified polymerase is derived from the Bst DNA polymerase of *Bacillus stearothermophilus*, which is another A family DNA polymerase. The large fragment of the Bst DNA polymerase is equivalent to the Klenow fragment of *E. coli* Pol I, retaining the polymerase and proofreading exonuclease activities while lacking the 5' to 3' exonuclease activity. Thus the term "Bst DNA polymerase" as used herein may refer to a full length protein or to a Bst large fragment.

In some embodiments, the modified polymerase is derived from Taq DNA polymerase, which is an A family DNA polymerase derived from the thermophilic bacterium *Thermus aquaticus*. It is best known for its use in the polymerase chain reaction. Taq polymerase lacks a proofreading activity, and thus has a relatively low replication fidelity. (Kim et al., Nature 376: 612-616 (2002).

In some embodiments, the modified polymerase is derived from the T7 DNA polymerase of bacteriophage T7, which is an A family DNA polymerase that consists of a 1:1 complex of the viral T7 gene 5 protein (80 k Da) and the *E. coli* thioredoxin (12 k Da). It lacks a 5'→3' exonuclease domain, but the 3'→5' exonuclease activity is approximately 1000-fold greater than that of *E coli* Klenow fragment. The exonuclease activity appears to be responsible for the high fidelity of this enzyme and prevents strand displacement synthesis. This polymerase is unique due to its considerable processivity, or ability to stay on DNA for a greater than average number of base pairs.

In some embodiments, the modified polymerase is derived from KOD DNA polymerase, which is a B family DNA polymerase derived from *Thermococcus kodakaraensis*. KOD polymerase is a thermostable DNA polymerase with high fidelity and processivity.

In some embodiments, the modified polymerase is derived from the Therminator™ DNA polymerase, which is also a B family DNA polymerase. Therminator™ is an A485L point mutation of the DNA polymerase from *Thermococcus* species 9oN-7. (Ichida et al., Nucleic Acids Res. 33: 5214-5222 (2005). Therminator™ polymerase has an enhanced ability to incorporate modified substrates such as dideoxynucleotides, ribonucleotides, and acyclonucleotides.

In some embodiments, the modified polymerase is derived from a Phi29 polymerase or a Phi29-type polymerase, for example a polymerase derived from the bacteriophage B103. The Phi29 and B103 DNA polymerases are B family polymerases from related bacteriophages. In addition to the A, B and C motifs, the Phi29 family of DNA polymerases contain an additional conserved motif, KXY in region Y (Blanco et al., J. Biol. Chem. 268: 16763-16770 (1993). Mutations to Phi29 and B103 polymerases that affect polymerase activity and nucleotide binding affinity are described in U.S. Patent Publication No. 20110014612 and its priority documents U.S. Provisional Application Nos. 61/307,356; 61/299,917; 61/299,919; 61/293,616; 61/293,618; 61/289,388; 61/263,974; 61/245,457; 61/242,771; 61/184,770; and 61/164,324, herein incorporated by reference in their entireties.

In some embodiments, the modified polymerase is derived from the reverse transcriptase from human immunodeficiency virus type 1 (HIV-1), which is a heterodimer consisting of one 66-kDa and one 51-kDa subunit. The p66 subunit contains both a polymerase and an RNase H domain; proteolytic cleavage of p66 removes the RNase H domain to yield the p51 subunit. Wang et al., PNAS 91:7242-7246 (1994). The structure of the HIV-1 reverse transcriptase shows multiple interactions between the 2'-OH groups of the RNA template and the reverse transcriptase. Residues Ser280 and Arg284 of helix I in the p66 thumb are involved in the RNA-RT interactions, as well as residues Glu89 and Gln91 of the template grip in the p66 palm. The p51 subunit also plays a role in the interactions between the RNA-DNA duplex and the RT, with residues Lys395, Glu396, Lys22 and Lys390 of the p51 subunit also interacting with the DNA: RNA duplex. (Kohlstaedt et al, Science 256: 1783-1790 (1992). Safarianos et al, The EMBO Journal 20:1449-1461 (2001)).

In some embodiments, the modified proteins of the disclosure can be derived from proteins, particularly nucleic acid binding proteins, which can be useful to include in nucleotide incorporation and/or nucleic acid sequencing applications. Many DNA polymerases interact with accessory proteins such as the single-stranded DNA binding protein, the sliding clamp protein, and others. The DNA clamp proteins are multimeric proteins that completely encircle the DNA and can significantly increase polymerase processivity. The clamp proteins include the processivity factor-sliding clamp for bacterial DNA polymerases II and III, gp45 for T4 DNA polymerase, UL44 for cytomegalovirus DNA polymerase, UL30 for herpes simplex virus I DNA polymerase, and proliferating cell nuclear antigen for eukaryotic DNA polymerases (Lee et al., J. Biol. Chem. 295:1490-1499 (2010). Use of such modified proteins in ion-based nucleotide incorporation and sequencing reactions offers the same advantages as does use of modified polymerases, namely, reduced interference with the ion-based sequencing signal, increased signal to noise ratio, reduction of sequencing error rate, and increase in average error-free sequencing read length.

In some embodiments, the modified protein is derived from a single stranded DNA binding protein. The single stranded DNA binding proteins (SSBs) are proteins that preferentially bind single stranded DNA (ssDNA) over double-stranded DNA in a nucleotide sequence independent manner SSBs have been identified in virtually all known organisms, and appear to be important for DNA metabolism, including replication, recombination and repair. Naturally occurring SSBs typically are comprised of two, three or four subunits, which may be the same or different. In general, naturally occurring SSB subunits contains at least one conserved DNA binding domain, or "OB fold" (Philipova et al. (1996) Genes Dev. 10:2222-2233; and Murzin (1993) EMBO J. 12:861-867), such that naturally occurring SSBs have four or more OB folds.

The best characterized SSB is that from *E. coli*, which exists as a tetramer. (Raghunathan, Nature Structural & Molecular Biology 7, 648-652 (2000). The *E coli* SSB (EcoSSB) monomer comprises an N-terminal domain rich in helices and sheets and a less structured C-terminal domain. The N-terminal domain contains the OB fold, while the C-terminal domain contains a highly conserved acidic region that weakens binding of EcoSSB to DNA, but may be involved in interactions with other proteins in vivo. The addition of single-stranded DNA-binding protein (SSB) in DNA sequencing reactions has been found to dramatically increase the resolution of sequencing runs. (Rapley (1994) Molecular Biotechnology 2: 295-298.) SSBs are also used to increase the efficiency of PCR. (Kur et al., Acta Biochimica Polonica 52: 569-574 (2005). SSBs are available commercially and are used to improve the processivity and fidelity of DNA polymerases (U.S. Patent Publication No. 20070059713).

In some embodiments, the modified proteins of the disclosure can be derived from DNA ligases. Ligases are essential components of DNA replication, recombination, and repair systems found from viruses to humans, catalyze the formation of a phosphodiester bond at single-stranded breaks on duplex DNA (Lehman, I. R., Science, 186:790-797 (1974)). DNA ligases can be classified into two families based on cofactor dependence. ATP-dependent ligases are found in bacteriophages (Dunn, et al., J Mol Biol., 148(4): 303-330 (1981) and Weiss, et al., Proc Natl Acad Sci USA, 57(4):1021-1028 (1967)), Chlorella virus PBCV-1 (Ho, et al., J Virol, 71(3):1931-19374 (1997)), Vaccinia virus (Shuman, S., Biochemistry, 34(49):16138-161475 (1995)), Archea (Kletzin, A., Nucleic Acids Res, 20(20):5389-5396 (1992) and Bult, et al., Science, 273(5278):1058-1073 (1996)), yeasts (Andaluz, et al., Yeast, 12(9):893-8988 (1996), Ramos, et al., Nucleic Acids Res, 25(8); 1485-1492 (1997), Schar, et al., Genes Dev, 11(15):1912-1924 (1997)), mammalian (Tomkinson, et al., Bioessays, 19(10):893-901 (1997), Tomkinson, et al., Mutat Res, 407(1):1-9 (1998), and Wang, et al., J Biol Chem, 269(50):31923-3192811 (1994)), and more recently eubacteria (Cheng, et al., Nucleic Acids Res, 25(7):1369-1374 (1997) and Deckert, et al., Nature, 392(6674):353-358 (1998)). NAD+ (i.e. nicotinamide adenine dinucleotide)-dependent ligases, however, are found exclusively in eubacteria. While some higher eucaryotic organisms may use multiple ATP (i.e. adenosine triphosphate)-dependent ligases to fulfill diverse biological functions, some simple eubacteria genomes could host both an NAD+-dependent ligase and an ATP-dependent ligase (Deckert, et al., Nature, 392(6674):353-358 (1998) and Fleischmann, et al., Science, 269(5223):496-512 (1995)). The origin of the additional ATP-dependent ligases in these genomes remains to be determined.

Although the ATP-dependent ligases and NAD+-dependent ligases share little sequence homology, all the ligases investigated so far use the same motif to form an adenylated enzyme intermediate (Tonikinson, et al., Bioessays, 19(10): 893-901 (1997), Shuman, et al., Virology, 211(1):73-83 (1995), and Luo, et al., Nucleic Acids Res, 24(15):3079-3085 (1996)). Furthermore, they seem to be organized by similar domains and structural folds ((Doherty, et al., Nucleic Acids Res, 24(12):2281-2287 (1996), Subramanya, et al., Cell, 85(4):607-615 (1996), and Sekiguchi, et al., Nucleic Acids Res, 25(4):727-734 (1997)).

In some embodiments, the modified proteins of the disclosure can be derived from helicases, which are motor proteins that move directionally along a nucleic acid phosphodiester backbone, separating two annealed nucleic acid strands (i.e., DNA, RNA, or an RNA-DNA hybrid) using energy derived from ATP hydrolysis. All helicases contain the classical Walker A and B motifs, associated with ATP-binding and Mg2+-binding (reviewed in Caruthers and McKay. Curr. Opin. Struct. Biol. 12:123-133 (2002), Soultanas and Wigley. Trends Biochem. Sci. 26:47-54 (2001)). Helicases have been classified into several superfamilies (Gorbalenya and Koonin. Curr. Opin. Struct. Biol. 3:419-429 (1993)) according to the number of helicase signature motifs and differences in the consensus sequences for motifs. Superfamilies 1 and 2 have seven characteristic helicase signature motifs and include helicases from archaea, eubacteria, eukaryotes and viruses, with helicases unwinding duplex DNA or RNA in either 3' to 5' direction or 5' to 3' direction. Examples of superfamily 1 helicases include the *E. coli* UvrD helicase, the *T. tengcongensis* UvrD helicase, and the B subunit of RecBCD. Superfamily 3 has three motifs and superfamily 4 has five motifs. Examples of superfamily 4 helicases include the T7 Gp4 helicase and DnaB helicases.

Helicases may be used in helicase dependent amplification (HDA) methods for in vitro DNA amplification. In contrast to PCR, which requires thermocycling to separate the two DNA strands, HAD utilizes a DNA helicase to generate single-stranded templates for primer hybridization and subsequent primer extension by a DNA polymerase.

Since the use of a helicase eliminates the need for thermocycling, HDA can be performed at a single temperature for the entire process. (Vincent et al, EMBO Reports 5: 795-800 (2004)).

Examples of naturally occurring DNA helicases, described by Kornberg and Baker in chapter 11 of their book, DNA Replication, W.H. Freeman and Company (2nd ed. (1992)), include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in the disclosed sequencing methods include RecQ helicase (Harmon and Kowalczykowski, J. Biol. Chem. 276:232-243 (2001)), thermostable UvrD helicases from *T. tengcongensis* (U.S. Pat. No. 7,829,284) and *T. thermophilus* (Collins and McCarthy, Extremophiles. 7:35-41. (2003)), thermostable DnaB helicase from *T. aquaticus* (Kaplan and Steitz, J. Biol. Chem. 274:6889-6897 (1999)), and MCM helicase from archaeal and eukaryotic organisms ((Grainge et al., Nucleic Acids Res. 31:4888-4898 (2003)).

In some embodiments, the modified proteins of the disclosure can be derived from a nuclease. Nucleases are enzymes that cleave the phosphodiester bonds between the nucleotide subunits of nucleic acids. Endonucleases cleave phosphodiester bonds within a polynucleotide chain, while exonucleases cleave phosphodiester bonds at the end of a polynucleotide chain.

During DNA synthesis the 3' and 5' exonucleases function to remove unwanted nucleotides from the DNA. Occasionally, a DNA polymerase will add an incorrect nucleotide to the growing DNA polymer. A 3' exonuclease removes nucleotides that have been incorrectly polymerized into DNA chains. These exonucleases are referred to as "proofreading" exonucleases.

In many cases the exonuclease activity is contained in the same protein as the DNA polymerase activity. For example, the *Escherichia coli* DNA polymerase I is a single polypeptide with three separate domains, or regions of function. Each of these three domains contains an enzymatic activity. The DNA polymerase activity is in one domain, and the two other domains contain 3' and 5' exonuclease activities. The 3' exonuclease proofreads for the DNA polymerase, and the 5' exonuclease removes unwanted nucleotides in advance of the DNA polymerase.

In some embodiments, the modified proteins of the disclosure can be derived from a topoisomerase. DNA topoisomerases are a specialized class of nucleases that bind to either single-stranded or double-stranded DNA and cut the phosphate backbone of the DNA. This intermediate break allows the DNA to be untangled or unwound, and, at the end of these processes, the DNA is reconnected again. Type I topoisomerases cut one strand of a DNA double helix, while type II topoisomerases cut both strands of one DNA double helix, pass another unbroken DNA helix through it, and then reanneal the cut strand. Type I topoisomerases include topo I, topo III and topo V. Type II topoisomerases include eukaryotic topo II, *E. coli* gyrase, *E. coli* topo IV, and topo VI. (Champoux JJ (2001) Annu. Rev. Biochem. 70: 369-413).

An example of a DNA topoisomerase that has been used in DNA sequencing reactions is Topoisomerase V from *Methanopyrus kandleri*, commercially available as Fidelase™. (U.S. Pat. No. 5,656,463). This thermostable topoisomerase is used to enzymatically unlink and denature plasmid DNA, to help DNA polymerase pass through strong secondary structures and to protect DNA from thermal decomposition.

In some embodiments, the disclosure also relates generally to methods for forming modified proteins having altered (e.g., increased or decreased) buffering properties relative to the unmodified protein. For example, in some embodiments, the disclosure relates generally to methods for forming modified polymerases having reduced buffering capacities for $H^+$ ions within pH ranges of from about pH 4 to about pH 10, typically from about pH 6 to about pH 9, even more typically from about pH 7 to about pH 9.

In some embodiments, the modified proteins of the disclosure include proteins that have been modified to substitute, delete or chemically modify any chemical groups that have a pKa within the pH range of interest Amino acid side chains that are targeted for substitution, deletion or modification include those having a pKa within the range of interest, and which are likely to be on the surface of a protein.

In some embodiments, the selection of amino acid residues for mutation is based on analysis of the buffering properties, particularly the pKa value, of the amino acids of the protein Amino acid residues having pKa values that correspond to the pH range of desired reaction conditions are likely to have stronger buffering capacities at the desired reaction conditions. For example, the modified proteins of the disclosure can be obtained by identifying amino acid residues within the protein that have, or are predicted to have, pKa values falling outside typical reaction conditions employed for the target protein-based assay, and replacing or substituting one or more of the identified amino acid residues with different amino acid residues having, or predicted to have, pKa values outside the intended range of operation. Such substitutions should reduce the buffering capacity of the overall protein since the new amino acid residues will be expected to buffer only weakly, if at all, under the reaction conditions that are typically employed in applications using the protein.

In some embodiments, these general principles of amino acid selection and mutation can be applied to produce modified nucleic acid binding proteins (e.g., polymerases, ligases, helicases, SSBPs and the like), having reducing buffering capacities for $H^+$ ions in primer extension assays and nucleotide incorporation reactions (including nucleic acid sequencing reactions). In some embodiments, the pKa values of the amino acid residues of a candidate protein can be predicted and evaluated to identify all amino acid residues in the protein having pKa values falling within the range of intended operating conditions for the protein. Standard operating conditions for protein-based assays typically correspond to physiological conditions and are well known in the art. Standard operating conditions for protein assays, especially assays involving nucleic acid binding proteins and enzymes, typically include pH ranges of from about pH 4 to about pH 10, more typically from about pH 6 to about pH 9, even more typically from about pH to about pH 9. In some embodiments, the pKa values of the amino acid residues of a candidate protein can be predicted and evaluated to identify all amino acid residues in the protein having pKa values falling within the range of about pH 4 to about pH 10, more typically from about pH 6 to about pH 9, even more typically from about pH 7 to about pH 9, thereby identifying a first pool of candidate amino acid residues for modification.

In some embodiments, the amino acid residue to be modified is selected based not only on the pKa value but also on the degree of solvent exposure of the amino acid residue. For example, the candidate amino acid residues for modification can be selected based on their predicted pKa value (e.g., selecting all amino acid residues having, or predicted to have, a pKa falling within a desired pH range covering intended operating conditions) as well as their solvent exposures (e.g., selecting amino acid residues having, or predicted to have, solvent exposures of at least 30%, typically of at least about 40%, optionally having solvent exposures of at least about 50%, 60%, 70%, 80%, or 90%). The solvent exposure of an amino acid in a protein measures the extent to which the amino acid is accessible to the solvent (usually water) surrounding the protein, a parameter that can also be variously referred to as surface exposure or solvation. The equivalent converse parameter is the degree to which an amino acid residue is buried (% buried) within the protein; an amino acid residue that is 20% buried is one that is 80% solvent exposed. The solvent accessibility (or conversely, the % burying) of an amino acid within a protein structure may be determined by a variety of suitable methods, including by visual analysis of the a three-dimensional rendering of protein structure (e.g., crystal structure), or by software analysis of the protein structure using methods known in the art (Lee and Richards, J. Mol. Biol. 55(3): 379-400 (1971); Shrake and Rupley, J. Mol. Biol. 79(2): 351-371 (1973); Connolly, J. Appl. Cryst. 16: 548-558 (1983)). A number of molecular graphics programs are available which allow for the determination of accessible surface area of amino acids within a protein structure, such as Rasmol, Charmm, AMBER, Swiss-PDBviewer, PropKa, and the like. In cases where the three-dimensional structure of the protein is not known, it may be modeled based upon sequence homology to a protein having a known structure using molecular modeling methods known in the art.

In some embodiments, the first pool of candidate amino acids, which have been selected based on pKa values, can be further narrowed by identifying all amino acid residues within the first pool having, or predicted to have, at least a minimum threshold degree of surface exposure, also referred to as solvent exposure or solvation Amino acid residues having, or predicted to have, degrees of solvation equal to or exceeding this threshold can be identified and selected to identify a second pool of candidate amino acids for modification. In some embodiments, the second pool of candidate amino acids includes all amino acid residues of the first pool having at least about 30% solvent exposure, typically at least about 50% solvent exposure, even more typically at least about 60% solvent exposure, even more typically at least about 70% solvent exposure).

Methods for forming a modified protein can optionally include modifying at least one of the amino acid residues in the candidate pool, thereby forming a modified protein having altered (e.g., increased or decreased) buffering capacities relative to the unmodified protein.

In some embodiments, one or more of the amino acid residues of the first pool of candidate amino acids, or the second pool of candidate amino acids, can optionally be substituted with a different amino acid residue having a pKa value falling outside the range of intended operation, for example having pKa values that are outside the pH ranges of from about pH 4 to about pH 10, more typically outside the range of from about pH 6 to about pH 9, even more typically outside the range of from about pH 7 to about pH 9.

In some embodiments of the method, the comprises one or more amino acid substitutions that reduce the buffering capacity of said protein relative to the corresponding wild-type protein within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In some embodiments, particularly for internal amino acid residues lacking a primary amine or free carboxylic group (e.g., non-terminal amino acid residues), the pKa of the amino acid residue is approximated as the pKa value of the side chain of the amino acid residue in solution. In other embodiments, the pKa of the amino acid residue is a pKa of the amino acid residue in the context of the corresponding wild-type protein (e.g., the "whole-protein pKa").

In some embodiments, the modifying can include substituting at least one amino acid residue having a pKa of between about 4.0 and about 10.0 with an amino acid residue having a pKa that is greater than about 10.0 or less than about 4.0. For example, the amino acid residue having a pKa that is greater than about 10.0 or less than about 4.0 can be selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, the modifying includes substituting at least one amino acid residue having a pKa within the range of about 6.0 to about 8.0 with another amino acid residue.

In some embodiments, the modifying includes substituting at least one amino acid residue having a pKa of between about 6.0 and about 8.0 with an amino acid residue having a pKa that is greater than about 8.0 or less than about 6.0.

In some embodiments, the modifying includes substituting at least one amino acid residue selected from the group consisting of: His, Glu, Asp, Tyr, and Lys, with any other different amino acid residue.

In some embodiments, the modifying includes substituting at least one amino acid residue of the protein with an alanine residue.

In some embodiments, the modifying includes substituting at least one amino acid residue that is at least 30% solvent exposed in the corresponding wild-type protein with another amino acid residue.

In some embodiments of the method, the modifying includes introducing at least one chemical amino acid modification that reduces the buffering capacity of said protein relative to the corresponding wild-type protein within the range of about pH 4 to about pH 10. In some embodiments, the at least one chemical amino acid modification includes a chemical modification of the N-terminal amino acid. In some embodiments, the at least one chemical amino acid modification includes a chemical modification of an amino acid residue including a primary amine group with an amine-reactive agent. In some embodiments, the amine-reactive reagent includes an acylating agent or an activated ester.

In some embodiments, the disclosure relates generally to methods for reducing the buffering capacity of a protein used in a DNA sequencing or amplification reaction, comprising making one or more conservative amino acid substitutions in the protein sequence that substantially remove the protein's buffering capacity within the range of pH 7 to pH 9.

Any suitable methods for designing and introducing modifications into proteins may be used to design, engineer and synthesize the modified proteins of the disclosure. Methods of genetically engineering nucleic acid sequences encoding proteins to selectively introduce mutations, optionally in a site-specific fashion, are well known in the art of recombinant nucleic acid engineering, as are methods for cloning, expressing and purifying such sequences in vivo or in vitro. Some exemplary methods of cloning, expression and purification are described in further detail herein.

In some embodiments, the protein can be modified by changing the pKa values or ranges of selected amino acid residues. The pKa of a composition (e.g., an amino acid) is a logarithmic measure of the acid dissociation constant Ka. An acid dissociation constant, Ka, (also known as acidity constant, or acid-ionization constant) is a quantitative measure of the strength of an acid in solution. It is the equilibrium constant for a chemical reaction known as dissociation in the context of acid-base reactions. By modifying pKa values of amino acids in a polypeptide, the ability of the polypeptide to absorb hydrogen ions may alter (e.g., increase or decrease), and/or its effect in ion detection and buffering capacity.

The pKa values of amino acid side chains of a protein can play an important role in defining the pH-dependent characteristics of a protein. The pH-dependence of the activity displayed by enzymes and the pH-dependence of protein stability, for example, are properties that are typically determined by the pKa values of amino acid side chains. The pKa value of an amino acid residue may be the solution pKa value, a pKa value based on the amino acid itself, but not on interaction with other amino acids in the protein environment.

The pKa of the amino acid residues of a particular protein can be inferred or estimated or determined using any suitable method. Various methods for inferring the pKa value of a particular amino acid residue of a protein are known in the art. For example, the pKa values of amino acid side chains can be inferred from the pKa values of model compounds that are similar to the side chains of amino acids. The pKas of the α-carboxylic acid, α-amino group, and titratable side chains for the free amino acids in solution are well known in the art and available in standard tables, an example of which is provided in Table 1.

TABLE 1

Some Typical pKa Values For Free Amino Acids In Solution

| Amino Acid | α-carboxylic acid | α-amino | Side chain |
|---|---|---|---|
| Alanine | 2.35 | 9.87 | |
| Arginine | 2.01 | 9.04 | 12.48 |
| Asparagine | 2.02 | 8.80 | |
| Aspartic Acid | 2.10 | 9.82 | 3.86 |
| Cysteine | 2.05 | 10.25 | 8.00 |
| Glutamic Acid | 2.10 | 9.47 | 4.07 |
| Glutamine | 2.17 | 9.13 | |
| Glycine | 2.35 | 9.78 | |
| Histidine | 1.77 | 9.18 | 6.10 |
| Isoleucine | 2.32 | 9.76 | |
| Leucine | 2.33 | 9.74 | |
| Lysine | 2.18 | 8.95 | 10.53 |
| Methionine | 2.28 | 9.21 | |
| Phenylalanine | 2.58 | 9.24 | |
| Proline | 2.00 | 10.60 | |
| Serine | 2.21 | 9.15 | |
| Threonine | 2.09 | 9.10 | |
| Tryptophan | 2.38 | 9.39 | |
| Tyrosine | 2.20 | 9.11 | 10.07 |
| Valine | 2.29 | 9.72 | |

In some embodiments, the solution pKa value may be a model pKa value. For example, the pKa values of an amino acid side chain in solution can be inferred from the pKa values of model compounds (e.g., compounds that are similar to the side chains of amino acids).

In some embodiments, the pKa value of an amino acid residue of a protein can be estimated by simply approximating it to the value of its side chain residue, as indicated in Table 1. In other words, the pKa value of an amino acid residue (particularly an internal amino acid residue) can be estimated as equal to the pKa value of its side chain, as indicated in Table 1. An amino acid residue to be substituted, deleted or modified may be selected based upon its solution pKa.

In some embodiments, the pKa value of an amino acid residue of a protein can be estimated using available tools (e.g., software) that predict the pKa value of the amino acid residue in the context of the whole protein. The pKa value of a given amino acid residue of a folded protein (referred to herein as the "whole-protein pKa" of the amino acid residue) can be different from the pKa of the free amino acid in solution (referred to herein as the "solution pKa" of the amino acid residue). In a folded protein, an amino acid residue (including its titratable amino acid side chain) may be buried within the interior of the protein and have limited or no exposure to solvent, and may also interact with and other titratable groups in the protein as well as permanent charges (e.g. ions) and dipoles in the protein. All of these effects can alter the pKa value of the amino acid side chain from its solution pKa. An amino acid residue to be substituted, deleted or modified may also be selected based upon the whole-protein pKa of the amino acid residue in the wild type protein. The whole-protein pKa of an amino acid residue within a folded protein may be estimated by a variety of techniques. Some methods are based on solutions to the Poisson-Boltzmann equation, often referred to as FDPB-based methods (for "finite difference Poisson-Boltzman). FDPB-based methods calculate the change in the pKa value of an amino acid side chain when that side chain is moved from a hypothetical fully solvated state to its position in the protein, using knowledge of the pKa values of amino acid side chains in their fully solvated states combined with theoretical methods that calculate the effect of the protein interior on a pKa value. Publically available programs to calculate the estimated pKa values of amino acid side chains in a protein using FDPB methods include H++, available at the H++ server at Virginia Polytechnic Institute (Gordon et al., Nucleic Acids Research 33: W368-W371 (2005); Anandakrishnan and Onufriev, Journal of Computational Biology 15: 165-184 (2008)); Karlsberg+ (Kieseritzky and Knapp, Proteins: Structure, Function, and Bioinformatics 71:1335-1348 (2008)); Rabenstein and Knapp, Biophysical Journal 80(3):1141-1150 (2001)); MCCE (Song and Gunner, J. Comp. Chem epub March 2009; Georgescu et al., Biophys J. 83, 1731-1748 (2002); and the pKD webserver (Tynan-Connolly and Nielsen, Nucleic Acid Research 34: W48-W51 (2006); Tynan-Connolly and Nielsen, Protein Science 16: 239-249 (2007)).

An alternative method is used by PropKa, a software program for calculation of whole-protein pKa values available at the PROPKA Web Interface at the University of Copenhagen (Li et al., Proteins 61: 704-721 (2005); Bas et al., Proteins 73: 765-783 (2008). The PropKa program for rapid prediction of pKa values is based upon a set of empirical rules relating the protein structure to the pKa values of ionizable residues.

Molecular dynamics methods of calculating pKa values involve computationally measuring the free energy difference between the protonated and deprotonated forms of the molecule. Molecular dynamics is typically a much more computationally expensive way to predict pKa's than using the Poisson-Boltzmann equation. In recent years, constant pH molecular dynamics methods have been developed based on a microscopic description of the protein. (Wallace and Shen, Methods in Enzymology 466: 455-475 (2009)).

The publicly available programs and webservers for pKa calculations of amino acid side chains typically require a three-dimensional structure of the protein to be analyzed in PDB (Protein Data Bank) format. These structures can be downloaded from sites such as PDBsum. (Laskowski, Nucleic Acids Res., 37, D355-D359 (2009)). The programs will return a listing of the calculated pKa values for the titratable amino acid side chains of the protein, as well as the N-terminal and C-terminal groups. As an example, Tables 2 and 3 show the calculated pKas for amino acids within Bst DNA polymerase. Column 1 shows the amino acid residue, with numbering based upon that of SEQ ID NO:1; column 2 shows the calculated pKa of the side chain. The values shown in Table 2 were determined using PropKa, while the values in Table 3 were determined using H++. Since these programs use different algorithms, they may return different values for the pKas of individual amino acid resides. In some cases, it may be useful to compare results from both programs as confirmation that a given amino acid residue has a pKa in a pH range of interest.

in some embodiments, the modifying can include substituting at least one amino acid residue having an undesirable pKa (e.g., a pKa falling within the range of typical reaction conditions for the desired application) and likely to be on the protein surface (e.g., at least 30% solvent exposed, more typically at least 50% solvent exposed) with an amino acid having a more desirable pKa (e.g., a pKa falling outside the range of typical reaction conditions).

In some embodiments, the modifying can include substituting at least one amino acid residue having a pKa of between about 4.0 and about 10.0 with an amino acid residue having a pKa that is greater than about 10.0 or less than about 4.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, the modifying can include substituting at least one amino acid residue having a pKa within the range of about 6.0 to about 8.0 with another amino acid residue. The pKa can optionally be the solution pKa or the whole-protein pKa of the amino acid residue.

In some embodiments, the modifying can include substituting at least one amino acid residue having a pKa of between about 6.0 and about 8.0 with an amino acid residue having a pKa that is greater than about 8.0 or less than about 6.0. In some embodiments, the amino acid to be substituted is His, Glu, Asp, Tyr or Lys.

In some embodiments, the protein is a polymerase and the substituting can include replacement of any amino acid residue of the polymerase that is not an invariant or conserved residue with another residue. Further descriptions of amino acid residues that are conserved or invariant amongst polymerases are provided herein.

In some embodiments, the modifying can include introducing at least one conservative substitution into the protein, in which at least one property such as the size, shape or charge of the amino acid is conserved. A "conservative amino acid substitution" refers to substitution of a structurally and/or functionally similar amino acid that may be made without not substantially altering the function of a protein. An example of conservative substitution is the exchange of an amino acid in one of the following groups for another amino acid of the same group (U.S. Pat. No. 5,767,063; Kyte and Doolittle, J. Mol. Biol. 157: 105-132 (1982)):

(1) Hydrophobic: Norleucine, Ile, Val, Leu, Phe, Cys, Met;
(2) Neutral hydrophilic: Cys, Ser, Thr;
(3) Acidic: Asp; Glu;
(4) Basic: Asn, Gln, His, Lys, Arg;
(5) Residues that influence chain orientation: Gly, Pro;
(6) Aromatic: Trp; Tyr; Phe;
(7) Small amino acids: Gly, Ala, Ser.

For example, substitutions can be made by changing, e.g., Val to Leu; Ser to Thr; or Asp to Glu. Other substitutions can also be considered conservative, depending on the environment of the particular amino acid and its role in the three-dimensional structure of the protein. For example, when it is desired to alter the pKa of an amino acid side chain while retaining the size and structure of the side chain, Glu may be substituted by Gln, and Asp may be substituted by Asn.

In some embodiments, the amino acid residues selected for modification (e.g., replacement with another amino acid residue) are selected from the group consisting of: His, Glu, Asp, Cys, Lys and Tyr. In some embodiments, the amino acid residues selected for modification include His and Glu residues. These amino acid residues typically have pKa values (even in the whole-protein context) of between about pH 6 to about pH 8, and therefore possess high buffering capacities under standard physiological conditions and standard in vitro protein assay conditions. For example, His typically has a solution pKa (i.e., side chain pKa) of about 6.1-6.5 under standard physiological conditions (e.g., pH conditions of from about pH 6.0 to about pH 9.0), while that of Glutamine is about 4.1-4.5, and that of Cysteine is about 8.0. Replacement of these residues with amino acid residues that are typically non-buffering under standard protein assay conditions can be advantageous in applications in which it is desirable to achieve low-buffering conditions, e.g., ion-based reactions.

In some embodiments, the at least one conservative amino acid substitution is selected from the group consisting of His to Arg, Glu to Gln, Asp to Asn, Lys to Arg, and Tyr to Phe.

In some embodiments, at least one of the one or more amino acid modifications includes a substitution of an amino acid with an alanine residue. Substitution or replacement of amino acid residues having high buffering capacities with alanine residues can be advantageous in applications in which it is desirable to reduce the buffering capacity of the protein. Introduction of alanine residues in lieu of high-buffering residues is likely to reduce the overall buffering capacity of the protein because alanine residues typically are small, interfere minimally with protein structure, and typically have low buffering capacity under standard physiological conditions (or standard in vitro protein assay conditions) because they are usually uncharged at physiological pHs. Alanine residues are therefore unlikely to possess significant buffering capacity under the operating conditions of interest.

In some embodiments, at least one of the one or more amino acid modifications includes a deletion of an amino acid. In some embodiments, at least one of the one or more deleted amino acids includes an amino acid residue having a pKa of between about 4.0 and about 10.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more deleted amino acids is an amino acid residue having a pKa within the range of about 6.0 to about 8.0 with another amino acid residue. In some embodiments, the deleted amino acid is His, Glu, Asp, Tyr or Lys.

An amino acid residue having an undesirable pKa may also be chemically modified so as to remove the buffering capacity of its titratable group. These modifications may include, for example, acylation or alkylation of cysteine sulfhydryl groups, acylation of tyrosine, derivatization of carboxylate groups on aspartic acid or glutamic acid through the use of amide bond forming agents or through active ester or reactive carbonyl intermediates, and acylation or alkylation of amine groups of histidine, lysine arginine, or the N-terminal amine group, using conventional reagents such as those disclosed in Hermanson (Bioconjugate Techniques, Academic Press, London, 2008). An N-terminal amine may be acylated using N-succinimidyl-derived reagents, to attach acetate groups, polyethylene glycol groups, biotins, or the like.

In some embodiments, after candidate protein is modified in the selected fashion, it may be synthesized, and tested for altered buffering capacity. For example, testing for reduced or increased buffering capacity in a desired range, such as pH 7-9, may be accomplished by performing a conventional pH titration on a known quantity of the candidate protein and determining the characteristic of the titration curve in the desired pH range; namely, in the pH 7-9 range, small additions of hydroxide ion (or hydrogen ion) should correspond to large changes in measured pH.

In some embodiments, the buffering capacity can be evaluated by comparing the performance of a modified protein with a reference protein (e.g., a reference lacking at least one modification of the modified protein, or the unmodified counterpart of the modified protein, or the wild-type version of the modified protein) in an ion-based sequencing reaction. In some embodiments, ion-based sequencing can be performed using the Ion Torrent PGM™ sequencer (Life Technologies). In some embodiments, sequencing can be performed according to the user protocols supplied with the PGM™ sequencer. Example 7 provides one exemplary protocol for ion-based sequencing using the Ion Torrent PGM™ sequencer, and also describes some of the sequencing performance metrics that can be used to evaluate buffering capacity of the modified protein in a sequencing reaction. In some embodiments, the number of 50Q17 reads can be plotted against the number of keypass reads, and the results obtained using the modified and reference proteins can be compared to determine whether the modified protein has altered buffering capacity relative to the reference protein. In some embodiments, the number of 50Q17 reads can be plotted against the number of keypass reads, and the results obtained using the modified and reference proteins can be compared to determine whether the modified protein has altered buffering capacity relative to the reference protein. In some embodiments, the number of carryforwards can be plotted against the number of keypass reads, and the results obtained using the modified and reference proteins can be compared to determine whether the modified protein has altered buffering capacity relative to the reference protein.

In some embodiments, measuring and comparing the performance of a modified protein with that of a reference protein can provide a useful tool for screening modified proteins for altered buffering capacities. For example, in some embodiments, the disclosure relates to a method for screening modified proteins for altered buffering capacities, comprising: obtaining a candidate protein to be modified; introducing one or more modifications into the candidate protein, thereby producing a modified protein; using the modified protein in an ion-based sequencing reaction and measuring the modified protein's performance in the ion-based sequencing system according to a first parameter; measuring the performance of a reference protein in the ion-based sequencing system according to the first parameter; and comparing the performances of the modified and reference proteins in the ion-based sequencing system according to the first parameter, thereby determining whether the modified protein has altered buffering capacity relative to the reference protein. In some embodiments, the reference protein is a protein lacking at least one modification of the modified protein. In some embodiments, the reference protein is the unmodified counterpart of the modified protein. In some embodiments, the reference protein is the wild-type version of the modified protein. In some embodiments, the first parameter is the total number of 50Q17 reads obtained from a single sequencing run. In some embodiments, the first parameter is the total number of 100Q17 reads obtained from a single sequencing run. In some embodiments, the 50Q17 reads or the 100Q17 reads obtained using the modified and reference proteins can be plotted against the keypass reads, and the results can be compared.

In some embodiments, the modified protein is a polymerase and the reference protein is a wild-type version of the polymerase, or is an unmodified counterpart of the polymerase.

In some embodiments, the modified protein comprises one or more chemical amino acid modifications that reduce the buffering capacity of the protein relative to the corresponding wild-type protein within the range of about pH 4 to about pH 10, about pH 5.5 to about pH 9.5, or about pH 7 to about pH 9. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In further embodiments, the amine-reactive reagent includes an acylating agent or an activated ester.

In some embodiments, at least one of the one or more amino acid substitutions, deletions or chemical modifications includes a substitution of an amino acid residue that is at least 20%, at least 25%, at least 30%, at least 35% or at least 40% solvent exposed in the corresponding wild-type protein with another amino acid residue.

In some embodiments, the characteristic activity of the modified protein is at least about 40%, 50%, 60%, 70%, 80% or 90% that of the corresponding wild type protein. In order to retain the characteristic activity of the modified protein, the sites of amino acid substitutions, deletions or modifications are chosen so as to avoid altering residues known to be important for protein function, such as residues that are highly conserved across members of a protein family, or known catalytic site residues.

In various embodiments, the modified protein has DNA- or RNA-binding activity. In various embodiments, the protein is selected from the group consisting of DNA polymerases, helicases, ligases, nucleases, single stranded DNA binding proteins and polymerase accessory proteins. These modified proteins may comprise any combination of amino acid substitutions, deletions or chemical modifications.

In some embodiments, the one or more amino acid substitutions substantially reduce the buffering capacity of said protein within the range of about pH 7 to pH 9. In some embodiments, at least one of the one or more amino acid substitution is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the protein is a DNA polymerase. In some embodiments, the disclosure relates generally to an isolated DNA polymerase comprising one or more conservative amino acid substitutions that substantially reduce its buffering capacity relative to the corresponding wild-type protein within the range of about pH 7 to about pH 9. In some embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of an A family DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 and its priority documents.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. As used herein, a "Bst DNA polymerase" may refer to a full length protein or to a Bst DNA polymerase large fragment which retains the polymerase and proofreading domains while lacking the 5' to 3' exonuclease domain.

In some embodiments, the one or more conservative amino acid substitutions are of one or more amino acid residues shown in Table 2 or Table 3. Tables 2 and 3 show the calculated pKas for amino acids within Bst DNA polymerase. Column 1 shows the amino acid residue, with numbering based upon that of SEQ ID NO:1; column 2 shows the calculated pKa of the side chain; and column 3 indicates whether the amino acid residue is on the surface of the protein (S) or is buried (B). The values shown in Table 2 were determined using PropKa, while the values in Table 3 were determined using H++. In some embodiments, the one or more conservative amino acid substitutions are of amino acid residues having a pKa of about 4.0 to about 10.0 as determined by both algorithms.

In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the Bst DNA polymerase comprises one or more conservative amino acid substitutions, wherein the one or more amino acid substitutions includes a substitution of alanine at position 2 with Met, Asn, Gln, Leu, Ile, Phe, or Trp, the numbering of amino acid residues being in accordance with that of SEQ ID NO: 1.

In some embodiments, at least one of the one or more amino acid modifications in the Bst DNA polymerase includes a substitution of an amino acid residue with an alanine residue. In some embodiments, the Bst DNA polymerase comprises the substitution H528A.

In some embodiments, the disclosure relates generally to an isolated Bst DNA polymerase comprising an amino acid sequence selected from the group consisting of SEQ ID NO: 2, SEQ ID NO: 3 and SEQ ID NO: 4, or a variant thereof having one or more conservative amino acid substitutions. The initial methionine residue of these amino acid sequences is not derived from the native Bst polymerase, but is present to facilitate the production of the large fragment. Thus in some embodiments, the isolated Bst Polymerase comprises an amino acid sequence of any one of SEQ ID NO: 2, SEQ ID NO: 3 and SEQ ID NO: 4, or any variant as described herein, wherein the protein lacks the N-terminal methionine residue.

In some embodiments, the Bst DNA polymerase comprises the amino acid sequence of SEQ ID NO: 2. In some embodiments, the disclosure relates generally to an isolated variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the disclosure relates generally to a Bst DNA polymerase comprising the amino acid sequence of SEQ ID NO: 3. In some embodiments, the disclosure relates generally to an isolated variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the disclosure relates generally to a Bst DNA polymerase comprising the amino acid sequence of SEQ ID NO: 4. In other embodiments, the disclosure relates generally to an isolated variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more amino acid substitutions, deletions or mutations as described above. In some embodiments, the Therminator™ DNA polymerase comprises one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine.

In some embodiments, the one or more conservative amino acid substitutions are of one or more amino acid residues shown in Table 5. Table 5 shows the calculated pKas for amino acids within Therminator™ DNA polymerase as determined using PropKa. Column 1 shows the amino acid residue, with numbering based upon that of SEQ ID NO: 5; while column 2 shows the calculated pKa of the side chain.

In some embodiments, the DNA polymerase is a KOD DNA polymerase comprising one or more amino acid substitutions, deletions or mutations as described above. In some embodiments, the KOD DNA polymerase comprises one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6. Table 6 shows the calculated pKas for amino acids within KOD DNA polymerase as determined using PropKa. Column 1 shows the amino acid residue, with numbering based upon that of SEQ ID NO: 6; while column 2 shows the calculated pKa of the side chain. Optionally, the KOD polymerase includes one or more mutations reducing an exonuclease activity (for example, a 3'→5'exonuclease activity) of the protein.

In some embodiments, the DNA polymerase is a B103 DNA polymerase comprising one or more amino acid substitutions, deletions or mutations as described above. A B103 DNA polymerase may include any of the variant B103 polymerases, or biologically active fragments thereof, as disclosed in U.S. Patent Publication No. 20110014612, which is incorporated by reference herein.

In some embodiments, the B103 polymerase has the amino acid sequence of SEQ ID NO: 7, further comprising amino acid substitutions at positions 383 and 384, wherein the numbering is relative to the amino acid sequence of SEQ ID NO: 7. In some embodiments, the polymerase comprises the amino acid substitutions F383L and D384N, wherein the numbering is relative to the amino acid sequence of SEQ ID NO: 7.

In some embodiments, the B103 polymerase has the amino acid sequence of SEQ ID NO: 8.

```
                                                            (SEQ ID NO: 8)
  1  mprkmfscdf etttklddcr vwaygymeig nldnykigns ldefmqwvme iqadlyfhnl 61  kfdgafivnw lehhgfkwsn eglpntynti iskmgqwymi dicfgykgkr klhtviydsl 121  kklpfpvkki akdfqlpllk gdidyhaerp vgheitpeey eyikndieii araldiqfkg 181  gldrmtagsd slkgfkdils tkkfnkvfpk lslpmdkeir rayrggftwl ndkykekeig 241  egmvfdvnsl ypsqmysrpl pygapivfqg kyekdegypl yiqrirfefe lkegyiptiq 301  ikknpffkgn eylknsgaep velyltnvdl eliqehyemy nveyidgfkf rektglfkef 361  idkwtyvkth ekgakkqlak lmfdslygkf asnpdvtgkv pylkedgslg frvgdeeykd 421  pvytpmgvfi tawarfttit aaqacydrii ycdtdsihlt gtevpeiikd ivdpkklgyw 481  ahestfkrak ylrqktyiqd iyakevdgkl iecspdeatt tkfsvkcagm tdtikkkvtf 541  dnfrvgfsst gkpkpvqvng gvvlvdsvft ik
```

In some embodiments, the B103 polymerase comprises an amino acid sequence that is at least 80%, 85%, 90%, 95%, 97%, 98% or 99% identical to the amino acid sequence of SEQ ID NO: 8, or any biologically active fragment thereof. Typically, a polymerase having the amino acid sequence of SEQ ID NO: 8 will exhibit increased polymerase activity (e.g., primer extension activity) relative to the polymerase having the amino acid sequence of SEQ ID NO: 7.

In some embodiments, the B103-type polymerase comprises one or more modifications resulting in altered exonuclease activity (for example 3' to 5' exonuclease activity) as compared to a reference polymerase. In some embodiments, the modification comprises an amino acid substitution, for example the amino acid substitution D166A. In some embodiments, the modified B103-type polymerase lacks 3' to 5' exonuclease activity, or lacks 5' to 3' exonuclease activity, or both. Mutations that reduce or eliminate 3' to 5' exonuclease activity have been described, for example, in Phi-29 polymerase at various residues. See, e.g., de Vega et al., EMBO J., 15(5):1182-1192 (1996); Soengas et al., EMBO J., 11(11):4227-4237 (1992); Blanco et al., U.S. Pat. Nos. 5,001,050, 5,198,543 and 5,576,204.

In some embodiments, the B103 polymerase comprises an amino acid sequence that is at least 70%, 75%, 85%, 90%, 95% or 99% identical to any one of the amino acid sequences SEQ ID NO: 7, SEQ ID NO: 8 and SEQ ID NO: 9, or to any biologically active fragment thereof, and further comprises one or more amino acid substitutions, additions or deletions at one or more positions selected from the group consisting of: 2, 9, 11, 12, 58, 59, 63, 162, 166, 377 and 385, wherein the numbering is relative to SEQ ID NO: 7. In some embodiments, this polymerase can exhibit reduced exonuclease activity relative to an unmodified counterpart.

In some embodiments, the B103 polymerase comprises an amino acid sequence that is at least 70%, 75%, 85%, 90%, 95% or 99% identical to any one of the amino acid sequences SEQ ID NO: 7 or SEQ ID NO: 8 or to any biologically active fragment thereof, and further comprises the amino acid mutation D166A, wherein the numbering is relative to SEQ ID NO: 7. In some embodiments, this modified polymerase can exhibit reduced 3' to 5' exonuclease activity relative to a reference polymerase having the amino acid sequence of SEQ ID NO: 7.

In some embodiments, the B103 DNA polymerase comprises an amino acid sequence that is at least 70%, 75%, 85%, 90%, 95% or 99% identical to any one of the amino acid sequences SEQ ID NO: 7, SEQ ID NO: 8 and SEQ ID NO: 9, or to any biologically active fragment thereof, and further comprises one or more amino acid substitutions selected from the group consisting of: D9A, E11A, E11I, T12I. H58R, N59D, D63A, Y162F, Y162C, D166A, Q377A and S385G, wherein the numbering is relative to SEQ ID NO: 7. In some embodiments, this modified polymerase can exhibit reduced exonuclease activity relative to an unmodified counterpart.

In some embodiments, the B103 DNA polymerase comprises an amino acid sequence that is at least 70%, 75%, 85%, 90%, 95% or 99% identical to any one of the amino acid sequences SEQ ID NO: 7, SEQ ID NO: 8 and SEQ ID NO: 9 or to any biologically active fragment thereof, and further comprises one or more amino acid substitutions selected from the group consisting of: D9A, E11A, E11I, T12I, H58R, N59D, D63A, Y162F, Y162C, Q377A and S385G, wherein the numbering is relative to SEQ ID NO: 7. Typically, this modified polymerase can exhibit reduced 3' to 5' exonuclease activity relative to an unmodified counterpart.

In some embodiments, the B103 DNA polymerase comprises an amino acid sequence that is at least 85%, 90%, 95% or 99% identical to the amino acid sequence of SEQ ID NO: 7 and further comprises an amino acid substitution wherein the amino acid residue at position 9 is replaced with an alanine ("A") residue, wherein the numbering is relative to the amino acid sequence of SEQ ID NO: 7.

In some embodiments, the B103 DNA polymerase comprises an amino acid sequence that is at least 85%, 90%, 95% or 99% identical to the amino acid sequence of SEQ ID NO: 7 and further comprises one or more of the amino acid substitutions D9A, E11A, T12I, H58R, N59D, D63A, D166A, Q377A, S385G, or any combination thereof, wherein the numbering is relative to the amino acid sequence of SEQ ID NO: 7. In some embodiments, the B103 DNA polymerase comprises any one, two, three, four, five or all of these mutations. In some embodiments, the B103 DNA polymerase comprises the amino acid substitutions D9A and D63A. In some embodiments, the B103 DNA polymerase comprises the amino acid substitutions N59D and T12I. Typically, this polymerase will exhibit reduced 3' to 5' exonuclease activity relative to an unmodified counterpart.

In some embodiments, the B103 DNA polymerase comprises an amino acid sequence that is at least 85%, 90%, 95% or 99% identical to the amino acid sequence of SEQ ID NO: 8, and comprises any one, two, three or more of the mutations described herein.

Optionally, the modification(s) reducing 3' to 5' exonuclease activity can be combined with additional modification (s) that increase polymerase activity. Modifications increasing polymerase activity include, for example, the amino acid substitutions F383L and D384N.

In some embodiments, the B103 DNA polymerase comprises the amino acid sequence of SEQ ID NO: 7 and further comprises the amino acid substitution D166A, which reduces the 3' to 5' exonuclease activity, in combination with the amino acid substitutions F383L and D384N, which increase the polymerase activity of the substituted polymerase, relative to the unmodified protein having the amino acid sequence of SEQ ID NO: 8. The amino acid sequence of this triple mutant polymerase is the amino acid sequence of SEQ ID NO: 9, below:

```
                                                         (SEQ ID NO: 9)
  1  mprkmfscdf etttkldder vwaygymeig nldnykigns ldefmqwvme iqadlyfhnl
 61  kfdgafivnw lehhgfkwsn eglpntynti iskmgqwymi dicfgykgkr klhtviydsl
121  kklpfpvkki akdfqlpllk gdidyhaerp vgheitpeey eyiknaieii araldiqfkg
181  gldrmtagsd slkgfkdils tkkfnkvfpk lslpmdkeir rayrggftwl ndkykekeig
241  egmvfdvnsl ypsqmysrpl pygapivfqg kyekdegypl yiqrirfefe lkegyiptiq
301  ikknpffkgn eylknsgaep velyltnvdl eliqehyemy nveyidgfkf rektglfkef
361  idkwtyvkth ekgakkqlak lmlnslygkf asnpdvtgkv pylkedgslg frvgdeeykd
421  pvytpmgvfi tawarfttit aaqacydrii ycdtdsihlt gtevpeiikd ivdpkklgyw
481  ahestfkrak ylrqktyiqd iyakevdgkl iecspdeatt tkfsvkcagm tdtikkkvtf
541  dnfrvgfsst gkpkpvqvng gvvlvdsvft ik
```

In some embodiments, the modified polymerase comprises an amino acid sequence that is at least 70%, 75%, 80%, 85%, 90%, 95%, 97%, 98% or 99% identical to the amino acid sequence of SEQ ID NO: 9, or any biologically active fragment thereof. Typically, the modified polymerase of SEQ ID NO: 9 will exhibit reduced exonuclease activity relative to a reference polymerase comprising the amino acid sequence of SEQ ID NO: 7 or SEQ ID NO: 8.

In some embodiments, the disclosure relates generally to a B103 DNA polymerase, including any of the variants described above, wherein the B103 DNA polymerase comprises one or more conservative amino acid substitutions that substantially reduce its buffering capacity relative to the corresponding unmodified protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7. Table 7 shows the calculated pKas for amino acids within Therminator™ DNA polymerase as determined using PropKa. Column 1 shows the amino acid residue, with numbering based upon that of SEQ ID NO: 7; while column 2 shows the calculated pKa of the side chain.

In some embodiments, the modified polymerase retains polymerase activity. In various embodiments, the polymerase activity of a modified DNA polymerase is at least about 40%, 50%, 60%, 70%, 80% or 90% that of the corresponding wild type protein. As used herein, the term "polymerase activity" and its variants, when used in reference to a given polymerase, comprises any in vivo or in vitro enzymatic activity characteristic of a given polymerase that relates to catalyzing the polymerization of nucleotides into a nucleic acid strand, e.g., nucleotide incorporation activity (typically measured as primer extension activity in a primer extension assay), and the like. Typically, but not necessarily such nucleotide polymerization occurs in a template-dependent fashion. In addition to such polymerase activity, the polymerase can typically possess other enzymatic activities, for example, 3' to 5' exonuclease activity, 5' to 3' exonuclease activity, and the like.

In some embodiments, the amount of nucleotide incorporation activity (or primer extension activity) exhibited by the polymerase can be quantified as the total number of nucleotides incorporated (as measured by, e.g., radiometric or other suitable assay) by a unit amount of polymerase (in moles) per unit time (seconds) under a particular set of reaction conditions. The nucleotide incorporation activity (or primer extension activity) can be measured using any suitable assay that provides a quantitative indication of the amount of extension product obtained using defined reaction conditions comprising a known concentration of polymerase. Regardless of which assay is used, differences in nucleotide incorporation activity (or primer extension activity) between two samples, when obtained using identical reaction conditions, can be evaluated by simply comparing levels of observed nucleotide incorporation activity (or primer extension activity) obtained from each sample. Optionally, the observed nucleotide incorporation activity (or primer extension activity) can normalized for amount of polymerase by dividing the amount of incorporated radioactivity by the polymerase concentration in the reaction mixture, to allow comparison between reactions containing different polymerase concentrations.

In one exemplary embodiment, the nucleotide incorporation activity (or primer extension activity) of a polymerase can be measured using a radiometric assay that measures incorporation of a radioactively labeled nucleotide into acid-insoluble material in a polymerase reaction. The amount of incorporated radioactivity indicates the total number of nucleotides incorporated. See, e.g., Wu et al., Gene Biotechnology, 2nd Ed., CRC Press; Sambrook, J., Fritsch, E F, and Maniatis, T. (1989) Molecular Cloning A Laboratory Manual, 2nd ed., Cold Spring Harbor Laboratory Press, Cold Spring Harbor, N.Y.

In another exemplary embodiment, levels of nucleotide incorporation activity (or primer extension activity) in a sample can be measured by monitoring the fluorescence intensity change over time during extension of a fluorescein-labeled hairpin oligonucleotide.

In another exemplary embodiment, the nucleotide incorporation activity (or primer extension activity) of a given polymerase can be quantified by quantifying the amount of pyrophosphate liberated after performing nucleotide incorporation (e.g., primer extension) under standard tolerance assay conditions for 5 minutes.

Various examples of such assays for polymerase activity can be found, for example, in U.S. application Ser. No. 12/748,359, now published as U.S. Publication No. 20110014612.

In order to retain the characteristic activity of the modified protein, the sites of amino acid substitutions, deletions or chemical modifications are chosen so as to avoid altering residues known to be important for protein function, such as residues that are highly conserved across members of the particular family of DNA polymerases to which the modified protein belongs, or known catalytic site residues involved in polymerase activity.

In some embodiments, the modified polymerase that retains polymerase activity is a B103 DNA polymerase Amino acid residues that affect the polymerase or exonuclease activity of the B103 DNA polymerase have been described in detail above.

In some embodiments, the modified polymerase that retains polymerase activity is a Bst DNA polymerase. The amino acid sequence of the large fragment of the Bst DNA polymerase protein is shown in SEQ ID NO: 1:

```
MAKMAFTLAD RVTEEMLADK AALVVEVVEE NYHDAPIVGI AVVNEHGRFF LRPETALADP    60

QFVAWLGDET KKKSMFDSKR AAVALKWKGI ELCGVSFDLL LAAYLLDPAQ GVDDVAAAAK   120

MKQYEAVRPD EAVYGKGAKR AVPDEPVLAE HLVRKAAAIW ELERPFLDEL RRNEQDRLLV   180

ELEQPLSSIL AEMEFAGVKV DTKRLEQMGK ELAEQLGTVE QRIYELAGQE FNINSPKQLG   240

VILFEKLQLP VLKKTKTGYS TSADVLEKLA PYHEIVENIL HYRQLGKLQS TYIEGLLKVV   300

RPDTKKVHTI FNQALTQTGR LSSTEPNLQN IPIRLEEGRK IRQAFVPSES DWLIFAADYS   360

QIELRVLAHI AEDDNLMEAF RRDLDIHTKT AMDIFQVSED EVTPNMRRQA KAVNFGIVYG   420

ISDYGLAQNL NISRKEAAEF IERYFESFPG VKRYMENIVQ EAKQKGYVTT LLHRRRYLPD   480

ITSRNFNVRS FAERMAMNTP IQGSAADIIK KAMIDLNARL KEERLQAHLL LQVHDELILE   540

APKEEMERLC RLVPEVMEQA VTLRVPLKVD YHYGSTWYDA K
```

SEQ ID NO: 1 contains the DNA polymerase motifs A, B, and C (Delahue, supra) at residues 358-363, 411-420 and 533-536, respectively, as shown in FIG. 1. The motifs are underlined and highlighted, and the invariant residues within each motif are indicated in bold. Thus in order to retain the polymerase activity of a modified Bst polymerase, any substitutions, deletions or chemical modifications will be made to amino acid residues that are not highly conserved within motifs A, B or C, such as the invariant aspartic acid residues D358 and D535 required for polymerase activity.

In some embodiments, the modified Bst DNA polymerase retains proofreading exonuclease activity. In various embodiments, the proofreading exonuclease activity of a modified Bst DNA polymerase is at least about 40%, 50%, 60%, 70%, 80% or 90% that of the corresponding wild type protein. In order to retain the proofreading exonuclease activity of a modified Bst DNA polymerase, the skilled artisan will understand that any substitutions, deletions or chemical modifications should be made to amino acid residues that are not highly conserved within the Exo I, Exo II and Exo III motifs.

In some embodiments, the disclosure relates generally to an isolated protein comprising one or more amino acid substitutions, deletions, or chemical modifications that reduce the buffering capacity of said protein relative to the corresponding wild-type protein within the range of about pH 4 to about pH 10, wherein the one or more amino acid substitutions, deletions or chemical modifications substantially reduce the average number of sequencing errors obtained from an ion-based sequencing reaction using the modified protein, relative to the number of sequencing errors obtained from an ion-based sequencing reaction using the corresponding wild-type (unmodified) protein.

The sequencing error rate will in part depend upon the fidelity of the polymerase used in the sequencing reaction. The fidelity of a polymerase depends in part upon the tendency of the polymerase to incorporate incorrect nucleotides, as well as the presence of an integral 3' to 5' exonuclease activity, which can increase fidelity by excising misincorporated nucleotides. It is known that a conserved residue in motif A of DNA polymerases (E for family A members and Y for family B members), as well as residues which interact with this conserved residue, play an important role in incorporation of the correct nucleotide (Parsell, supra; Minnick, supra). Conserved motifs involved in 3' to 5' exonuclease activity are also known, as discussed above. It is also known in the art that some polymerases have improved fidelity relative to others. Residues that may play a role in either nucleotide incorporation or 3' to 5' exonuclease activity may be determined by a review of the relevant motifs in a polymerase, or by comparison to polymerases having improved fidelity. Thus in some embodiments, the disclosure relates generally to a modified DNA polymerase, wherein one or more of the modifications to the polymerase affect either nucleotide incorporation or 3' to 5' exonuclease activity.

In some embodiments, the disclosure relates generally to an isolated protein comprising one or more amino acid substitutions, deletions or chemical modifications that reduce the buffering capacity of said protein relative to the corresponding wild-type protein within the range of about pH 4 to about pH 10, wherein the one or more amino acid substitutions, deletions or chemical modifications increase the average length of sequencing reads having at least 90% accuracy obtained from an ion-based sequencing reaction using the modified protein, relative to average length of sequencing reads having 90% accuracy obtained from an ion-based sequencing reaction using the corresponding wild-type (unmodified) protein.

The length of sequencing reads depends in part upon the processivity of the polymerase used in the sequencing reaction. The processivity of a polymerase is a measure of the average number of nucleotides added by the polymerase per association/disassociation with the template.

It is known in the art that some polymerases have improved processivity relative to others. Residues that may play a role in processivity may be determined by comparison to polymerases having improved processivity. Thus in some embodiments, the disclosure relates generally to a modified DNA polymerase, wherein one or more of the modifications to the polymerase affect processivity.

It is also known in the art that accessory proteins, including, for example, sliding clamp proteins or single stranded DNA binding proteins (SSBs), can improve the processivity of a DNA polymerase. SSBs are also used in the art to improve fidelity of DNA polymerases. Thus in some embodiments, the disclosure relates generally to a modified accessory protein or SSB, wherein the modified protein provides increased improvements to the processivity and/or fidelity of a polymerase used in a sequencing reaction, as compared to an unmodified accessory protein or SSB.

In some embodiments, the isolated protein comprising one or more amino acid substitutions that reduce the buffering capacity of said protein relative to the corresponding wild-type protein within the range of about pH 4 to about pH 10 is a single stranded DNA binding protein (SSB).

In some embodiments, the SSB comprises one or more conservative amino acid substitutions that substantially reduce its buffering capacity within the range of pH 7 to pH 9. In further embodiments, the one or more conservative amino acid substitutions are selected from the group consisting of histidine to arginine, glutamic acid to glutamine, aspartic acid to asparagine, lysine to arginine, and tyrosine to phenylalanine. In some embodiments, the SSB is E. coli SSB. In further embodiments, the one or more conservative amino acid substitutions are of one or more amino acid residues shown in Table 4. Tables 2 and 3 show the calculated pKas for amino acids within E. coli SSB. Column 1 shows the amino acid residue, with numbering based upon that of SEQ ID NO:1; column 2 shows the calculated pKa of the side chain. In some embodiments, the SSB comprises the amino acid substitution K7R.

In some embodiments, any of the isolated proteins described herein further include an affinity tag, a label, a chemical moiety, a radionuclide, an enzyme, a fluorescent marker, a chemiluminescent marker, or a combination thereof.

In some embodiments, the isolated protein is coupled to a polymer, a support, or a sensor. Polymers may include, for example, polyethylene glycol, PEA, a dextran, an acrylamide, or a cellulose (e.g., methyl cellulose). Supports may include, for example, beads or other solid surfaces such as the surface of a reaction chamber, microwell or sensor. Sensors may include, for example, a FET. In some embodiments, the sensor is a chemFET. In some embodiments, the sensor is an ISFET.

In some embodiments, the disclosure relates generally to a method for incorporating at least one nucleotide into a primer, comprising: contacting a nucleic acid duplex including a template nucleic acid and a primer with a modified polymerase according to the disclosure in the presence of one or more nucleotides, and incorporating at least one nucleotide into the primer in a template-dependent fashion using the polymerase. The modified polymerase may be any of the polymerases having any of the modifications disclosed above, including one or more amino acid substitutions, deletions and chemical modifications.

In some embodiments of the method, the polymerase comprises one or more amino acid substitutions that reduce the buffering capacity of said protein relative to the corresponding wild-type protein within the range of about pH 4 to about pH 10. In some embodiments, the one or more amino acid substitutions reduce the buffering capacity of the polymerase relative to the corresponding wild-type polymerase within the range of about pH 7 to about pH 9, or of about pH 6 to about pH 8.

In some embodiments, the one or more amino acid substitutions substantially reduce the buffering capacity of the polymerase within the range of about pH 7 to pH 9. In embodiments, at least one of the one or more amino acid substitution is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In various embodiments of the method, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of: Bst polymerase, Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator™ polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is derived from phage B103 polymerase, including, for example, the variants disclosed in U.S. Patent Publication No. 20110014612 which is incorporated by reference herein.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In some embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments of the method, the DNA polymerase is a Bst DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 2 or Table 3. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the Bst DNA polymerase comprises one or more conservative amino acid substitutions, wherein the one or more amino acid substitutions includes a substitution of alanine at position 2 with Met, Asn, Gln, Leu, Ile, Phe, or Trp, the numbering of amino acid residues being in accordance with that of SEQ ID NO: 1.

In some embodiments of the method, the polymerase is a Bst DNA polymerase comprising an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the disclosure relates generally to an isolated variant of a protein comprising the amino acid sequence shown in SEQ ID NO: 2, wherein the variant comprises an amino acid sequence that is at least 95% identical to SEQ ID NO: 2.

In some embodiments of the method, the polymerase is a Bst DNA polymerase comprising the amino acid sequence of SEQ ID NO: 3. In some embodiments, the disclosure relates generally to an isolated variant of a protein comprising the amino acid sequence shown in SEQ ID NO: 3, wherein the variant comprises an amino acid sequence that is at least 95% identical to SEQ ID NO: 3.

In some embodiments of the method, the polymerase is a Bst DNA polymerase comprising the amino acid sequence of SEQ ID NO: 4. In other embodiments, the disclosure relates generally to an isolated variant of a protein comprising the amino acid sequence shown in SEQ ID NO: 3, wherein the variant comprises an amino acid sequence that is at least 95% identical to SEQ ID NO: 4.

In other embodiments of the method, the DNA polymerase is a Therminator™ DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In other embodiments of the method, the DNA polymerase is a KOD DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In other embodiments of the method, the DNA polymerase is a B103 DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

Candidate modified proteins may be synthesized in a variety of ways, including by way of molecular cloning and expression, or by chemical synthesis. Chemical synthesis of such proteins may be carried out by native chemical ligation, as described by Dawson et al (Science 266: 776-779 (1994)); Hakeng et al (Proc. Natl. Acad. Sci. USA 94: 7845-7850 (1997)); Hakeng et al (Proc. Natl. Acad. Sci. USA 96: 10068-10073 (1999)); and Kent et al., U.S. Pat. No. 6,184,344, which are incorporated herein by reference.

Modified proteins may also be produced by recombinant techniques. In some embodiments, the disclosure relates generally to recombinant DNA or RNA molecules encoding a modified protein, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., Molecular Cloning: A Laboratory Manual 3rd. edition (2001) Cold Spring Harbor Laboratory Press, Cold Spring Harbor, N.Y.).

In some embodiments, the disclosure relates generally to a host-vector system comprising a recombinant DNA molecule containing a sequence encoding a modified protein within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Polynucleotides comprising the coding sequence of a non buffering protein can be used to generate modified proteins using any number of host-vector systems routinely used and widely known in the art.

The disclosure relates generally to an isolated nucleic acid that is at least 70%, at least 75%, at least 80%, at least 81%, at least 82%, at least 83%, at least 84%, at least 85%, at least 86%, at least 87%, at least 89%, at least 90%, at least 91%, at least 92%, at least 93%, at least 94%, at least 95%, at least 96%, at least 97%, at least 98%, or at least 99% identical to a nucleic acid encoding any of the modified proteins disclosed herein.

Polynucleotide sequences encoding the modified proteins can be obtained using standard recombinant techniques. Alternatively, polynucleotides can be synthesized using nucleotide synthesizer or PCR techniques. Once obtained, sequences encoding the modified proteins are inserted into a recombinant vector capable of replicating and expressing heterologous polynucleotides in prokaryotic hosts. Many vectors that are available and known in the art can be used. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby allowing a skilled worker operably to ligate them to cistrons encoding the target light and heavy chains (Siebenlist et al. (1980) Cell 20: 269) using linkers or adaptors to supply any required restriction sites.

In some embodiments, each cistron within the recombinant vector comprises a secretion signal sequence component that directs translocation of the expressed polypeptides across a membrane. In general, the signal sequence may be a component of the vector, or it may be a native part of the target polypeptide DNA that is inserted into the vector. The signal sequence selected should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In some embodiments, the signal sequences used in both cistrons of the expression system are STII signal sequences or variants thereof.

In some embodiments, the production of the modified proteins can occur in the cytoplasm of the host cell, and therefore does not require the presence of secretion signal sequences within each cistron. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing modified proteins include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In some embodiments, gram-negative cells are used. In some embodiments, E. coli cells are used as hosts. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coliλ 1776 (ATCC 31,537) and E. coli RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce polypeptides according to the disclosure can be grown in any suitable media, including media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for E. coli growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for E. coli, the pH is from about 6.8 to about 7.4, or about 7.0.

If an inducible promoter is used in the expression vector, protein expression is induced under conditions suitable for the activation of the promoter. In some embodiments, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In some embodiments, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In some embodiments, production of modified proteins is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the proteins, various fermentation conditions can be suitably modified. For example, to improve the proper assembly and folding of the secreted modified proteins, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In some embodiments, the modified protein includes one or more chemical modifications that reduce the buffering capacity of the protein. In one example, the modified protein includes an N-terminal amino acid residue that is chemically modified, for example an N-terminal methionine residue, by the addition of a formyl group. Such formylation can be useful in reducing the buffering capacity of the N-terminal amino acid residue that includes a primary amino group. Formyl-modified proteins can be expressed and/or purified from host cells having a reduced activity of methionine aminopeptidase (MAP) relative to a corresponding wild-type host cell. The use of such MAP-deficient strains can improve expression of formyl-modified proteins. See, e.g., Sherman, F., J. W. Stewart, and S. Tsunasawa. 1985. Methionine or not methionine at the beginning of a protein. BioEssays 3:27-31.

In some embodiments, the modified protein produced herein is further purified to obtain preparations that are substantially homogeneous for further assays and uses. Standard protein purification methods known in the art can be employed. The following procedures are exemplary of suitable purification procedures: fractionation on immuno-affinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In some embodiments, the disclosure relates generally to polypeptides comprising a modified protein fused to another polypeptide to form a chimeric polypeptide. In some embodiments, the chimeric polypeptide comprises a tag polypeptide which provides an epitope which is selectively bound by an anti-tag antibody. The epitope tag allows the modified protein to be purified by affinity purification using the anti-tag antibody. Epitope tags and their respective antibodies are well known in the art. Examples include the flu HA tag polypeptide and its antibody 12CA5 (Field et al. Mol. Cell Biol. 8: 2159-2165 (1988)); the c-myc tag and the 8F9, 3C7, 6E10, G4, B7 and 9E10 antibodies thereto (Evan et al., Mol. Cell Biol. 5: 3610-3616 (1985); and the Herpes Simplex virus glycoprotein D (gD) tag and its antibody (Paborsky et al., Protein Engineering 3: 547-553 (1990)). Other examples of epitope tags include the Flag-peptide (Hopp et al., BioTechnology 6: 1204-1210 (1998); the KT3 epitope peptide (Martin et al., Science 255: 192-194 (1992)); an a-tubulin epitope peptide (Skinner et al, J. Biol. Chem. 266: 15163-15166 (1991)) and the T7 gp10 peptide tag (Lutz-Freyermuth et al., Proc. Natl. Acad. Sci. USA 87: 6393-6397 (1990)).

Epitope-tagged modified proteins can be conveniently purified by affinity chromatography using the anti-tag antibody. The matrix to which the anti-tag antibody is attached is most often agarose, but other matrices are available (e.g., controlled pore glass or poly(styrenedivinyl)benzene). The epitope-tagged modified proteins can be eluted from the affinity column by, for example, varying the buffer pH or ionic strength, or by addition of chaotropic agents.

In some embodiments, a modified protein is fused to a histidine tag (His-tag). The His-tagged modified protein can be purified by, for example, using a nickel column using standard techniques.

In some embodiments, the disclosure relates generally to methods, compositions, systems, apparatuses and kits that may be used for the detection and/or monitoring of biological and chemical reactions. These reactions may include enzymatic reactions in which substrates and/or reagents are consumed and/or reaction intermediates, byproducts and/or products are generated. In some embodiments, the disclosure relates generally to compositions and methods that may be used for the detection and/or monitoring of biological and chemical reactions wherein the concentration of at least one type of ion changes during the course of the reaction. An example of such a reaction is a nucleic acid synthesis method such as one that provides information regarding nucleic acid sequence.

In various embodiments, a biological or chemical reaction is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array is an array having one column (or row) of elements in the first dimension and a plurality of columns (or rows) in the second dimension. The number of columns (or rows) in the first and second dimensions may or may not be the same. The FET or array may comprise 102, 103, 104, 105, 106, 107 or more FETs.

In some embodiments, one or more microfluidic structures is/are fabricated above the FET sensor array to provide for containment and/or confinement of a biological or chemical reaction. For example, in one implementation, the microfluidic structure(s) may be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there is a 1:1 correspondence of FET sensors and reaction wells.

Microwells or reaction chambers are typically hollows or wells having well-defined shapes and volumes which are manufactured into a substrate and may be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Preferable configurations (e.g. spacing, shape and volumes) of microwells or reaction chambers are disclosed in Rothberg et al, U.S. patent publication 2009/0127589; Rothberg et al, U.K. patent application GB24611127, which are incorporated by reference.

In some embodiments, the biological or chemical reaction is performed in a solution or a reaction chamber that is in contact with or capacitively coupled to a FET such as a chemFET or an ISFET. The FET (or chemFET or ISFET) and/or reaction chamber may be an array of FETs or reaction chambers, respectively.

In some embodiments, a biological or chemical reaction is carried out in a two-dimensional array of reaction chambers, wherein each reaction chamber is coupled to a FET, and each reaction chamber is no greater than 10 µm$^3$ (i.e., 1 pL) in volume. In some embodiments each reaction chamber is no greater than 0.34 pL, 0.096 pL or even 0.012 pL in volume. A reaction chamber can optionally be 22, 32, 42, 52, 62, 72, 82, 92, or 102 square microns in cross-sectional area at the top. Preferably, the array has at least 102, 103, 104, 105, 106, 107, 108, 109, or more reaction chambers. In some embodiments, the reaction chambers are capacitively coupled to the FETs.

FET arrays as used in various embodiments according to the disclosure may be fabricated according to conventional CMOS fabrications techniques, as well as modified CMOS fabrication techniques and other semiconductor fabrication techniques beyond those conventionally employed in CMOS fabrication. Additionally, various lithography techniques may be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082.

In some embodiments, the disclosure relates generally to a method of detecting a change in ion concentration during a chemical reaction, comprising: performing a chemical reaction in the presence of a modified polypeptide having one or more amino acid substitutions, wherein the concentration of at least one type of ion changes during the course of the chemical reaction; and detecting a signal indicating the change in ion concentration, wherein the signal is increased relative to a signal that is detected from a chemical reaction performed in the presence of the unmodified polypeptide but under otherwise identical reaction conditions.

In some embodiments, the modified polypeptide includes one or more amino acid substitutions that reduce the buffering capacity of the modified polypeptide relative to the unmodified polypeptide.

In some embodiments, at least one of the one or more amino acid substitutions includes the substitution of an amino acid residue having a pKa of between about 4 and 10 with another amino acid residue having a pKa less than about 4 or greater than about 10.

In some embodiments, the modified polypeptide is a DNA or RNA binding protein. In various embodiments, the polypeptide is a DNA polymerase, a helicase, a ligase, a nuclease, a single stranded DNA binding protein or a polymerase accessory protein.

In some embodiments, the modified polypeptide is a modified polymerase, and the chemical reaction includes a nucleotide incorporation.

In some embodiments of the method, the modified polypeptide is a polymerase comprising one or more amino acid substitutions that reduce the buffering capacity of said protein relative to the corresponding wild-type protein within the range of about pH 4 to about pH 10. In some embodiments, the one or more amino acid substitutions reduce the buffering capacity of the polymerase relative to the corresponding wild-type polymerase within the range of about pH 7 to about pH 9.

In some embodiments, the one or more amino acid substitutions substantially reduce the buffering capacity of the polymerase within the range of about pH 7 to pH 9. In some embodiments, at least one of the one or more amino acid substitution is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In various embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Bst polymerase, Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator™ polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 which is incorporated by reference herein.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments of the method, the DNA polymerase is a Bst DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 2 or Table 3. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the Bst DNA polymerase comprises one or more conservative amino acid substitutions, wherein the one or more amino acid substitutions includes a substitution of alanine at position 2 with Met, Asn, Gln, Leu, Ile, Phe, or Trp, the numbering of amino acid residues being in accordance with that of SEQ ID NO: 1.

In some embodiments of the method, the polymerase is a Bst DNA polymerase comprising an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the disclosure relates generally to an isolated variant of a protein comprising the amino acid sequence shown in SEQ ID NO: 2, wherein the variant comprises an amino acid sequence that is at least 95% identical to SEQ ID NO: 2.

In some embodiments, the polymerase is a Bst DNA polymerase comprising the amino acid sequence of SEQ ID NO: 3. In some embodiments, the disclosure relates generally to an isolated variant of a protein comprising the amino acid sequence shown in SEQ ID NO: 3, wherein the variant comprises an amino acid sequence that is at least 95% identical to SEQ ID NO: 3.

In some embodiments, the polymerase is a Bst DNA polymerase comprising the amino acid sequence of SEQ ID NO: 4. In other embodiments, the disclosure relates generally to an isolated variant of a protein comprising the amino acid sequence shown in SEQ ID NO: 3, wherein the variant comprises an amino acid sequence that is at least 95% identical to SEQ ID NO: 4.

In other embodiments of the method, the DNA polymerase is a Therminator™ DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In other embodiments of the method, the DNA polymerase is a KOD DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In other embodiments of the method, the DNA polymerase is a B103 DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments of the method, the polymerase comprises one or more amino acid substitutions that reduce the buffering capacity of said protein relative to the corresponding wild-type protein within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid modifications includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid modifications includes a substitution of an amino acid residue with an alanine residue.

In some embodiments, at least one of the one or more amino acid substitutions includes a substitution of an amino acid residue that is at least 30% solvent exposed in the corresponding wild-type protein with another amino acid residue.

In some embodiments of the method, the polymerase comprises one or more chemical amino acid modifications that reduce the buffering capacity of said protein relative to the corresponding wild-type protein within the range of about pH 4 to about pH 10. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In some embodiments, the amine-reactive reagent includes an acylating agent or an activated ester.

In some embodiments of the method of detecting a change in ion concentration during a chemical reaction, the detecting step comprises using a chemFET. In some embodiments, the chemFET is an ISFET. In some embodiments, the ISFET is in an ISFET array.

In some embodiments, the chemical reaction is performed in a reaction chamber comprising or capacitively coupled to a chemFET.

In some embodiments, the chemical reaction is in the presence of an agent that alters the value of a pKa of at least an amino acid in the modified polypeptide from within the range of about 6 to about 8 to less than about 6 or greater than about 8. In some embodiments, the agent is a phospholipid, a sulfonic acid surfactant, a polyanionic electrolyte or a salt thereof, a polycationic electrolyte or a salt thereof, tetramethyl ammonium or a salt thereof, or a combination thereof.

In some embodiments, at least one type of ion is hydrogen ion.

In some embodiments, the reaction is an enzymatic reaction or a binding reaction.

In some embodiments, the chemical reaction is an enzymatic reaction. In some embodiments, the enzymatic reaction is a nucleotide incorporation reaction.

In some embodiments, the disclosed methods further include repeating steps a)-b).

In some embodiments, the disclosure relates generally to methods for using the modified proteins of the disclosure to obtain sequence information regarding a nucleic acid of interest. Such methods involve the synthesis of a new nucleic acid (e.g., using a primer that is hybridized to a template nucleic acid or a self-priming template, as will be appreciated by those of ordinary skill), based on the sequence of a template nucleic acid. That is, the sequence of the newly synthesized nucleic acid is complementary to the sequence of the template nucleic acid and therefore knowledge of sequence of the newly synthesized nucleic acid yields information about the sequence of the template nucleic acid.

In one aspect, the disclosed methods, compositions, systems, apparatuses and kits may be used for carrying out label-free nucleic acid sequencing, and in particular, ion-based nucleic acid sequencing. The concept of label-free nucleic acid sequencing, including ion-based nucleic acid sequencing, has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase).

In a typical embodiment of ion-based nucleic acid sequencing, nucleotide incorporations are detected by detecting the presence and/or concentration of hydrogen ions generated by polymerase-catalyzed extension reactions. In one embodiment, templates each having a primer and polymerase operably bound are loaded into reaction chambers (such as the microwells disclosed in Rothberg et al, cited above), after which repeated cycles of nucleotide addition and washing are carried out. In some embodiments, such templates may be attached as clonal populations to a solid support, such as a microparticle, bead, or the like, and said clonal populations are loaded into reaction chambers. For example, templates may be prepared as disclosed in U.S. Pat. No. 7,323,305, which is incorporated by reference. As used herein, "operably bound" means that a primer is annealed to a template so that the primer's 3' end may be extended by a polymerase and that a polymerase is bound to such primer-template duplex, or in close proximity thereof so that binding and/or extension takes place whenever nucleotides are added.

In each addition step of the cycle, the polymerase extends the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released. In some embodiments, after each step of adding a nucleotide, an additional step may be performed, in which an unbuffered wash solution at a predetermined pH is used to remove the nucleotide of the previous step in order to prevent misincorporations in later cycles. In some embodiments, the after each step of adding a nucleotide, an additional step may be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction is exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, the polymerase can include without limitation any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example E. coli DNA polymerase, Bst DNA polymerase, Taq polymerase, T7 polymerase, Phi-29 DNA polymerase, B103 polymerase and reverse transcriptases) and RNA polymerases. The term "polymerase" and its variants may also refer to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. One exemplary embodiment of such a polymerase is Phusion® DNA polymerase (New England Biolabs), which comprises a *Pyrococcus*-like polymerase fused to a processivity-enhancing domain as described, for example, in U.S. Pat. No. 6,627,424.

In some embodiments, the modified polymerase comprises one or more modifications resulting in altered exonuclease activity (for example 3' to 5' exonuclease activity) as compared to a reference polymerase (for example, an unmodified counterpart). In some embodiments, the modification comprises an amino acid substitution. In some embodiments, the modified polymerase lacks 3' to 5' exonuclease activity, or lacks 5' to 3' exonuclease activity, or both. Mutations at conversed amino acid residues that reduce or eliminate 3' to 5' exonuclease activity have been described for various polymerases. For example, amino acid mutations reducing exonuclease activity in Phi-29-type polymerases at various residues have been described, for example, in de Vega et al., "Primer-terminus stabilization at the 3'-5' exonuclease active site of Φ29 DNA polymerase. Involvement of two amino acid residues highly conserved in proofreading DNA polymerases" EMBO J., 15(5):1182-1192 (1996); Soengas et al., "Site-directed mutagenesis at the Exo III motif of D29 DNA polymerase; overlapping structural domains for the 3'-5' exonuclease and strand-displacement activities" EMBO J., 11(11):4227-4237 (1992); Blanco et al., U.S. Pat. Nos. 5,001,050, 5,198,543 and 5,576,204.

One exemplary polymerase suitable for use in some but not all embodiments is the exo-minus (exo-) version of the Klenow fragment of E. coli DNA polymerase I which lacks 3' to 5' exonuclease activity. Other polymerases include T4 exo-, Therminator™, and Bst polymerases, as well as variants of the B106 DNA polymerase containing modifications that reduce its 3' to 5' exonuclease activity as disclosed in U.S. Patent Publication No. 20110014612, which is incorporated by reference herein. In still other embodiments that require excision of nucleotides (e.g., in the process of a nick translation reaction), polymerases with exonuclease activity are preferred. Since DNA synthesis fidelity depends mainly on the presence or absence of 3'-5' exonuclease activity, enzymes with 3'-5' exonuclease activity can be used in some embodiments. A combination of enzymes can also be used. The polymerase may be one that is modified to comprise accessory factors including without limitation single or double stranded DNA binding proteins.

Some embodiments may require that the polymerase have sufficient processivity. As used herein, processivity is the ability of a polymerase to remain bound to a single primer/template hybrid. It may be measured by the number of nucleotides that a polymerase incorporates into a nucleic acid (such as a sequencing primer) prior to dissociation of the polymerase from the primer/template hybrid. In some embodiments, the polymerase has a processivity of at least 100 nucleotides, although in other embodiments it has a processivity of at least 200 nucleotides, at least 300 nucleotides, at least 400 nucleotides, or at least 500 nucleotides. It will be understood by those of ordinary skill in the art that the higher the processivity of the polymerase, the more nucleotides that can be incorporated prior to dissociation, and therefore the longer the sequence that can be obtained. In other words, polymerases having low processivity will provide shorter read-lengths than will polymerases having higher processivity. As an example, a polymerase that dissociates from the hybrid after five incorporations will only provide a sequence of 5 nucleotides in length, while a polymerase that dissociates on average from the hybrid after 500 incorporations will provide sequence of about 500 nucleotides.

The rate at which a polymerase incorporates nucleotides will vary depending on the particular application, although generally faster rates of incorporation are desirable. The rate of "sequencing" will depend on the number of arrays on chip, the size of the wells, the temperature and conditions at which the reactions are run, etc.

In some embodiments, the nucleotides are delivered at substantially the same time to each template. In some embodiments, polymerase(s) are already present, although in some embodiments they may be introduced along with the nucleotides. The polymerases may be immobilized or may be free flowing. In embodiments where the polymerases are immobilized, the polymerases may be attached to a solid support such as a bead surface, a bead interior or some combination of bead surface and interior. Typically, the bead is present in a reaction chamber, although the methods may also be carried out in the absence of reaction chambers. The solid support may also be the sensor surface or a wall of a reaction chamber that is capacitively coupled to the sensor.

The reaction may occur in a reaction chamber in some embodiments, while in others it may occur in the absence of reaction chambers. In these latter embodiments, the sensor surface may be continuous without any physical divider between sensors.

In some embodiments, the nucleotide can include any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. The nucleotide can include not only any naturally occurring nucleotide but also any analog, regardless of its structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, CNH2, C(O), C(CH2), CH2CH2, or C(OH)CH2R (where R can be a 4-pyridine or 1-imidazole). In one embodiment, the phosphorus atoms in the chain can have side groups having O, BH3, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

Some embodiments of the disclosure relate generally to detecting hydrogen ions released as a function of nucleotide incorporation; some embodiments relate generally to detecting hydrogen ions released as a function of nucleotide excision. It is important in these and various other aspects to detect as many released hydrogen ions as possible in order to achieve as high a signal (and/or a signal to noise ratio) as possible. Strategies for increasing the number of released protons that are ultimately detected by the FET surface include without limitation limiting interaction of released protons with reactive groups in the well, choosing a material from which to manufacture the well in the first instance that is relatively inert to protons, preventing released protons from exiting the well prior to detection at the chemFET, and increasing the copy number of templates per well (in order to amplify the signal from each nucleotide incorporation), among others.

Some embodiments of the disclosed methods employ an environment, for example a reaction solution, which is minimally buffered, if at all. Buffering can be contributed by the components of the solution or by the solid supports in contact with such solution. A solution having no or low buffering capacity (or activity) is one in which changes in hydrogen ion concentration on the order of at least about +/−0.005 pH units, at least about +/−0.01, at least about +/−0.015, at least about +/−0.02, at least about +/−0.03, at least about +/−0.04, at least about +/−0.05, at least about +/−0.10, at least about +/−0.15, at least about +/−0.20, at least about +/−0.25, at least about +/−0.30, at least about +/−0.35, at least about +/−0.45, at least about +/−0.50, or more are detectable (e.g., using the chemFET sensors described herein). In some embodiments, the pH change per nucleotide incorporation is on the order of about 0.005. In some embodiments, the pH change per nucleotide incorporation is a decrease in pH. Reaction solutions that have no or low buffering capacity may contain no or very low concentrations of buffer, or may use weak buffers.

The reaction solution may have a buffer concentration equal to or less than 1 mM, equal to or less than 0.9 mM, equal to or less than 0.8 mM, equal to or less than 0.7 mM, equal to or less than 0.6 mM, equal to or less than 0.5 mM, equal to or less than 0.4 mM, equal to or less than 0.3 mM, equal to or less than 0.2 mM, equal to or less than 0.1 mM, or less including zero. The buffer concentration may be 50-100 µM. A non-limiting example of a weak buffer suitable for the sequencing reactions described herein wherein pH change is the readout is 0.1 mM Tris or Tricine.

In some aspects, in addition to or instead of using reduced buffering solutions, nucleotide incorporation (and optionally excision) is carried out in the presence of additional agents that serve to shield potential buffering events that may occur in solution. These agents are referred to herein as buffering inhibitors since they inhibit the ability of components within a solution or a solid support in contact with the solution to sequester and/or otherwise interfere with released hydrogen ions prior to their detection by the FET surface. In the absence of such inhibitors, released hydrogen ions may interact with or be sequestered by reactive groups in the solution or on solid supports in contact with the solution. These hydrogen ions are less likely to reach and be detected by the FET surface, leading to a weaker signal than is otherwise possible. In the presence of such inhibitors however there will be fewer reactive groups available for interaction with or sequestration of hydrogen ions. As a result, a greater proportion of released hydrogen ions will reach and be detected by the FET surface, leading to stronger signals. Some suitable buffering inhibitors demonstrate little or no buffering capacity in the pH range of 5-9, meaning that pH changes on the order of 0.005, 0.01, 0.02, 0.03, 0.04, 0.05, 0.1, 0.2, 0.3, 0.4, 0.5 or more pH units are detectable (e.g., by using an ISFET) in the presence of such inhibitors.

There are various types of buffering inhibitors. One example of a class of buffering inhibitors is phospholipids. The phospholipids may be naturally occurring or non-naturally occurring phospholipids. Examples of phospholipids that may be used as buffering inhibitors include but are not limited to phosphatidylcholine, phosphatidylethanolamine, phosphatidylglycerol, and phosphatidylserine.

Another example of a class of buffering inhibitors is sulfonic acid based surfactants such as poly(ethylene glycol) 4-nonylphenyl 3-sulfopropyl ether (PNSE). In addition to shielding reactive groups that would otherwise interfere with released protons, PNSE has also been reported to enhance polymerase activity.

Another example of a class of buffering inhibitors is polyanionic electrolytes such as poly(styrenesulfonic acid or its sodium salt.

Another example of a class of buffering inhibitors is polycationic electrolytes such as poly(diallydimethylammonium) or its chloride salt. These compounds are known to bind to DNA.

Another example of a buffering inhibitor is tetramethyl ammonium or its chloride salt.

These various inhibitors may be present throughout a reaction by being included in nucleotide solutions, wash solutions, and the like. Alternatively, they may be flowed through the reaction chamber at set times relative to the flow through of nucleotides and/or other reaction reagents. In still other embodiments, they may be coated on the FET surface (or reaction chamber surface). Such coating may be covalent or non-covalent.

In one embodiment, the disclosure relates generally to a method for obtaining sequence information from a nucleic acid template, comprising: (a) providing a template nucleic acid hybridized to a sequencing primer and bound to a polymerase, wherein the polymerase comprises one or more amino acid substitutions that substantially reduce its buffering capacity within the range of about pH 4 to about pH 10; (b) synthesizing a new nucleic acid strand by sequentially incorporating one or more nucleotides at the 3' end of the sequencing primer, wherein a hydrogen ion byproduct is generated when the nucleotide is complementary to corresponding nucleotides in the template nucleic acid; and (c) detecting the incorporation of the one or more nucleotides into the sequencing primer by detecting the release of hydrogen ions.

In some embodiments, the one or more amino acid substitutions in the polymerase reduce the buffering capacity of the polymerase relative to the corresponding wild-type (unsubstituted) polymerase within the range of about pH 7 to about pH 9.

In some embodiments, at least one of the one or more amino acid substitutions in the polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the polymerase comprises one or more amino acid substitutions that reduce the buffering capacity of said polymerase relative to the corresponding wild-type polymerase within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, the polymerase comprises one or more amino acid substitutions that reduce the buffering capacity of said polymerase relative to the corresponding wild-type polymerase within the range of about pH 7 to about pH 9. In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 7 and about 9 with an amino acid residue having a pKa that is less than about 7 or greater than about 9. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid modifications includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions are selected from the group consisting of: substitution of a surface histidine with an arginine, substitution of a surface glutamic acid with a glutamine, and substitution of a surface lysine with an arginine.

In some embodiments, at least one of the one or more amino acid modifications is a substitution of an amino acid residue with an alanine residue.

In some embodiments of the method, at least one of the one or more amino acid modifications in the polymerase is a deletion of an amino acid. In some embodiments, at least one of the one or more deleted amino acids is an amino acid residue having a pKa of between about 4.0 and about 10.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more deleted amino acids is an amino acid residue having a pKa within the range of about 6.0 to about 8.0 with another amino acid residue. In some embodiments, the deleted amino acid is His, Glu, Asp, Tyr or Lys.

In some embodiments of the method, the polymerase comprises one or more chemical amino acid modifications that reduce the buffering capacity of the protein relative to the corresponding wild-type protein within the range of about pH 4 to about pH 10, about pH 5.5 to about pH 9.5, or about pH 7 to about pH 9. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In further embodiments, the amine-reactive reagent includes an acylating agent or an activated ester.

In some embodiments, at least one of the one or more amino acid substitutions, deletions or chemical modifications includes a substitution of an amino acid residue that is at least 20%, at least 25%, at least 30%, at least 35% or at least 40% solvent exposed in the corresponding wild-type protein with another amino acid residue.

It will be understood that the polymerase may comprise any combination of amino acid substitutions, deletions or chemical modifications. A polymerase comprising any one or more of such additions, substitutions, deletions and chemical modifications may be referred to a "modified" polymerase.

In some embodiments, the modified polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10.

In some embodiments, the one or more amino acid substitutions in the Bst DNA polymerase reduce the buffering capacity of the polymerase relative to the corresponding wild-type (unsubstituted) polymerase within the range of about pH 7 to about pH 9.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In other embodiments of the method, the DNA polymerase is a Therminator™ DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In other embodiments of the method, the DNA polymerase is a KOD DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In other embodiments of the method, the DNA polymerase is a B103 DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the method for obtaining sequence information from a nucleic acid template further comprises providing an SSB, wherein the SSB comprises one or more amino acid substitutions that substantially reduce its buffering capacity within the range of about pH 4 to about pH 10.

In some embodiments, the one or more amino acid substitutions in the SSB reduce the buffering capacity of the SSB relative to the corresponding wild-type SSB within the range of about pH 7 to about pH 9.

In some embodiments, at least one of the one or more amino acid substitutions in the SSB is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the SSB is E. coli SSB. In further embodiments, the one or more conservative amino acid substitutions are of one or more amino acid residues shown in Table 2. In some embodiments, the SSB comprises the amino acid substitution K7R.

In some embodiments, the disclosure relates generally to a method for sequencing a nucleic acid, comprising: disposing a plurality of template nucleic acids into a plurality of reaction chambers, wherein one or more of the reaction chambers are in contact with a field effect transistor (FET) array, and contacting at least one of the template nucleic acids with a polymerase including one or more conservative amino acid substitutions that substantially reduce its buffering capacity within the range of pH 7 to pH 9; synthesizing a new nucleic acid strand by sequentially incorporating one or more nucleotides into a nucleic acid molecule and generating one or more hydrogen ions as a byproduct of such nucleotide incorporation; and detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET is selected from the group consisting of: ion-sensitive FET (isFET) and chemically-sensitive FET (chemFET).

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is E. coli SSB. In further embodiments, the one or more conservative amino acid substitutions in the SSB are of one or more amino acid residues shown in Table 4.

In another embodiment, the disclosure relates generally to a method for obtaining sequence information from a nucleic acid comprising:

(a) disposing a plurality of solid or semi-solid supports into a plurality of reaction chambers on a sensor array formed in a semiconductor substrate, at least one reaction chamber including a polymerase, a sequencing primer and a single solid or semi-solid support attached to a plurality of template nucleic acids having at least 80% sequence identity to each other, wherein the polymerase comprises one or more amino acid substitutions that substantially remove its buffering capacity within the range of pH 7 to pH 9, and each reaction chamber is in contact with or capacitively coupled to a sensor including a FET configured to provide at least one output representing the presence of one or more hydrogen ions in the reaction chamber;

(b) introducing at least one nucleotide into the at least one reaction chamber and incorporating the at least one nucleotide into the primer using the polymerase, thereby generating one or more hydrogen ion byproducts;

(c) detecting the incorporation of the at least one nucleotides by detecting the presence of the hydrogen ion byproducts.

In some embodiments, the method further includes repeating steps (a) through (c) until the nucleic acid is sequenced.

In some embodiments, the method further includes a step of washing unincorporated nucleotides from the at least one reaction chambers.

In some embodiments, the method further includes repeating steps (a) through (c) as well as the washing step until the nucleic acid is sequenced.

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is E. coli SSB. In further embodiments, the one or more conservative amino acid substitutions in the SSB are of one or more amino acid residues shown in Table 4.

In a further embodiment, the disclosure relates generally to a method for reducing the buffering capacity of a protein used in a DNA sequencing or amplification reaction, comprising making one or more amino acid substitutions in the protein sequence that substantially reduce the protein's buffering capacity within the range of about pH 4 to about pH 10.

In some embodiments, the amino acid substitutions substantially reduce the protein's buffering capacity within the range of about pH 7 to about pH 9.

In some embodiments, at least one of the one or more amino acid substitutions includes a substitution of an amino acid residue having a pKa in the range of about 4 to about 10 with an amino acid residue having a pKa less than about 4 or greater than about 10.

In some embodiments, the protein is a DNA- or RNA-binding protein.

In various embodiments, the protein is a DNA polymerase selected from the group consisting of an A family DNA polymerase; a B family polymerase; a mixed-type polymerase; an unclassified DNA polymerase; an RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase; a B family DNA polymerase selected from the group consisting of, Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase; a mixed-type polymerase selected from the group consisting of EX-Taq polymerase, LA-Taq polymerase, Expand polymerase series, and Hi-Fi polymerase; an unclassified DNA polymerase selected from the group consisting of Tbr polymerase, Tfl polymerase, Tru polymerase, Tac polymerase, Tne polymerase, Tma polymerase, Tih polymerase, and Tfi polymerase; and an RT polymerase selected from the group consisting of HIV reverse transcriptase, M-MLV reverse transcriptase and AMV reverse transcriptase.

In some embodiments, the polymerase is Bst DNA polymerase. In further embodiments, the one or more conservative amino acid substitutions within the polymerase are of one or more amino acid residues shown in Table 2 or Table 3. In further embodiments, the one or more conservative amino acid substitutions are selected from the group consisting of H341R, H568R, H576R, E741Q, H768R, H823R, H867R and Y772F. In some embodiments, the polymerase is selected from the group consisting of SEQ ID NO: 2, SEQ ID NO: 3 and SEQ ID NO: 4, or a variant thereof having one or more conservative amino acid substitutions.

In some embodiments, the method further comprises providing an SSB, wherein the SSB comprises one or more conservative amino acid substitutions that substantially remove its buffering capacity within the range of pH 7 to pH 9. In further embodiments, the SSB is E. coli SSB. In further embodiments, the one or more conservative amino acid substitutions in the SSB are of one or more amino acid residues shown in Table 2.

In a further embodiment, the disclosure relates generally to a method of detecting a nucleotide incorporation, comprising:

(a) performing a nucleotide incorporation using a modified polymerase and generating one or more hydrogen ions as a by-product of the nucleotide incorporation, where the modified polymerase includes one or more amino acid substitutions that reduce the buffering capacity of the modified polymerase relative to the unmodified polymerase; and (b) detecting the presence of the one or more hydrogen ions generated as a by-product of the nucleotide incorporation, thereby detecting the nucleotide incorporation.

In various embodiments, the polymerase may be any of the modified polymerases containing any one or more of the substitutions, deletions or chemical modifications described herein.

In some embodiments, the modified polymerase includes one or more amino acid substitutions that reduce the buffering capacity of the modified polymerase within the pH range of about 4 to about 10 relative to the unmodified polymerase.

In some embodiments, the one or more amino acid substitutions in the polymerase reduce the buffering capacity of the polymerase relative to the corresponding wild-type (unsubstituted) polymerase within the range of about pH 7 to about pH 9.

In some embodiments, at least one of the one or more amino acid substitutions in the polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the polymerase comprises one or more amino acid substitutions that reduce the buffering capacity of said polymerase relative to the corresponding wild-type polymerase within the range of about pH 4 to about pH 10, wherein at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid modifications includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid modifications is a substitution of an amino acid residue with an alanine residue.

In some embodiments of the method, at least one of the one or more amino acid modifications in the polymerase is a deletion of an amino acid. In some embodiments, at least one of the one or more deleted amino acids is an amino acid residue having a pKa of between about 4.0 and about 10.0. In some embodiments, the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more deleted amino acids is an amino acid residue having a pKa within the range of about 6.0 to about 8.0 with another amino acid residue. In some embodiments, the deleted amino acid is His, Glu, Asp, Tyr or Lys.

In some embodiments of the method, the polymerase comprises one or more chemical amino acid modifications that reduce the buffering capacity of the protein relative to the corresponding wild-type protein within the range of about pH 4 to about pH 10, about pH 5.5 to about pH 9.5, or about pH 7 to about pH 9. In some embodiments, the one or more chemical amino acid modifications includes a chemical modification of the N-terminal amino acid. In some embodiments, the one or more chemical amino acid modifications includes a chemical modification of an amino acid residue including a primary amine group with an amine-reactive agent. In further embodiments, the amine-reactive reagent includes an acylating agent or an activated ester.

In some embodiments, at least one of the one or more amino acid substitutions, deletions or chemical modifications includes a substitution of an amino acid residue that is at least 20%, at least 25%, at least 30%, at least 35% or at least 40% solvent exposed in the corresponding wild-type protein with another amino acid residue.

In some embodiments, the modified polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10.

In some embodiments, the one or more amino acid substitutions in the Bst DNA polymerase reduce the buffering capacity of the polymerase relative to the corresponding wild-type (unsubstituted) polymerase within the range of about pH 7 to about pH 9.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In other embodiments of the method, the DNA polymerase is a Therminator™ DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In other embodiments of the method, the DNA polymerase is a KOD DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In other embodiments of the method, the DNA polymerase is a B103 DNA polymerase comprising one or more conservative amino acid substitutions that substantially reduce its buffering capacity relative to the corresponding wild-type protein within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the method further comprises providing an SSB, wherein the SSB comprises one or more amino acid substitutions that substantially reduce its buffering capacity within the range of about pH 4 to about pH 10.

In some embodiments, the one or more amino acid substitutions in the SSB reduce the buffering capacity of the SSB relative to the corresponding wild-type SSB within the range of about pH 7 to about pH 9.

In some embodiments, at least one of the one or more amino acid substitutions in the SSB is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the SSB is *E. coli* SSB. In further embodiments, the one or more conservative amino acid substitutions are of one or more amino acid residues shown in Table 2. In some embodiments, the SSB comprises the amino acid substitution K7R.

In some embodiments of the method of detecting a nucleotide incorporation, the detecting comprises using an ion-sensitive field effect transistor (ISFET). In some embodiments the ISFET is in an ISFET array.

In some embodiments the reaction is performed in a reaction chamber comprising or capacitively coupled to a chemFET.

In some embodiments, the reaction is in the presence of an agent that alters the value of a pKa of at least an amino acid in the modified polypeptide from within the range of about 6 to about 8 to less than about 6 or greater than about 8. In some embodiments, the agent is a phospholipid, a sulfonic acid surfactant, a polyanionic electrolyte or a salt thereof, a polycationic electrolyte or a salt thereof, tetramethyl ammonium or a salt thereof, or a combination thereof.

In some embodiments, the method further comprises repeating steps a)-b).

In some embodiments, the disclosure relates generally to methods for sequencing a nucleic acid, comprising: providing a template nucleic acid hybridized to a sequencing primer and bound to a polymerase; synthesizing a new nucleic acid strand by incorporating one or more known nucleoside triphosphates sequentially at the 3' end of the sequencing primer; and detecting such incorporation at the 3' end of the primer by measuring a concentration of a hydrogen ion byproduct generated if the known nucleoside triphosphate is complementary to corresponding nucleotides in the template nucleic acid.

In some embodiments, the one or more amino acid substitutions in the polymerase may include any one or more of the amino acid substitutions described herein.

In some embodiments, at least one of the one or more amino acid substitutions can be a conservative amino acid substitution.

In some embodiments, each of the one or more amino acid substitutions is a conservative amino acid substitution.

In some embodiments, the polymerase includes any one of the modified polymerases described herein. In some embodiments, the polymerase is a bufferless polymerase. For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, the polymerase includes one or more amino acid substitutions that substantially reduce the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially reduce the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the disclosure relates generally to methods for sequencing a nucleic acid, comprising: (a) disposing a plurality of template nucleic acids into a plurality of reaction chambers, wherein the plurality of reaction chambers is in contact with a chemical-sensitive field effect transistor (chemFET) array, the chemFET array comprising at least one chemFET for each reaction chamber, and wherein each of the template nucleic acids is bound to a polymerase, wherein the polymerase comprises one or more amino acid modifications that substantially reduce its buffering capacity relative to the corresponding unmodified polymerase; (b) synthesizing a new nucleic acid strand by sequentially incorporating one or more known nucleoside triphosphates at the 3' end of the sequencing primer, wherein a hydrogen ion byproduct is generated when the known nucleoside triphosphate is complementary to corresponding nucleotides in the template nucleic acid; and (c) detecting the incorporation of the one or more known nucleoside triphosphates by a change in voltage and/or current at the at least one chemFET within the array in response to a change in hydrogen ion concentration proximate thereto.

In some embodiments, the one or more amino acid substitutions in the polymerase may include any one or more of the amino acid substitutions described herein.

In some embodiments, at least one of the one or more amino acid substitutions can be a conservative amino acid substitution.

In some embodiments, each of the one or more amino acid substitutions is a conservative amino acid substitution.

In some embodiments, the polymerase includes any one of the modified polymerases described herein. In some embodiments, the polymerase is a bufferless polymerase. For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, the polymerase includes one or more amino acid substitutions that substantially reduce the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially reduce the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the disclosure relates generally to methods for sequencing a nucleic acid, comprising: (a) disposing a plurality of template nucleic acids into a plurality of reaction chambers, wherein the plurality of reaction chambers is in contact with a chemical-sensitive field effect transistor (chemFET) array, the chemFET array comprising at least one chemFET for each reaction chamber, and wherein each of the template nucleic acids is bound to a polymerase, wherein the polymerase comprises one or more amino acid substitutions that substantially reduce its buffering capacity; (b) synthesizing a new nucleic acid strand by sequentially incorporating one or more known nucleoside triphosphates at the 3' end of the sequencing primer, wherein a hydrogen ion byproduct is generated when the known nucleoside triphosphate is complementary to corresponding nucleotides in the template nucleic acid; and (c) detecting the incorporation of the one or more known nucleoside triphosphates by a change in voltage and/or current at the at least one chemFET within the array in response to a change in hydrogen ion concentration proximate thereto.

In some embodiments, the one or more amino acid substitutions in the polymerase may include any one or more of the amino acid substitutions described herein.

In some embodiments, at least one of the one or more amino acid substitutions can be a conservative amino acid substitution.

In some embodiments, each of the one or more amino acid substitutions is a conservative amino acid substitution.

In some embodiments, the polymerase includes any one of the modified polymerases described herein. In some embodiments, the polymerase is a bufferless polymerase. For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, the polymerase includes one or more amino acid substitutions that substantially reduce the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially reduce the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the disclosure relates generally to methods for sequencing a nucleic acid, comprising: (a) disposing a plurality of solid supports into a plurality of reaction chambers on a sensor array formed in a semiconductor substrate, each reaction chamber comprising a single solid support, each solid support attached to a plurality of identical template nucleic acids, each of the template nucleic acids hybridized to a sequencing primer and bound to a polymerase, wherein the polymerase comprises one or more amino acid substitutions that substantially reduce its buffering capacity, and each reaction chamber in contact with or capacitavely coupled to at least one chemFET of a sensor, and each such chemFET being configured to provide at least one output representing the presence and/or concentration of hydrogen ion proximate thereto; (b) introducing a known nucleoside triphosphate into each reaction chamber; (c) detecting sequential incorporation at the 3' end of the sequencing primer of one or more nucleoside triphosphates by the generation of a change in hydrogen ion concentration when the known nucleoside triphosphate is complementary to corresponding nucleotides in the template nucleic acid; and (d) washing unincorporated nucleoside triphosphates from the reaction chambers.

In some embodiments, the method further includes (e) repeating steps (b) through (d) until the nucleic acid is sequenced.

In some embodiments, the one or more amino acid substitutions in the polymerase may include any one or more of the amino acid substitutions described herein.

In some embodiments, at least one of the one or more amino acid substitutions can be a conservative amino acid substitution.

In some embodiments, each of the one or more amino acid substitutions is a conservative amino acid substitution.

In some embodiments, the polymerase includes any one of the modified polymerases described herein. In some embodiments, the polymerase is a bufferless polymerase.

For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, the polymerase includes one or more amino acid substitutions that substantially reduce the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially reduce the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the disclosure relates generally to methods for sequencing a nucleic acid, comprising: (a) disposing a solid support into a reaction chamber on a sensor array formed in a semiconductor substrate, where the solid support is attached to a plurality of substantially identical template nucleic acids, at least one of the template nucleic acids being hybridized to a sequencing primer and bound to a polymerase, wherein the polymerase comprises one or more amino acid substitutions that substantially reduce its buffering capacity, and the reaction chamber is in contact with or capacitavely coupled to at least one chemFET of a sensor, the chemFET being configured to provide at least one output representing the presence and/or concentration of hydrogen ion proximate thereto; (b) introducing nucleoside triphosphates of a known type into the reaction chamber; (c) detecting incorporation at the 3'end of the sequencing primer of one or more nucleoside triphosphates of the known type by detecting the generation of a change in hydrogen ion concentration resulting from the incorporation of the one or more nucleoside triphosphates by the polymerase; and (d) washing unincorporated nucleoside triphosphates from the reaction chamber.

In some embodiments, the method further includes (e) repeating steps (b) through (d) until the nucleic acid is sequenced.

In some embodiments, the one or more amino acid substitutions in the polymerase may include any one or more of the amino acid substitutions described herein.

In some embodiments, at least one of the one or more amino acid substitutions can be a conservative amino acid substitution.

In some embodiments, each of the one or more amino acid substitutions is a conservative amino acid substitution.

In some embodiments, the polymerase includes any one of the modified polymerases described herein. In some embodiments, the polymerase is a bufferless polymerase. For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, the polymerase includes one or more amino acid substitutions that substantially reduce the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially reduce the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is E. coli DNA polymerase. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 20110014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

Any suitable method of performing nucleic acid synthesis involving nucleotide incorporation and/or primer extension using a polymerase may be used to practice, use or perform any of the disclosed methods, compositions, systems, apparatuses and kits. Typically, polymerases are capable of catalyzing nucleotide incorporation onto the terminal 3'OH end of an extending nucleic acid molecule. When the extending nucleic acid molecule comprises a primer, the process is typically referred to as "primer extension." Typically but not necessarily such nucleotide incorporation occurs in a template-dependent fashion. Primer extension and other nucleotide incorporation assays are typically performed by contacting the template nucleic acid with a polymerase in the presence of nucleotides in an aqueous solution under nucleotide incorporation conditions. In some embodiments, the nucleotide incorporation reaction can include a primer, which can optionally be hybridized to the template to form a primer-template duplex. Typical nucleotide incorporation conditions are achieved once the template, polymerase, nucleotides and optionally primer are mixed with each other in a suitable aqueous formulation, thereby forming a nucleotide incorporation reaction mixture (or primer extension mixture). The aqueous formation can optionally include divalent cations and/or salts, particularly $Mg^{++}$ and/or $Ca^{++}$ ions. Typical nucleotide incorporation conditions have included well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. Most polymerases exhibit some levels of nucleotide incorporation activity over pH range of about 5.0 to about 9.5, more typically between about pH 7 and about pH 9, and sometimes between about pH 6 to about pH 8. The buffer can include chelating agents such as EDTA and EGTA, and the like. Although in some embodiments, nucleotide incorporation reactions may include buffering agents, such as Tris, Tricine, HEPES, MOPS, ACES, or MES, which can provide a pH range of about 5.0 to about 9.5, such buffering agents can optionally be reduced or eliminated when performing ion-based reactions requiring detection of ion byproducts. Methods of performing nucleic acid synthesis are well known and extensively practiced in the art and references teaching a wide range of nucleic acid synthesis techniques are readily available. Some exemplary teachings regarding the performance of nucleic acid synthesis (including, for example, template-dependent nucleotide incorporation, as well as primer extension methods) can be found, for example, in Kim et al., Nature 376: 612-616 (2002); Ichida et al., Nucleic Acids Res. 33: 5214-5222 (2005); Pandey et al., European Journal of Biochemistry, 214:59-65 (1993); Blanco et al., J. Biol. Chem. 268: 16763-16770 (1993); U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617; U.S. patent application Ser. No. 12/748,359, now published as U.S. Patent Publication No. 20110014612.

In some embodiments, the disclosure also relates to modes for analyzing, including for example sequencing, nucleic acids using reactions that involve interdependent nucleotide incorporation and nucleotide excision. As used herein, interdependent nucleotide incorporation and nucleotide excision means that both reactions occur on the same nucleic molecule at contiguous sites on the nucleic acid, and one reaction facilitates the other. An example of such a reaction is a nick translation reaction. A nick translation reaction, as used herein, refers to a reaction catalyzed by a polymerase enzyme having 5' to 3' exonuclease activity, that involves incorporation of a nucleotide onto the free 3' end of a nicked region of double stranded DNA and excision of a nucleotide located at the free 5' end of the nicked region of the double stranded DNA. Nick translation therefore refers to the movement of the nicked site along the length of the nicked strand of DNA in a 5' to 3' direction. As will be recognized by those of ordinary skill in the art, the nick translation reaction includes a sequencing-by-synthesis reaction based on the intact strand of the double stranded DNA. This strand acts as the template from which the new strand is synthesized. The method does not require the use of a primer because the double stranded DNA can prime the reaction independently. While the disclosure (including the following passages) may often refer to "nick translation" for the sake of brevity, it is to be understood that the scope of this disclosure includes any other combined reaction of nucleotide excision and incorporation to be used in place of traditional nick translation.

The nick translation approach has two features that make it well suited for use in the nucleotide incorporation and sequencing methods provided herein. First, the nick translation reaction results in the release of two hydrogen ions for each combined excision/incorporation step, thereby providing a more robust signal at the chemFET each time a nucleotide is incorporated into a newly synthesized strand. A sequencing-by-synthesis method, in the absence of nucleotide excision, releases one hydrogen ion per nucleotide incorporation. In contrast, nick translation releases a first hydrogen ion upon incorporation of a nucleotide and a second hydrogen ion upon excision of another nucleotide. This increases the signal that can be sensed at the chemFET, thereby increasing signal to noise ratio and providing a more definitive readout of nucleotide incorporation.

Second, the use of a double stranded DNA template (rather than a single stranded DNA template) results in less interference of the template with released ions and a better signal at the chemFET. A single stranded DNA has exposed groups that are able to interfere with (for example, sequester) hydrogen ions. These reactive groups are shielded in a double stranded DNA where they are hydrogen bonded to complementary groups. By being so shielded, these groups do not substantially impact hydrogen ion level or concentration. As a result, signal resulting from hydrogen ion release is greater in the presence of double stranded as compared to single stranded templates, as will be signal to noise ratio, thereby further contributing to a more definitive readout of nucleotide incorporation.

Templates suitable for nick translation typically are completely or partially double stranded. Such templates comprise an opening (or a nick) which acts as an entry point for a polymerase. Such openings can be introduced into the template in a controlled manner as described below and known in the art.

As will be appreciated by one of ordinary skill in the art, it is preferable that these openings be present in each of the plurality of identical templates at the same location in the template sequence. Typical molecular biology techniques involving nick translation use randomly created nicks along the double stranded DNA because their aim is to produce a detectably labeled nucleic acid. These prior art methods generate nicks through the use of sequence-independent nicking enzymes such as DNase I. In many methods, however, the nick location must be known, non-random and uniform for all templates of identical sequence. Various ways of achieving this are known in the art, and some of these are discussed below by way of non-limiting examples.

Another example of a suitable nick translation template is a self-priming nucleic acid. The self priming nucleic acid may comprise a double stranded and a single stranded region that is capable of self-annealing in order to prime a nucleic acid synthesis reaction. The single stranded region is typically a known synthetic sequence ligated to a nucleic acid of interest. Its length can be predetermined and engineered to create an opening following self-annealing, and such opening can act as an entry point for a polymerase.

It is to be understood that, as the term is used herein, a nicked nucleic acid, such as a nicked double stranded nucleic acid, is a nucleic acid having an opening (e.g., a break in its backbone, or having abasic sites, etc.) from which a polymerase can incorporate and optionally excise nucleotides. The term is not limited to nucleic acids that have been acted upon by an enzyme such as a nicking enzyme, nor is it limited simply to breaks in a nucleic acid backbone, as will be clear based on the exemplary methods described herein for creating such nucleic acids.

Once the nicked double stranded nucleic acids are generated, they are then subjected to a nick translation reaction. If the nick translation reaction is performed to sequence the template nucleic acid, the nick translation can be carried out in a manner that parallels the sequencing-by-synthesis methods described herein. More specifically, in some embodiments each of the four nucleotides is separately contacted with the nicked templates in the presence of a polymerase having 5' to 3' exonuclease activity. In other embodiments, known combinations of nucleotides are used. Examples of suitable enzymes include DNA polymerase I from E. coli, Bst DNA polymerase, and Taq DNA polymerase. The order of the nucleotides is not important as long as it is known and preferably remains the same throughout a run. After each nucleotide is contacted with the nicked templates, it is washed out followed by the introduction of another nucleotide, just as described herein. In the nick translation embodiments, the wash will also carry the excised nucleotide away from the chemFET.

It should be appreciated that just as with other aspects and embodiments described herein the nucleotides that are incorporated into the nicked region need not be extrinsically labeled since it is a byproduct of their incorporation that is detected as a readout rather than the incorporated nucleotide itself. Thus, the nick translation methods may be referred to as label-free methods, or fluorescence-free methods, since incorporation detection is not dependent on an extrinsic label on the incorporated nucleotide. The nucleotides are typically naturally occurring nucleotides. It should also be recognized that since the methods benefit from the consecutive incorporation of as many nucleotides as possible, the nucleotides are not for example modified versions that lead to premature chain termination, such as those used in some sequencing methods.

EXAMPLES

Example 1. Design and Expression of Modified Bst DNA Polymerases

The amino acid sequence of the large fragment of the Bst DNA polymerase, having the amino acid sequencing of SEQ ID NO: 1, was analyzed using both H++ and PropKa to calculate the pKas of titratable side chains within the folded protein structure. Tables 2 and 3 show the calculated pKas for amino acids within Bst DNA polymerase. Column 1 shows the amino acid residue, with numbering based upon that of SEQ ID NO:1; column 2 shows the calculated pKa of the side chain. Column 3 indicates whether the residue is accessible on the surface of the protein (S) or buried (B), as determined by a review of the protein structure. The values shown in Table 2 were determined using PropKa, while the values in Table 3 were determined using H++.

Amino acid residues having calculated pKas within the range of about pH 6 to about pH 8.0 as determined by either algorithm were targeted for substitution. A nucleic acid sequence encoding the large fragment of Bst DNA polymerase (having the amino acid sequence of SEQ ID NO: 1) was mutated using conventional techniques to introduce the following amino acid substitutions into the encoded protein product: His46Arg, Glu446Gln, and His572Arg. The resulting amino acid sequence is shown in SEQ ID NO: 2. The substituted amino acids are underlined and in bold.

SEQ ID NO: 2
MAKMAFTLADRVTEEMLADKAALVVEVVEENYHDAPIVGIAVVNERGRFF

LRPETALADPQFVAWLGDETKKKSMFDSKRAAVALKWKGIELCGVSFDLL

LAAYLLDPAQGVDDVAAAAKMKQYEAVRPDEAVYGKGAKRAVPDEPVLAE

HLVRKAAAIWELERPFLDELRRNEQDRLLVELEQPLSSILAEMEFAGVKV

DTKRLEQMGKELAEQLGTVEQRIYELAGQEFNINSPKQLGVILFEKLQLP

VLKKTKTGYSTSADVLEKLAPYHEIVENILHYRQLGKLQSTYIEGLLKVV

RPDTKKVHTIFNQALTQTGRLSSTEPNLQNIPIRLEEGRKIRQAFVPSES

DWLIFAADYSQIELRVLAHIAEDDNLMEAFRRDLDIHTKTAMDIFQVSED

EVTPNMRRQAKAVNFGIVYGISDYGLAQNLNISRKEAAEFIERYFQSFPG

VKRYMENIVQEAKQKGYVTTLLHRRRYLPDITSRNFNVRSFAERMAMNTP

IQGSAADIIKKAMIDLNARLKEERLQAHLLLQVHDELILEAPKEEMERLC

RLVPEVMEQAVTLRVPLKVDYRYGSTWYDAK

The nucleic acid sequence encoding SEQ ID NO: 2 was further mutated using conventional techniques to create nucleic acid sequences encoding polymerases having additional mutations. SEQ ID NO: 3 contains two further amino acid substitutions as compared to SEQ ID NO:2: His473Arg and His528Ala. Thus SEQ ID NO: 3 contains a total of five amino acid substitutions as compared to the reference wild-type sequence of SEQ ID NO:1. The substituted amino acids as compared to SEQ ID NO: 1 are underlined and in bold.

SEQ ID NO: 3
MAKMAFTLADRVITEMLADKAALVVEVVEENYHDAPIVGIAVVNERGRFF

LRPETALADPQFVAWLGDETKKKSMFDSKRAAVALKWKGIELCGVSFDLL

LAAYLLDPAQGVDDVAAAAKMKQYEAVRPDEAVYGKGAKRAVPDEPVLAE

HLVRKAAAIWELERPFLDELRRNEQDRLLVELEQPLSSILAEMEFAGVKV

-continued

```
DTKRLEQMGKELAEQLGTVEQRIYELAGQEFNINSPKQLGVILFEKLQLP

VLKKIKTGYSTSADVLEKLAPYHEIVENILHYRQLGKLQSTYIEGLLKVV

RPDTKKVHTIFNQALTQTGRLSSTEPNLQNIPIRLEEGRKIRQAFVPSES

DWLIFAADYSQIELRVLAHIAEDDNLMEAFRRDLDIHTKTAMDIFQVSED

EVIPNMRRQAKAVNFGIVYGISDYGLAQNLNISRKEAAEFIERYFQSFPG

VKRYMENIVQEAKQKGYVTILLRRRRYLPDITSRNFNVRSFAERMAMNIP

IQGSAADIIKKAMIDLNARLKEERLQAALLLQVHDELILEAPKEEMERLC

RLVPEVMEQAVTLRVPLKVDYRYGSTWYDAK
```

SEQ ID NO: 4 contains three additional amino acid substitutions as compared to SEQ ID NO:3: His281Ala, His273Arg, and Tyr477Phe. Thus SEQ ID NO: 4 contains a total of eight amino acid substitutions as compared to the reference wild-type sequence of SEQ ID NO:1. The substituted amino acids as compared to SEQ ID NO: 1 are underlined and in bold.

```
                                            SEQ ID NO: 4
MAKMAFTLADRVTEEMLADKAALVVEVVEENYHDAPIVGIAVVNERGRFF

LRPETALADPQFVAWLGDETKKKSMFDSKRAAVALKWKGIELCGVSFDLL

LAAYLLDPAQGVDDVAAAAKMKQYEAVRPDEAVYGKGAKRAVPDEPVLAE

HLVRKAAAIWELERPFLDELRRNEQDRLLVELEQPLSSILAEMEFAGVKV

DTKRLEQMGKELAEQLGTVEQRIYELAGQEFNINSPKQLGVILFEKLQLP

VLKKTKTGYSTSADVLEKLAPYREIVENILAYRQLGKLQSTYIEGLLKVV

RPDTKKVHTIFNQALTQTGRLSSTEPNLQNIPIRLEEGRKIRQAFVPSES

DWLIFAADYSQIELRVLAHIAEDDNLMEAFRRDLDIHTKTAMDIFQVSED

EVTPNMRRQAKAVNFGIVYGISDYGLAQNLNISRKEAAEFIERYFQSFPG

VKRYMENIVQEAKQKGYVTTLLRRRRFLPDITSRNFNVRSFAERMAMNTP

IQGSAADIIKKAMIDLNARLKEERLQAALLLQVHDELILEAPKEEMERLC

RLVPEVMEQAVTLRVPLKVDYRYGSTWYDAK
```

The mutated nucleic acid sequences encoding SEQ ID NO: 2, SEQ ID NO: 3 and SEQ ID NO: 4 were expressed in an *E. coli* host, and the modified proteins were purified using conventional techniques.

Example 2: Determination of Candidate Amino Acids for Modification in *E. Coli* SSB The amino acid sequence of the single stranded DNA binding protein of *E coli* having the amino acid sequence of SEQ ID NO: 19 was analyzed using PropKa.

The calculated pKas of the amino acid residues having titratable side chains are shown in Table 4.

Amino acid residues having calculated pKa values within the range of about pH 4.0 to about pH 10.0 are targeted for substitution. Modified SSB proteins comprising these substitutions are generated, expressed and purified using conventional methods.

Example 3: Determination of Candidate Amino Acids for Modification in KOD DNA Polymerase The amino acid sequence of the Therminator™ DNA polymerase (SEQ ID NO: 5) is shown below:

```
                                            (SEQ ID NO: 5)
MILDTDYITENGKPVIRVFKKENGEFKIEYDRTFEPYFYALLKDDSAIED

VKKVTAKRHGTVVKVKRAEKVQKKFLGRPIEVWKLYFNHPQDVPAIRDRI

RAHPAVVDIYEYDIPFAKRYLIDKGLIPMEGDEELTMLAFDIETLYHEGE

EFGTGPILMISYADGSEARVITWKKIDLPYVDVVSTEKEMIKRFLRVVRE

KDPDVLITYNGDNFDFAYLKKRCEELGIKFTLGRDGSEPKIQRMGDRFAV

EVKGRIHFDLYPVIRRTINLPTYTLEAVYEAVFGKPKEKVYAEEIAQAWE

SGEGLERVARYSMEDAKVTYELGREFFPMEAQLSRLIGQSLWDVSRSSTG

NLVEWFLLRKAYKRNELAPNKPDERELARRRGGYAGGYVKEPERGLWDNI

VYLDFRSLYPSIIITHNVSPDTLNREGCKEYDVAPEVGHKFCKDFPGFIP

SLLGDLLEERQKIKRKMKATVDPLEKKLLDYRQRAIKILANSFYGYYGYA

KARWYCKECAESVTAWGREYIEMVIRELEEKFGFKVLYADIDGLHATIPG

ADAETVKKKAKEFLKYINPKLPGLLELEYEGFYVRGFFVIKKKYAVIDEE

GKITTRGLEIVRRDWSEIAKETQARVLEAILKHGDVEEAVRIVKEVTEKL

SKYEVPPEKLVIHEQIIRDLRDYKATGPHVAVAKRLAARGVKIRPGIVIS

YIVLKGSGRIGDRAIPADEFDPIKHRYDAEYYIENQVLPAVERILKAFGY

RKEDLRYQKTKQVGLGAWLKVKGKK
```

The amino acid sequence of Therminator™ polymerase (SEQ ID NO: 5) was analyzed using PropKa. The calculated pKas of the amino acid residues having titratable side chains of the Therminator™ polymerase are shown in Table 5. Column 1 shows the amino acid residue; column 2 shows the pKa of the amino acid residue in the protein as calculated by PropKa; and column 3 shows the model pKa value for the amino acid in solution.

Amino acid residues having calculated pKa values within the range of about pH 4.0 to about pH 10.0 are targeted for substitution employed any of the principles of selection and modification described herein. Nucleic acid sequences encoding the resulting modified polymerases comprising these substitutions are synthesized, cloned, expressed and purified using conventional genetic engineering methods.

```
                                            (SEQ ID NO: 19)
  1    ASRGVNKVILVGNLGQDPEVRYMPNGGAVANITLATSESWRDKATGEMKEQTEWHRVVLF

61    GKLAEVASEYLRKGSQVYIEGQLRTRKWTDQSGQDRYTTEVVVNVGGTMQMLGGRQGGGA

121    PAGGNIGGGQPQGGWGQPQQPQGGN
```

Example 4: Determination of Candidate Amino Acids for Modification in KOD DNA Polymerase The amino acid sequence of the KOD DNA polymerase (SEQ ID NO: 6) was analyzed using PropKa.

```
                                              (SEQ ID NO: 6)
MILDTDYITEDGKPVIRIFKKENGEFKIEYDRIFEPYFYALLKDDSAIEE

VKKITAERHGTVVIVKRVEKVQKKFLGRPVEVWKLYFTHPQDVPAIRDKI

REHPAVIDIYEYDIPFAKRYLIDKGLVPMEGDEELKMLAFDIETLYHEGE
```

-continued
```
EFAEGPILMISYADEEGARVITWKNVDLPYVDVVSTEREMIKRFLRVVKE

KDPDVLITYNGDNFDFAYLKKRCEKLGINFALGRDGSEPKIQRMGDRFAV

EVKGRIHFDLYPVIRRTINLPTYTLEAVYEAVFGQPKEKVYAEEITTAWE

IGENLERVARYSMEDAKVIYELGKEFLPMEAQLSRLIGQSLWDVSRSSIG

NLVEWFLLRKAYERNELAPNKPDEKELARRRQSYEGGYVKEPERGLWENI

VYLDFRSLYPSIIITHNVSPDILNREGCKEYDVAPQVGHRFCKDFPGFIP

SLLGDLLEERQKIKKKMKATIDPIERKLLDYRQRAIKILANSYYGYYGYA

RARWYCKECAESVTAWGREYITMTIKEIEEKYGFKVIYSDIDGFFATIPG

ADAETVKKKAMEFLKYINAKLPGALELEYEGFYKRGFFVIKKKYAVIDEE

GKITTRGLEIVRRDWSEIAKETQARVLEALLKDGDVEKAVRIVKEVTEKL

SKYEVPPEKLVIHEQIIRDLKDYKATGPHVAVAKRLAARGVKIRPGIVIS

YIVLKGSGRIGDRAIPFDEFDPIKHKYDAEYYIENQVLPAVERILRAFGY

RKEDLRYQKTRQVGLSAWLKPKGT
```

The calculated pKas of the amino acid residues having titratable side chains are shown in Table 6. Column 1 shows the amino acid residue; column 2 shows the pKa of the amino acid residue in the protein as calculated by PropKa; and column 3 shows the model pKa value for the amino acid in solution.

Amino acid residues having calculated pKa values within the range of about pH 4.0 to about pH 10.0 are targeted for substitution. Modified polymerases comprising these substitutions are generated, expressed and purified using conventional methods.

Example 5: Determination of Candidate Amino Acids for Modification in B103 DNA Polymerase The amino acid sequence of a B103-type polymerase, derived from the published sequence of the DNA polymerase of bacteriophage B103, is shown below as SEQ ID NO: 7.

```
                                                            (SEQ ID NO: 7)
  1 mprkmfscdf etttklddcr vwaygymeig nldnykigns ldefmqwvme iqadlyfhnl 61 kfdgafivnw lehhgfkwsn eglpntynti iskmgqwymi dicfgykgkr klhtviydsl 121 kklpfpvkki akdfqlpllk gdidyhaerp vgheitpeey eyikndieii araldiqfkg 181 gldrmtagsd slkgfkdils tkkfnkvfpk lslpmdkeir rayrggftwl ndkykekeig 241 egmvfdvnsl ypsqmysrpl pygapivfqg kyekdegypl yiqrirfefe lkegyiptiq 301 ikknpffkgn eylknsgaep velyltnvdl eliqehyemy nveyidgfkf rektglfkef 361 idkwtyvkth ekgakkqlak lmlnslygkf asnpdvtgkv pylkedgslg frvgdeeykd 421 pvytpmgvfi tawarfttit aaqacydrii ycdtdsihlt gtevpeiikd ivdpkklgyw 481 ahestfkrak ylrqktyiqd iyakevdgkl iecspdeatt tkfsvkcagm tdtikkkvtf 541 dnfrvgfsst gkpkpvqvng gvvlvdsvft ik
```

Further details regarding the B103-type polymerase of SEQ ID NO: 7 can be found in U.S. Patent Publication No. 20110014612.

Mutations to the B103-type DNA polymerase of SEQ ID NO: 7 to remove potential buffering side chains and thereby reduce the buffering capacity of the B103-type polymerase may include replacement of any one or more histidine residues with arginine and/or replacement of any one or more glutamic acid residues with alanine, as shown in Table 7. Mutations may further include replacement of any one or more cysteine residues with serine, also as shown in Table 7.

Optionally, the modified B103-type polymerase can also include the amino acid sequence of SEQ ID NO: 7 and further include the amino acid substitution D166A, which reduces 3' to 5' exonuclease activity. The reduction or elimination of exonuclease activity can be helpful in applications involving the detection of nucleotide incorporation, such as ion-based nucleic acid sequencing.

The amino acid sequence of the B103-type DNA polymerase of SEQ ID NO: 7 is highly homologous to the DNA polymerase of the bacteriophage Phi29, as shown in SEQ ID NO: 18.

```
                                                             (SEQ ID NO: 18)
  1   MKHMPRKMYS  CAFETTTKVE  DCRVWAYGYM  NIEDHSEYKI  GNSLDEFMAW  VLKVQADLYF

61   HNLKFAGAFI  INWLERNGFK  WSADGLPNTY  NTIISRMGQW  YMIDICLGYK  GKRKIHTVIY

121   DSLKKLPFPV  KKIAKDFKLT  VLKGDIDYHK  ERPVGYKITP  EEYAYIKNDI  QIIAEALLIQ

181   FKQGLDRMTA  GSDSLKGFKD  IITTKKFKKV  FPTLSLGLDK  EVRYAYRGGF  TWLNDRFKEK

241   EIGEGMVFDV  NSLYPAQMYS  RLLPYGEPIV  FEGKYVWDED  YPLHIQHIRC  EFELKEGYIP

301   TIQIKRSRFY  KGNEYLKSSG  GEIADLWLSN  VDLELMKEHY  DLYNVEYISG  LKFKATTGLF

361   KDFIDKWTYI  KTTSEGAIKQ  LAKLMLNSLY  GKFASNPDVT  GKVPYLKENG  ALGFRLGEEE

421   TKDPVYTPMG  VFITAWARYT  TITAAQACYD  RIIYCDTDSI  HLTGTEIPDV  IKDIVDPKKL

481   GYWAHESTFK  RAKYLRQKTY  IQDIYMKEVD  GKLVEGSPDD  YTDIKFSVKC  AGMTDKIKKE

541   VTFENFKVGF  SRKMKPKPVQ  VPGGVVLVDD  TFTIK
```

The crystal structure of the Phi 29 DNA polymerase is known (Kamtekar et al., EMBO J. 25: 1335-1343 (2006). As the DNA polymerase of B103 is likely to fold into a similar structure as that of Phi29, the sequence of the Phi29 DNA polymerase (SEQ ID NO:18) is analyzed by a program such as PropKa to determine amino acid residues having pKas within the range of about pH 4.0 to about pH 10.0. Substitutions are then made to the corresponding amino acids in the B103 DNA polymerase, as determined using the amino acid sequence alignment shown in FIG. 2.

Modified polymerases comprising any of the above substitutions are generated, expressed and purified using conventional methods.

Example 6: Assay for Non-Buffering Properties of Modified Proteins

The buffering properties of the modified Bst DNA polymerases of SEQ ID NO: 2, SEQ ID NO: 3 and SEQ ID NO: 4 are evaluated by performing a standard titration as known in the art. The titration curves for the modified polymerases are compared to the titration curve for the unmodified protein having the amino acid sequence of SEQ ID NO: 1. Similar titrations are carried out for other modified proteins as described in Examples 2-5.

Example 7: Use of a Modified Bst DNA Polymerase in an Exemplary Ion-Based DNA Sequencing Reaction The modified Bst polymerase of SEQ ID NO: 2 was compared to the unmodified polymerase (SEQ ID NO: 1) in a sequencing reaction using the Personal Genome Machine (PGM™) System (Applied Biosystems, Part Number 4462921) The Personal Genome Machine™ System uses an array of semiconductor sensors to measure hydrogen ions generated when the polymerase adds nucleotides to a DNA template.

The unmodified Bst DNA polymerase having the amino acid sequence of SEQ ID NO: 1 and the modified Bst DNA polymerase having the amino acid sequence of SEQ ID NO: 2 were used to sequence nucleic acid templates using an Ion Torrent PGM™ sequencer. Exemplary instructions for performing ion-based sequencing using the Ion Torrent PGM™ sequencer can be found in the User Guides provided with the Ion Torrent PGM™ 314 Sequencing System (including the PGM™ 314 Library Preparation User Guide, the PGM™ Template Preparation User Guide, and Ion PGM™ 315 Sequencing Chip User Guide and the Ion Torrent PGM™ Sequencing User Guide, all of which are incorporated by reference herein.

Sequencing was performed according to the following exemplary protocol:

Library Preparation

Briefly, the library preparation protocol was used to prepare a DNA library having fragments with sizes having a distribution range of 50-60 bp around a median size of 180-210 bp. Each library fragment is flanked by A and B adapters, allowing subsequent amplification.

The library was prepared essentially using the following steps:

DNA Fragmentation:

The DNA was sheared with the BioRuptor® Sonication System, essentially according to the protocol provided by the manufacturer.

An aliquot of the sonicated DNA was diluted and analyzed on a BioAnalyzer High Sensitivity DNA LabChip® or on an agarose gel to confirm a fragment size range between ~50-500 bp, with a peak around 200 bp.

The fragmented DNA was end-repaired using the buffer and enzyme mix supplied in the Ion Fragment Library Kit essentially using the following steps:

The end-repair reaction mix was prepared according to the following Table and then incubated for 20 minutes at room temperature:

| Component | Volume |
| --- | --- |
| Fragmented DNA (step 5.1.9) | Y μL |
| Nuclease-free Water | 158-Y μL |
| 5X End Repair Buffer | 40 μL |
| End Repair Enzyme | 2 μL |
| Total | 200 |

The DNA was purified with the Agencourt® AMPure® XP Kit.

Adapter Ligation:

The Amplification Adapters provided with the Ion Torrent PGM™ were ligated to the DNA using Ligase enzyme and the provided buffer. The buffer and ligase were mixed with the end-repaired DNA in nuclease free water and let sit at room temperature for 30 minutes.

The DNA was then purified using the Agencourt® AMPure® XP Kit (Beckman Coulter), essentially according to the protocol provided by the manufacturer.

The purified DNA was then size-selected using the Pippin Prep® instrument (SAGE Biosciences), essentially according to the protocol provided by the manufacturer. When the separation was complete, the size-selected DNA was recovered from the Elution Chamber and transferred to a new microcentrifuge tube.

The DNA was then purified using the Agencourt® AMPure® XP Kit (Beckman Coulter), essentially according to the protocol provided by the manufacturer.

Nick-Translation and Amplification:

A nick-translation and amplification reaction mixture was prepared by mixing the DNA and primer mix with Platinum® PCR SuperMix High Fidelity and amplified on a thermocyling block using standard PCR reaction conditions.

The DNA was then purified using the Agencourt® AMPure® XP Kit (Beckman Coulter), essentially according to the protocol provided by the manufacturer.

The library was then linked to washed Dynabeads M-270 Streptavidin beads by incubating the washed beads with the size-selected and purified DNA, and incubating at room temperature with shaking at 8-10 rpm for 20 minutes.

The bead-linked library was washed twice in buffer, then resuspended in Alkali Solution including 0.125N NaOH. The supernatant was collected, neutralized and purified using the sample using the QIAGEN MinElute Column essentially according to the protocol of the manufacturer.

Quality assessment and library quantification was performed the RiboGreen® RNA quantitation kit or the Bio-Analyzer™ RNA 6000 Pico LabChip® essentially according to the protocol of the manufacturer.

Template Preparation

Nucleic acid templates were amplified onto hydrogel matrices ("Ion Spheres", prepared essentially as described in), essentially according to the following protocol:

Determination of Optimal Library Concentration for emPCR

The concentration of the template library was estimated, and the template DNA was diluted to an appropriate concentration. Emulsion PCR was then performed by mixing the following components:

| Reagent | Volume (µL) |
| --- | --- |
| Nuclease-free water | 344 |
| AmpMix | 105 |
| MgCl$_2$ Solution | 105 |
| dNTPs | 105 |
| Primers Mix | 105 |
| TIPP (NEB) | 2 |
| Polymerase | 126 |
| Ion Sphere ™ Particles | 140 |
| Library | 18 |
| Total | 1050 |

The amplification mix was then transferred into an oil phase with shaking. The emulsion was then subjected to PCR amplification using standard thermocycling conditions.

The Ion Sphere Particles including amplified nucleic acid was then recovered by extracting the emulsion with butanol and hexane, and then washing the recovered particles in buffer.

Template-positive Ion Sphere™ particles were enriched by washing the spheres with denaturation solution, incubating with an enrichment primer and washed Dynabeads® MyOne™ Streptavidin C1 beads. The enriched particles were then separated from the Dynabeads® MyOne™ Streptavidin C1 beads using appropriate washes in alkali solution including NaOH.

Sequencing

Amplified nucleic acid templates bound to hydrogel matrices and prepared essentially according to the foregoing protocol were sequencing in the Ion Torrent PGM™ sequencing using the sequencing primer supplied with the sequencing kit. Essentially, the amplified templates on the hydrogel matrices were suspended in sequencing buffer and pipetted into the Ion Torrent 314 Sequencing Chip, which was placed in the Ion Torrent PGM™ Sequencer. The sequencing run was initiated and performed by the PGM™ sequencer. The reagent conditions for sequencing were 6.3 mM NaCl$_2$, 13 mM MgCl$_2$, 0.1% Triton X-100, adjusted to pH 7.5 with NaOH. 1 µl of a 59 µM solution of the polymerase was added to 10M beads per 314 chip sequencing. The nucleotide concentration was 50 uM.

Data Analysis

This section provides an overview of the software modules and concepts applied at various stages of the data processing of the signals gathered during the sequencing reaction. The Torrent Server Analysis Pipeline, the "Pipeline", processes raw acquisition data from a PGM run, and outputs base calls in both SFF and FASTQ file formats. The Torrent Browser provides a web interface to the process, including many metrics, graphs, and reporting features derived from the Pipeline results.

During a PGM™ run, for each nucleotide flow, one acquisition file is generated. Each acquisition file contains the raw signal measurement in each well of the chip for the given nucleotide flow. So each acquisition flow, for a 314 chip, contains roughly 1.5 million separate incorporation events. A series of such acquisition files then represents the roughly 1.5 million possible reads. The analysis pipeline converts these raw signal measurements into incorporation measures, and ultimately into base calls for each read. The raw measurements are the system's conversion of the raw pH value in each well into a voltage converted into a digital representation of that voltage. This measurement over the entire chip occurs many times per second.

The following passages describe briefly the high level modules within the analysis pipeline. Each module accepts specific inputs and produces specific outputs, described in more detail, below.

DAT Processing

The DAT processing module deals directly with raw acquisition files (acq_*.dat).

DAT processing performs the following functions:

Raw Acquisition Data Loading into Memory.

This includes decompressing the data files. Data is compressed when it is streamed off the PGM™. An optional dynamic frame rate compression mode whereby various portions of the incorporation event throughout the nucleotide flow duration are captured at different frame rates. The variable frame rate allows biologically specific events to be captured with high resolution, while at the same time allowing the overall file size to be decreased by allowing multiple frames to be averaged where appropriate. Alternatively, a compression approach may use a keyframe/delta compression technique whereby an initial value is stored, followed by the changes in that initial value, rather than storing the actual value each time. This results in a nearly 2× reduction in file size.

Raw Measurement Offset Corrections:

Raw acquisition data are stored using the values output by the chip. Each well has its own reference value, and to compare well to well, the two wells may use a common reference. The offset correction takes the average of the first few frames within each acquisition file and subtracts that value from each well, thus allowing well measurements to have a common reference value.

Pinned Well Identification:

Due to the nature of the chip output voltages, a range of values exists for any given chip. The PGM instrument calibration code brings the majority of wells within range of the hardware's analog to digital converters. The output is a distribution of values centered around the center voltage. Wells that reside outside a selected distribution are considered 'pinned' (functional wells outside of the range of the ADC). These pinned wells typically represent less than one percent of the total available wells.

Excluded Wells:

Various flow cell configurations often make tradeoffs on flow velocity profiles and chip coverage areas. For the 314 chip, for example, a percentage of the wells are covered by the flow cell and are not fluidically addressable. A mask is loaded, per chip type, to mark those wells as excluded so they do not complicate down-stream processing of the chip.

Classification

Classification is the process of determining the contents of each well on the chip. The following describes the classification decision tree: A well can either be empty, or contain a particle. For wells containing a particle, the process additionally determines if that particle is: (a) A library particle; (b) A test fragment (control) particle; (c) A dud particle (a particle that does not produce a sufficiently strong sequence signal); or (d) An ambiguous particle (a particle where it appears to the software as both a test fragment and a library fragment). It is important to note at this point that classification is not simply processing the entire chip as one group. As will be mentioned for other pipeline modules, the chip is processed in smaller regions. A 314 chip, for example, is segmented into 50×50 well regions, resulting in about 625 total regions. This allows processing many small regions in parallel and taking advantage of multi-core/multi-process compute nodes that have such capabilities. More importantly, regions in the chip are processed that contain fluidically similar wells, where smaller regions tend to be relatively homogeneous and allow comparison of wells to each other within a region.

Default Sequencing Keys and Flow Order

The next part of the classification module involves identifying particle wells as test fragments (TF) or library fragments. To understand this part of the algorithm, the concept of 'keys' and flow order must first be understood. Table 8, below shows the default library and TF sequencing keys, in both base-space and in flow-space for the given default flow order TACG.

TABLE 8

|  | Base-space | Flow order TACG vector |
| --- | --- | --- |
| Library Key | TCAG | 1010010X |
| TF Key | ATCG | 0100101X |

The 'X' in the vector, above, indicates that the value is at least a one, but could in fact be higher because the next base after the key could also match, thus creating a longer homopolymer.

Separation

Once the particles have been identified within the wells, separation is then performed. In this step, the two sequencing keys are used to compare each read. The well is determined to contain a bead; the flows are converted into a sequence and tested against each key. Because the test is performed against both keys, the number of flows needed to sequence each key is determined, and the lower number of the two is used. Adding many more bases to one of the two keys will not always result in better separation since the shorter of the two drives the number of flows ultimately used.

With the default keys and flow order, above, there are two vectors:

TACGTACG
1010010
0100101

Here, valid comparison nucleotide pairs are then searched for. This means that to compare two sequences, the following rules need to be satisfied: (1) That there is a 0-mer and a 1-mer event for each nucleotide in the key; and (2) That there is the 1-mer from one key firing during the 0-mer event in the other nucleotide.

When both rules are satisfied for a given nucleotide, there is a separator 'event' to be used. The more 'events' there are, the better the two keys can be separated. In other words, the nucleotide pairs are orthogonal in flow-space for the two keys, as in the bold vertical highlighted pairs:

'T' nuc satisfies our rules:
1010010
0100101

Above, for the 'T' nuc flow, the library key incorporates on the first flow, and has a 0-mer on the second 'T' flow, whereas the TF key has the opposite.

A similar case is observed for the 'A' nucleotide, and the 'C' nucleotide. The 'G' nucleotide cannot be used because there is no 1-mer event observed until the 8th flow. That flow cannot be included because that 'G' in the library can be part of a larger homopolymer stretch. Thus, it cannot be guaranteed that there is exactly a 1-mer in that flow. Further, the TF key does not have a 1-mer in the first 'G' flow, but has a 0-mer 'G' in the first 'G' flow which is the same as the library key.

'A' nucleotide satisfies these rules:
1010010
0100101

'C' nucleotide satisfies these rules:
1010010
0100101

Mask

The output of the classification module is a mask object (and file as bfmask.bin) that contains bit flags for each well, indicating the contents of each well.

Signal Processing

The signal processing module focuses on wells containing particles, which is now using the mask information in addition to the raw acquisition data. A signal is measured in a well during an incorporation event. The signal has additional components, referred to as 'the background'. This background part of the signal is present during each flow and can vary over time, across the chip, and during an acquisition. The signal processing problem can be thought of as having two parts. The first part involves deriving the background signal that would have been measured in a given well, had no incorporation occurred. The second part involves subtracting (or fitting) the background signal and examining (or fitting to) the remaining signal. The output of the incorporation fitting model produces the estimate of the incorporation at each nucleotide flow for each well.

At this point, the output from the analysis pipeline is a raw incorporation signal measure per well, per flow, stored as a 1.wells file.

Basecalling

The basecaller module performs signal normalizations, phase and droop estimations, signal corrections, and declares bases for each flow of each well. It outputs non-incorporation events in addition to incorporation events. The SFF output file stores all such calls.

Normalization

Normalization is performed on each read. Normalization is a way of using the known expected 1-mer signals produced by sequencing through the key, and using those signals to establish the 1-mer average signal. This is initially a process using the raw measurements from the signal processing module. As the basecaller processes each well, more bases are accurately determined and additional measurements can then be used to re-normalize the raw measured signals to gain higher confidence, a higher signal-to-noise ratio (SNR), in the normalization of each well.

Droop Estimation

Observed signal droop can be attributed to DNA polymerase loss that can occur during a sequencing run. Typically, such loss is experienced only during incorporation events, and typical values are in the 0.1 to 0.2% range over the course of a run. By averaging groups of reads in a region together and averaging their measured signals (after normalization), an exponential can be fit to the resulting curve, and the rate of signal loss over time is extracted. Thus, an estimate of the polymerase loss during incorporation events can be determined.

Phase Estimation

Once the droop has been established, it is used in the phase model as a constant for each read. Droop estimates can still vary across the chip, but is assumed fixed for each processed region. The model then fits the carry-forward and incomplete extension parameters for each read, over a limited number of flows and excluding certain flows. The output from this fit is an estimate of the carry-forward (CF) and incomplete extension (IE) for each well. The values are averaged over small regions to reduce errors and noise in the fit. The output CF and IE values are used as inputs to the solver.

Solver

The solver part of the base caller applies the phase and droop estimates to the normalized signals and makes predictions of the likely measured values for each flow for probable incorporation events. By comparing the actual measured value to the list of predicted values, the best fit prediction at each flow is then used as the base call for that flow. So, a 0-mer, 1-mer, 2-mer, etc. can be predicted at each flow. This process continues over the entire read. At the end of one pass, a good estimate of all bases for that read have now been made. The solver then iterates over the read again, applying the same phase and droop estimates at each flow, and refines the base calls. This refining is beneficial since knowledge of future bases on future flows can now be included in the model to more accurately account for carry-forward effects.

Read Filtering and Trimming

Read filtering involves generation of various quality metrics for each base call, quality metrics for each read, and using those metrics to filter out low quality reads and trim reads back to acceptable quality levels. Additionally, adapter trimming is performed on the ends of each read.

Filtering

Filtering reads involves calculating an overall quality metric representing the base caller's ability to accurately correct and base call the raw signals. Reads that have calculated low quality are not written to the SFF file. Low quality reads are typically mixed reads or very low copy-count reads that produce low quality sequence such that they do not fit the expected incorporation model.

Briefly, the Ion Torrent PGM™ system applies some quality checks to sequence reads before writing them out. Reads are tested to see if they are possibly the result of mixed DNA templates on a single Ion Sphere particle in a given well, or if they are generally of low signal quality. The 3' ends of reads are scanned for matches to the adapter sequence and for regions of trailing low quality. Only the high-quality portions of reads passing through these checks are written out to the SFF and FASTQ files.

When processing data from the Personal Genome Machine (PGM™), the identification and removal of low-quality or uncertain base calls is an important consideration for delivering accurate results. In the Torrent Suite analysis software, low-quality bases are removed from the output by: (a) Filtering out entire reads; (b) Trimming low-quality 3' ends of reads.

The operations described in the following passages are applied as post-processing operations after the initial base calls have been estimated.

Read Filtering

The goal of read filtering is the removal of reads that are estimated to comprise low-quality base calls. The kinds of read filters include: (1) A read filter targeted at removal of reads that are derived from wells with non-clonal DNA template populations (i.e. mixtures of different DNA templates); (2) A read filter targeted at reads that are generally a poor fit to the basecalling model's expectations for high-quality data.

Removal of Mixed-Template Reads

Sometimes the DNA template that ends up being amplified on the Ion Sphere particle is derived from multiple different input DNA templates. Possible ways in which this can occur include the presence of two or more distinct DNA fragments in the vesicle at the start of the emulsion PCR stage, or the collapsing together of different emulsion vesicles.

In the usual scenario, each particle gets a single DNA template species amplified onto it, in which case approximately half of the nucleotide flows should result in a positive incorporation (assuming a 4-base flow cycle and uniform and random nucleotide content in the genome). When a particle contains multiple different DNA templates, the number of flows in which a positive incorporation signal can be expected increases substantially.

An effective way to identify possible mixed template reads is to search for reads in which an unusually large proportion of flows are estimated to have a nucleotide incorporation event. As of version 1.1.0 of the Torrent Suite software, the percentage of positive flows (PPF) is evaluated over the first 60 flows (including the key flows). If the PPF value is greater than 60%, the read is excluded before writing out the SFF and FASTQ results. In runs with fewer than 60 flows, the PPF is evaluated over however many flows are available.

One implication of this PPF filter is that certain sequences may not be called by the software. For example, a long sequence that is in exactly the flow order TACG would be expected to have a positive incorporation on every flow and as a result would be filtered out. However in practice sequences like this are rare and the benefits of excluding low-quality reads resulting from mixed templates are favored over excluding a small proportion of genuine reads.

One exception to this approach pertains to test fragments, some of which are designed with sequences that do not typically occur naturally and that have a large expected PPF value. By default, the software does not apply the PPF filter to test fragment reads.

Removal of Lower Quality Reads

The basecalling model has certain expectations about the signal distribution for well-behaved reads. Once the amount of incomplete extension (IE) and carry forward (CF) phasing effects have been estimated there are certain expectations for how signals in neighboring flows should be elevated or depressed. For example, when there is positive IE in effect, a large homopolymer run should result in a depressed signal value in the flow corresponding to the homopolymer and an elevated signal value in the next flow of the same nucleotide.

As part of the basecalling model the observed signal value is compared with what the basecalling model predicted in each flow for each read. The difference between these two quantities (observed value minus predicted value) is referred to as the flow residual for the well and flow in question. In general, a high-quality read which is well-described by the basecalling model and the DNA sequence that it estimates should have low residual values.

The median absolute value of the residual over the initial flows is tracked for each read as a measure of the agreement between observed data and basecalling model. If the median absolute residual is greater than a certain threshold, then the read is considered to be untrusted and it is not written to the SFF and FASTQ output files.

As of version 1.1.0 of the Torrent Suite software the median absolute residual is computed over the first 60 flows (including key flows) and the threshold above which a read is rejected is 0.13.

The median absolute residual filter is applied for both library and test-fragment reads.

Trimming

The goal of read trimming is the removal of undesired base calls at the 3' end of a read. Such undesired base calls come from: (a) High-quality base calls on reads that have read all the way through the library insert into the B-adapter; and (b) Low-quality base calls at the 3' end of the read.

Two filters are applied to trim reads, one targeted at each of the two categories of undesirable 3' bases. Each filter is applied separately and the read length is taken as the shorter of the two. If the resulting trimmed length is shorter than the minimum read length, the read is filtered out entirely, otherwise the read is written to the SFF and the FASTQ files.

As long as trimming does not reduce the read length below the minimum designated allowable length (four bases as of version 1.1.0 of the software), the flow values and base calls for the entire read are written into the SFF, regardless of the trimmed length. The trimming information is represented in the designated fields in the SFF file.

Removal of Adapter Sequence

Trailing adapter sequence is trimmed out by searching the read for candidate matches to the known adapter sequence in flow-space.

The basecaller works by reversing the effects of CF and IE, producing a phase-corrected ionogram that is stored in the SFF file. If a read extends into the B-adapter, the 3' end of this phase-corrected ionogram will exhibit a pattern that is characteristic of the adapter sequence.

Adapter trimming is accomplished by testing each position in the phase-corrected ionogram to see how well it matches the pattern expected for the adapter. The test computes the Euclidean distance between the phase-corrected ionogram at the tested position and the known ionogram for the adapter. If this distance falls below a fixed threshold, the corresponding position (translated from flow-space back to read-space) is recorded as the adapter trim location; otherwise, the read is considered not to have a match to the adapter. As of version 1.1.0 of the Torrent Suite software, the threshold used is a Euclidean distance of 5.

Removal of Lower-Quality 3' Ends

The distribution of quality scores within Ion Torrent reads is such that the highest quality calls tend to occur at the start of the read where phase errors are smallest in magnitude. For reads that run into low-quality bases before reaching the end of the template, it is helpful to trim away the lower-quality calls at the 3' end. The quality trimming is performed using the per-base quality scores (described further below)

The approach is to scan along the bases of the read computing a moving average in a fixed-length window, and to set the read trim point to just before the earliest (5'-most) base at which the moving average of the per-base quality scores drops below some fixed threshold.

As of version 1.1.0 of the Torrent Suite software the window size is set to 30 bases and the threshold below which the trimming occurs is a quality score of nine.

Quality and Adapter Trimming

Using processing algorithms, a read can be trimmed back until an acceptable level of quality persists for the entire read. A read is also examined to determine if the B-Primer adapter sequence or a portion thereof can be identified with high confidence within the read. If a matching sequence is found, the read is trimmed to the base immediately prior to the start of the adapter.

Trimmed SFF File

The output of this stage is an SFF file that contains only the filtered reads and, for each read, the adapter and quality trimming markers are set appropriately. It is this file that is used to generate the FASTQ file.

Alignment QC

The alignment QC stage involves alignment of reads produced by the pipeline to a reference genome, and extracting metrics from those alignments. Currently, the TMAP aligner is used to align reads. As inputs to the aligner, some or all of the reads produced in the pipeline are used, along with the reference genome and index files. The output is a SAM file. This output SAM file is processed to extract various quality metrics, including estimates of Q17 or Q20 bases, estimates of number of reads at or above 100Q17. The results of the Alignment QC module are viewable using the Torrent Browser web interface in the Reports summary page. The key output component is the SAM file.

The following table shows the files output at each stage or module, along with their expected size for a typical 314 chip library run:

TABLE 9

| Module/Stage | File type | Typical 314 run size |
| --- | --- | --- |
| DAT Processing | *.dat | 53 GB |
| Classification | bfmask.bin | 3 MB |
| Signal Processing | 1.wells | 1237 MB |
| Basecalling | SFF | 515 MB |
| Read Filtering and Trimming | SFF, FASTQ | 515 MB, 122 MB |
| Alignment QC | SAM | 183 MB |

Per-Base Quality Scoring

Per-base quality scores are assigned to each read, and written to the SFF file along with the read itself. The per-base quality scores are assigned by calculating various metrics for the read and using those metrics as lookup indexes into a pre-defined quality lookup table established through prior system training. The metrics often involve estimates of accuracy at the current base, flow, and earlier or later bases or flows for each read.

The Ion Torrent per base quality score system uses a phred-like lookup table to predict quality. The lookup table is generated in training from a representative data set and used to predict the quality of PGM data on a per base basis. Quality scores are published in the SFF, FASTQ and SAM files.

The quality score system includes: (1) A phred-like per base lookup table; and (2) A training system to generate the lookup table.

From read flow values, several quality predictors are calculated for each base in the read. These predictors are used as part of an index to lookup an appropriate quality score for the base in the phred lookup table. See, e.g., Brockman et al. (2008): "Quality scores and SNP detection in sequencing-by-synthesis systems." Genome Res. 18: 763-770; Ewing B, Hillier L, Wendl M C, Green P. (1998): "Base-calling of automated sequencer traces using phred. I. Accuracy assessment." Genome Res. 8(3):175-185; Ewing B, Green P. (1998): "Base-calling of automated sequencer traces using phred. II. Error probabilities." Genome Res. 8(3):186-194.

A training system uses the quality predictors to derive the lookup table.

Training System

To generate a lookup table a representative data set is selected as a training set. The training system uses the following six predictors to capture the majority of features that correlate with and indicate quality:

TABLE 10

Six Predictors used to capture features correlating with and indicating quality

P1 Base position within the read from the start of the sequence.
P2 Local noise in the immediate neighborhood (plus/minus 1 base) of the given base: P2 = max [abs(flowval[base]) − round(flowval[base])].
P3 Read noise as a peak-normalized expression of the mean and standard deviation of all 0-mers and 1-mers in the read: P3 = − (m1 − m0 − s1 − s0)/m1.
P4 Multiple incorporations: In case of multiple incorporations of the same nucleotide in one flow, the last base in the incorporation order is assigned a value equivalent to the total number of incorporations. All other bases in the sequence of the multiple incorporations are assigned the value 1.
P5 Phase error: The number of incorporations of the same nucleotide in the previous flow.
P6 Environment noise in the larger neighborhood (plus/minus 10 bases) of the given base: P6 = max [abs(flowval[base]) − round(flowval[base])].

The quality predictors are calculated from the flow values for each base. Together with TMAP-aligned reads as input, the system establishes these six predictors, along with whether or not the base was called correctly. This vector of one "match" boolean plus six predictors for each base is used as the input into a training system. The predictors are binned, and an extensive list of all combinations with their empirical quality score is recorded. An algorithm is used to summarize predictor values that correspond to the same quality and to select a representative subset of these combinations.

The output of the training and selection algorithm is a lookup table in which each predictor is used as part of an index into the table to look up the phred-like per base quality score at that location.

The Lookup Table

The lookup table is used to assign per base quality scores independent of alignment. The six quality predictors are calculated for each base sequenced by the PGM. The corresponding per base quality is located in the lookup table by finding the first line for which all six calculated predictors are less than or equal to the predictor values in the table. The lookup quality is read from the same line. This process occurs automatically as part of the standard analysis.

Pipeline Implementation

The Ion Torrent pipeline processes the signal from each pixel on the chip, applying corrections for background, noise, and phase effects, to produce basecalls.

After bases are called, a separate class, PerBaseQual, is called from within Analysis.cpp to calculate the quality predictors for each base and assign a quality from the phred table.

The per base quality, along with all other read information is written to the Standard Flowgram Format (SFF) file using WriteData method from the sff class. The positive integer quality scores per base are listed as the last data line for each read in the SFF file, under the Quality scores heading. The quality scores are on a phred −10*log_10(error rate) scale.

In addition to the SFF file, Ion Torrent also saves the results in FASTQ and Sequence Alignment/Map (SAM) files:

TABLE 11

| | |
|---|---|
| SFF file | The positive integer per base quality scores are under the 'Quality Scores' heading. |
| FASTQ file | The per base quality scores from 0 to 93 are represented by ASCII characters 33-126. |
| SAM file | The per base quality scores are reported in the QUAL field in the form of ASCII characters 33-126. |

Results

The following Analysis Reports are generated and provided by the Ion Torrent Browser: (1) Library Summary; (2) Test Fragment Summary; (3) Ion Sphere™ Particle Summary; (4) Report Information; and (5) File Links.

Files

SFF-formatted or FASTQ-formatted files that contain all library reads for a specific run are generated and can be downloaded from the Ion Torrent Browser, including the following files:

(1) Library Sequence (SFF) files: These files include Standard Flowgram Format (SFF)-formatted files and contain "flow space" data. The data are organized on a per flow basis, and contain information about both nucleotide flows that resulted in base incorporation and those that did not.

(2) Library Sequence (FASTQ) files: These files include FASTQ-formatted file, which is organized in a per base basis, including quality scores. The reads contained in the file are unaligned reads.

(3) Library Alignments (SAM): These are Sequence Alignment/Map (SAM) files containing data that are already aligned.

(4) Test Fragments (SFF): These files include Standard Flowgram Format (SFF) data for Test Fragments only.

Analysis Log File: These files include a detailed log file useful for troubleshooting The following sequencing information is included in the SFF and the FASTQ files:

Read Filtering

Reads that meet the following criteria are reported in the SFF and FASTQ files: The well associated with the read is "positive" for an Ion Sphere.

The well produced a strong signal (greater than 21 counts) across each of the first three key nucleotides. The read contains a minimum of 8 bases.

The key of the read is an exact match following basecalling, which defines a "keypass read."

The read has between 40% and 60% of its flows registering as positive. Reads with greater than 60% positive flows are likely to be mixed reads.

The read fits the expected CAFIE model across the first 60 flows.

Read Trimming

Each reported read is subject to removing lower quality bases according to the following rules: The first four bases of the 5' end that contain the key are removed.

No quality trimming occurs at the 5' end.

At the 3' end, if sequencing occurs through the insert to the B adapter, the B adapter is removed.

The 3' end of the read is trimmed to the point where the average quality score is at least Q9 across a moving 30 bp window.

The FASTQ file only contains filtered and trimmed data. However, the SFF file contains all data but has embedded annotation information that defines the filtered and trimmed regions.

ION Sphere™ Particle Identification Summary

This section of the report is available before the Library Summary or Test Fragment Summary sections are available to provide a quick determination of whether or not the analysis should be permitted to continue. The data generated in this section of the report are created "early" in the analysis process, before base calling, and are intended to be a coarse, initial assessment of run performance. The well data are subject to more stringent analysis in later stages of the analysis.

The report displays the following information:

Wells with Ion Sphere Particles:

Number of wells that were determined to be "positive" for the presence of an ION Sphere particle within the well.

Live Ion Sphere Particles:

Number of wells that contained an ION Sphere particle with a strong signal associated with the library or Test Fragment key. This value is the sum of the following categories: (1) Test Fragment; (2) library Test Fragment Ion Sphere Particles:

Number of Live ION Sphere particles with key signal that was identical to the Test Fragment key signal.

Library Ion Sphere Particles:

Predicted number of Live ION Sphere particles that have a key signal identical to the library key signal.

Template-Positive Ion Sphere Particles:

The estimated percentage of ION Sphere particles that contain sufficient DNA for sequencing. The ratio is approximately live library ION Sphere particles over the total number of particles, less Test Fragment beads and lower quality particles.

Library Key:

Four-base nucleotide sequence that identifies a read as a library read. This sequence is removed from the reported read in the SFF/FASTQ file.

Verified Ion Sphere Library Particles:

Number of ION Sphere particles where the four bases of the library key were confirmed by the base calling algorithm. This is the number of reads reported in the SFF & FASTQ files.

Library Summary

The Library Summary section of the Analysis Report contains performance metrics for reads that contain the library key as the first four bases.

Performance is measured based on either predicted quality, or quality as measured following alignment.

Predicted Quality

The Q20 length value attributed to a read is an estimate of the read length at which the predicted total error rate in the read will correspond to a Phred-scale quality score of 20. The Phred scale is defined as 10×log 10(error probability), so Q20 corresponds to an error rate of 1% and Q17 corresponds to an error rate of 2%.

The Q20 length is determined by looking at the per-base quality scores to estimate the total read error rate at every position in the read. For example, if the first base had a predicted quality score of 20 and the second base had a predicted quality score of 17, then the estimated total read error for the first two bases would be 0.5×1%+0.5×2%=1.5%. This total read error rate is evaluated at every position in the read, after which the maximal position at which the total read error rate is 1% or less is identified. This position defines the Q20 length of the read.

The Q20 length is derived entirely from the predicted per-base quality scores. The predicted quality scores are somewhat conservative and in cases where alignment to a reference sequence is also possible users will generally find that the predicted Q17 lengths tend on average to be shorter than the corresponding AQ17 lengths which are based on the actual as opposed to predicted errors (see the following section on AQ20/AQ17).

Quality Following Alignment

Alignment of reads can be a useful process to assess the quality of both the sequencing reaction and the quality of the underlying library, where a reference is available. Reads are aligned to a reference genome. Any discrepancy in alignment to a reference (whether biological or technical, meaning a real variant or a sequencing error) is listed as an error. Alignment performance metrics are reported depending on how many misaligned bases are permitted. Torrent Suite reports alignment performance at two quality levels: (1) AQ17; and (2) AQ20

The AQ17 length of a read is defined very similarly to the Q17 length (see above), the difference is that instead of using predicted per-base quality scores to estimate error rates we use the actual observed errors based on alignment.

The underlying assumption is that the reference to which the read is aligned represents the true sequence that we should have seen. Suitable caution should be taken when interpreting AQ17 values in situations where the sample sequenced has substantial differences relative to the reference used—for example when working with alignments to a rough draft genome, or with samples that are expected to have high mutation rates relative to the reference used. In such situations the AQ17 lengths might be short even when sequencing quality is excellent.

The AQ20 length is computed as follows: Every base in the read is classified as being correct or incorrect according to the alignment to the reference. At every position in the read, the total error rate is computed up to and including that position. The greatest position at which the error rate is 1% or less is identified, and that position defines the AQ20 length.

For example, if a 100 bp read consists of 80 perfect bases followed by 2 errors and then 18 more perfect bases then the total error rate at position 80 would be 0%, at position 81 it would be 1.2% (1/81), at position 82 it would be 2.4%, and so on up to position 100 where it would be 2% (2/100). The greatest length at which the error rate is 1% or less would be 80 and the greatest length at which the error rate is 2% or less is 100, so the AQ20 and AQ17 lengths are 80 and 100 bases respectively.

Alignment: Nucleic acid sequence information obtained using the Ion Torrent PGM™ system is aligned with known or reference sequences using standard methods. Methods of aligning sequences are well known in the art and there are many alignment algorithms available within the marketplace. Alignment algorithms are also embedded in many of the commercial software tools that are widely available. We also encourage you to experiment with these tools. In some embodiments, alignment within Torrent Browser is performed using TMAP. The precursor to TMAP, BFAST, is based on the ideas in the following publications: Homer N, Merriman B, Nelson S F., "BFAST: An alignment tool for large scale genome resequencing." PMID: 19907642, PLoS ONE. 2009 4(11): e7767, http://dx.doi.org/10.1371/journal.ponc.0007767; Homer N, Merriman B, Nelson S F., "Local alignment of two-base encoded DNA sequence." BMC Bioinformatics. 2009 Jun. 9; 10(1):175. PMID: 19508732, http://dx.doi.org/10.1186/1471-2105-10-175.

Library Summary Report

Performance, measured based on either predicted quality or quality as measured following alignment, is shown in the following sections of the Summary Report: (A) Based on Predicted Per-Base Quality Scores—Independent of Alignment; (B) Reference Genome Information; and (C) Based on Full Library Alignment (A) Based on Predicted Per-Base Quality Scores—Independent of Alignment This section of the Library Report shows performance measured based on predicted quality.

Total number of bases [Mbp]: Number of filtered and trimmed million base pairs reported in the SFF and FASTQ files.

In predicted Q17 read stretches [Mbp]: Number of filtered and trimmed million base pairs contained in read segments that extend from the read start to the 3'-most base at which the total read accuracy is 98% or greater (Q17).

In predicted Q20 read stretches [Mbp]: Number of filtered and trimmed million base pairs contained in read segments that extend from the read start to the 3'-most base at which the total read accuracy is 99% or greater (Q20).

Total number of reads: Total number of filtered and trimmed reads independent of length reported in the SFF and FASTQ files.

At least 50 bp long: Total number of reads at 50 base pairs or longer.

At least 100 bp long: Total number of reads at 100 base pairs or longer.

Mean Length [bp]: Average length, in base pairs, of all filtered and trimmed library reads reported in the SFF and FASTQ files.

Longest Read [bp]: Maximum length, in base pairs, of all filtered and trimmed library reads either reported in the file.

The Read Length Histogram: This is a histogram of the trimmed lengths of all reads present in the SFF file.

The Consensus Key 1-Mer: This graph shows the strength of the signal from the first three one-mer bases of the library key. This graph represents consensus signal measurement of release of $H^+$ ions during nucleotide incorporation. The y-axis shows signal strength, measured in Counts, which is an arbitrary but consistent unit of measure. The x-axis shows time as nucleotide flows over the chip.

There is a known key that exists at the start of every library read. Typically, three bases are shown of the 4-mer key. Note that the graph is displayed in "flow order" rather than "base order." For example, the four base library key is typically TCAG for nucleotides one through four. However, the graph displays that TCAG as TAC which represents the flow order of the nucleotides. Negative flows are not displayed. Although the library key is 4 bases long, only three bases are displayed in the key one-mer graph, because the last base of the library read isn't informative for quality purposes because that flow can contain library information in addition to key information. The next base after the last key base is the first library base. This base varies depending on the library fragment. If the last key base is a G and the first library base is a G, then both of these are incorporated in the same flow resulting in a signal roughly 2× of a one-mer. Thus the one-mer key pass graph only contains n-1 flows for an n-mer library key.

Test Fragment Summary

The Test Fragment Summary section of the Analysis Report provides information about the performance of each Test Fragment included in the experiment (run).

The report displays a summary of the data from the specific Test Fragment, for every Test Fragment found within the specific PGM™ run.

The following Quality metrics are displayed, for each Test Fragment, in tabular form under the heading Test Fragment—<TestFragmentName>, as shown in the following figure:

TF Name: Test Fragment name, as defined in the Templates tab of Torrent Browser

TF Seq: Test Fragment sequence.

Num: Number of filtered & trimmed reads identified for this Test Fragment.

Avg Q17: Average read length with Q17, or better, for this Test Fragment.

50AQ17: Number of reads for this Test Fragment with a minimum of 50 base pairs in length and an error rate of 1 in 50, PHRED-like 17, or better. Quality is based on alignment, not predicted quality.

AQ17 Read Lengths:

The Read Lengths graph is a histogram of read lengths, in bp, that have a Phred-like score of 17 or better (1 error every 50 bp). Distributions that are skewed to the right are ideal, showing longer read lengths (remember, Test Fragments are of a discrete length). Furthermore, it is very likely that the sequence can extend all the way through the Test Fragment provided enough cycles were run. Consequently, the histogram can only display a maximum size based on the length of the Test Fragment used.

Average Corrected Ionogram:

The Average Corrected Ionogram graphs the average corrected Ionogram for this Test Fragment. The x-axis is in flow space and the y-axis shows the signal intensity. A unit of one indicates that there is only a single "base" (i.e., nucleotide) incorporated in a particular flow space, while a unit of two indicates that there are two "bases" (i.e., nucleotides) incorporated of that type in the particular flow space.

The following parameters are also reported, which contain the following information about a particular sequencing run:

TABLE 12

| | |
|---|---|
| Lib Key Signal | Strength of the signal associated with the library key. |
| Q17 Bases | Number of base pairs of sequence in predicted Q17 stretches. |
| 100 bp AQ17 | Number of reads 100 bp or longer at Q17 or better based on |
| AQ17 Bases | Number of base pairs of sequence from reads with Q17 or better |

Expanded Reports for Individual Test Fragments:

TABLE 13

The following parameters relating to the performance of individual Test Fragments can also be downloaded from the Ion Torrent Browser:

| | |
|---|---|
| TF Name | Test Fragment label. |
| TF Reads | Number of reads that are associated with this Test Fragment. |
| TF Key | Measure of strength of the voltage signal associated with this |
| TF AQ17 | Average length of this Test Fragment, in base pairs. |

Figure 4:
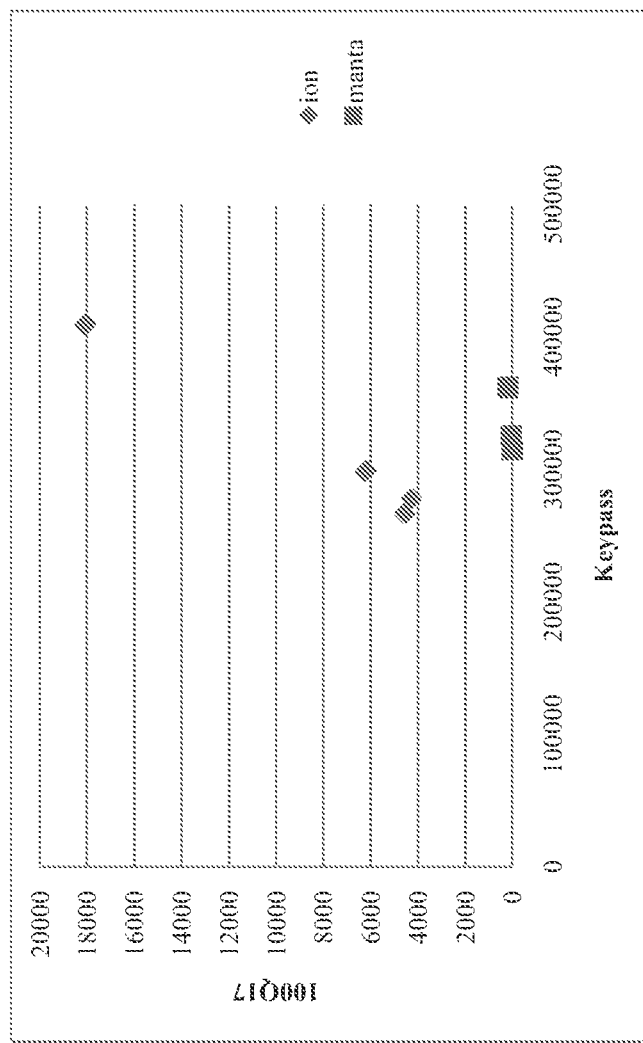
FIG. 4 shows the 100Q17 vs. Keypass for a sequencing reaction using the unmodified Bst DNA polymerase having the amino acid sequence of SEQ ID NO: 1 ("manta") and the modified Bst DNA polymerase having the amino acid sequence of SEQ ID NO: 2 ("ion").
Figure 5:
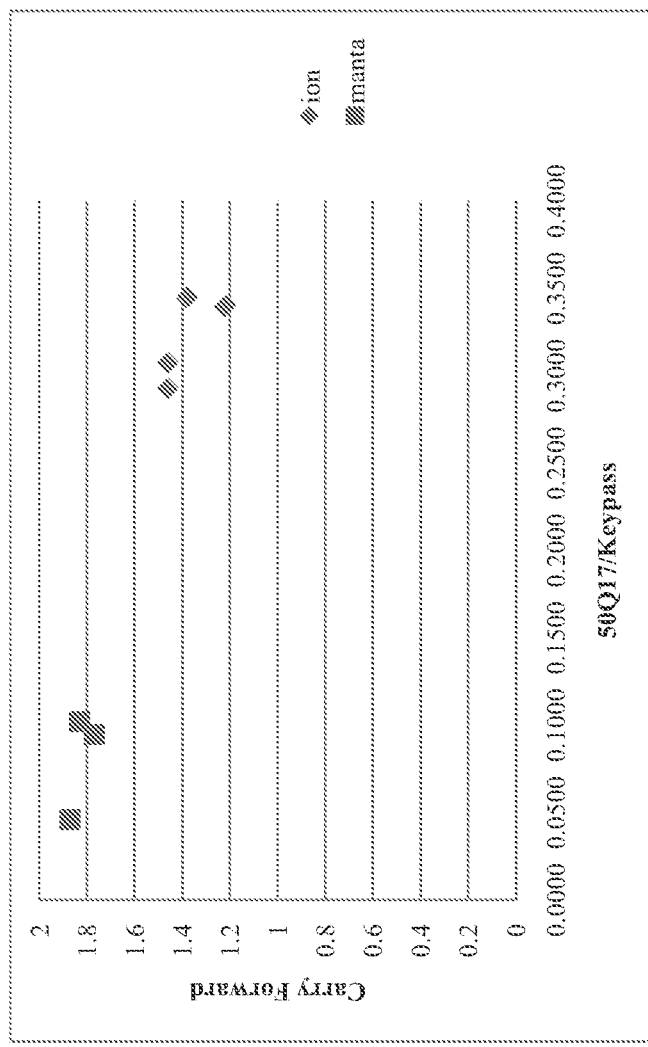
FIG. 5 shows the Carryforward vs. 50Q17/Keypass for a sequencing reaction using the unmodified Bst DNA polymerase having the amino acid sequence of SEQ ID NO: 1 ("manta") and the modified Bst DNA polymerase having the amino acid sequence of SEQ ID NO: 2 ("ion").

Representative results of data obtained from sequencing reactions in the Ion Torrent PGM™ sequencing, performed essentially as described above and comparing results obtaining the unmodified (reference) Bst polymerase of SEQ ID NO: 1 and the modified Bst polymerase of SEQ ID NO: 2 are shown in FIGS. 3, 4, and 5. FIG. 3 shows the 50Q17 vs. Keypass for a sequencing reaction using the unmodified Bst DNA polymerase having the amino acid sequence of SEQ ID NO: 1 ("manta") and the modified Bst DNA polymerase having the amino acid sequence of SEQ ID NO: 2 ("ion").

FIG. 4 shows the 100Q17 vs. Keypass for a sequencing reaction using the unmodified Bst DNA polymerase having the amino acid sequence of SEQ ID NO: 1 ("manta") and the modified Bst DNA polymerase having the amino acid sequence of SEQ ID NO: 2 ("ion").

FIG. 5 shows the Carryforward vs. 50Q17/Keypass for a sequencing reaction using a reference Bst DNA polymerase having the amino acid sequence of SEQ ID NO: 1 ("manta") and a modified Bst DNA polymerase having the amino acid sequence of SEQ ID NO: 2 ("ion").

The raw data obtained for the sequencing run is depicted in FIG. 6. "IE" refers to the numbers of Incomplete Extensions observed in each reaction; "CF" refers to the number of carryforwards observed in each reaction.

TABLE 2

Candidate amino acid residues for modification in Bst DNA polymerase (including pKa values for amino acid residues calculated using PropKa)

| Amino Acid Residue | pKa | | |
|---|---|---|---|
| GLU-277 | 4.64 | | |
| GLU-372 | 4.7 | | |
| GLU-15 | 4.71 | | |
| GLU-206 | 4.71 | | |
| GLU-426 | 4.71 | | |
| GLU-493 | 4.71 | | |
| GLU-456 | 4.76 | | |
| GLU-131 | 4.78 | | |
| GLU-349 | 4.78 | | |
| GLU-446 | 4.85 | | |
| GLU-522 | 4.85 | | |
| GLU-558 | 4.85 | | |
| GLU-26 | 4.92 | | |
| GLU-294 | 4.92 | | |
| GLU-363 | 5.08 | | |
| HIS-534 | 5.12 | | |
| HIS-572 | 6.17 | S | |
| HIS-473 | 6.29 | B | |

TABLE 2-continued

Candidate amino acid residues for modification in Bst DNA polymerase (including pKa values for amino acid residues calculated using PropKa)

| Amino Acid Residue | pKa | | |
|---|---|---|---|
| HIS-46 | 6.43 | S | |
| HIS-273 | 6.51 | S | |
| LYS-510 | 7.29 | B | |
| N+ | 7.86 | S | |
| TYR-477 | 7.98 | B | |
| LYS-73 | 8.55 | | |
| CYS-550 | 8.87 | | |
| CYS-93 | 9.57 | | |

TABLE 3

Candidate amino acid residues for modification in Bst DNA polymerase (including pKa values for amino acid residues calculated using H++)

| Amino Acid Residue | pKa | |
|---|---|---|
| GLU-461 | 4.533 | |
| GLU-206 | 4.555 | |
| ASP-113 | 4.57 | |
| HIS-273 | 4.662 | |
| HIS-534 | 4.747 | |
| GLU-277 | 4.806 | |
| GLU-456 | 4.902 | |
| GLU-544 | 4.972 | |
| GLU-54 | 5.037 | |
| GLU-30 | 5.149 | |
| GLU-349 | 5.158 | |
| GLU-522 | 5.221 | |
| HIS-151 | 5.26 | |
| GLU-558 | 5.361 | |
| GLU-220 | 5.423 | |
| GLU-446 | 5.911 | S |
| NTA | 6.465 | S |
| HIS-46 | 7.653 | S |
| HIS-572 | 8.056 | S |
| HIS-308 | 8.333 | |
| HIS-473 | 8.397 | |
| LYS-411 | 9.494 | |
| LYS-543 | 9.72 | |
| LYS-287 | 9.815 | |
| TYR-419 | 10.041 | |
| LYS-253 | 10.077 | |

TABLE 4

Candidate amino acids for modification in E. coli SSB

| Amino Acid Residue | pKa |
|---|---|
| HIS-55 | 3.968 |
| ASP-90 | 4.251 |
| ASP-17 | 4.298 |
| ASP-42 | 4.449 |
| GLU-50 | 4.738 |
| GLU-65 | 4.856 |
| GLU-47 | 4.878 |
| GLU-19 | 4.896 |
| GLU-53 | 5.046 |
| ASP-95 | 5.143 |
| GLU-69 | 5.214 |
| GLU-38 | 5.606 |
| NTALA-1 | 5.851 |
| GLU-80 | 5.898 |
| LYS-7 | 7.276 |
| LYS-49 | 8.791 |
| GLU-100 | 9.033 |
| ARG-3 | 9.069 |
| LYS-87 | 9.453 |

TABLE 4-continued

Candidate amino acids for modification in E. coli SSB

| Amino Acid Residue | pKa |
|---|---|
| LYS-62 | 9.754 |
| LYS-43 | 10.399 |
| TYR-22 | 10.427 |
| TYR-97 | 10.483 |
| TYR-70 | 10.619 |
| LYS-73 | 10.898 |
| ARG-56 | 11.169 |
| ARG-96 | 11.176 |
| ARG-86 | 11.257 |
| ARG-84 | 11.296 |
| ARG-41 | 11.381 |
| ARG-115 | 11.804 |
| ARG-21 | 12.035 |
| ARG-72 | 12.671 |
| TYR-78 | 16.412 |

TABLE 5

Candidate amino acids for substitution in Therminator ™ DNA polymerase

| Amino Acid Residue | pKa (calc) | pKa (model) |
|---|---|---|
| ASP 4 | 7.85 | |
| ASP 6 | 5.95 | |
| ASP 31 | 2.11 | |
| ASP 44 | 2.53 | |
| ASP 45 | 3.60 | |
| ASP 50 | 2.82 | |
| ASP 92 | 4.14 | |
| ASP 98 | 3.43 | |
| ASP 108 | 4.05 | 3.80 |
| ASP 113 | 3.10 | 3.80 |
| ASP 123 | 4.09 | 3.80 |
| ASP 132 | 3.64 | 3.80 |
| ASP 164 | 1.56 | 3.80 |
| ASP 177 | 3.87 | 3.80 |
| ASP 182 | 3.79 | 3.80 |
| ASP 202 | 3.47 | 3.80 |
| ASP 204 | 2.82 | 3.80 |
| ASP 212 | 2.14 | 3.80 |
| ASP 215 | 7.23 | 3.80 |
| ASP 235 | 2.59 | 3.80 |
| ASP 246 | 3.29 | 3.80 |
| ASP 259 | 6.50 | 3.80 |
| ASP 315 | 5.97 | 3.80 |
| ASP 343 | 3.69 | 3.80 |
| ASP 373 | 3.18 | 3.80 |
| ASP 398 | 4.52 | 3.80 |
| ASP 404 | 6.10 | 3.80 |
| ASP 421 | 4.42 | 3.80 |
| ASP 432 | 2.60 | 3.80 |
| ASP 444 | 3.20 | 3.80 |
| ASP 455 | 3.97 | 3.80 |
| ASP 472 | 3.03 | 3.80 |
| ASP 480 | 3.21 | 3.80 |
| ASP 540 | 3.92 | 3.80 |
| ASP 542 | 4.89 | 3.80 |
| ASP 552 | 2.69 | 3.80 |
| ASP 598 | 3.40 | 3.80 |
| ASP 614 | 3.89 | 3.80 |
| ASP 635 | 2.78 | 3.80 |
| ASP 712 | 3.83 | 3.80 |
| ASP 718 | 3.80 | 3.80 |
| GLU 10 | 4.05 | 4.50 |
| GLU 22 | 4.12 | 4.50 |
| GLU 25 | 3.60 | 4.50 |
| GLU 29 | 4.26 | 4.50 |
| GLU 35 | 2.57 | 4.50 |
| GLU 49 | 3.85 | 4.50 |
| GLU 69 | 4.56 | 4.50 |
| GLU 81 | 4.38 | 4.50 |
| GLU 111 | 4.60 | 4.50 |
| GLU 130 | 4.51 | 4.50 |
| GLU 133 | 3.91 | 4.50 |
| GLU 134 | 4.91 | 4.50 |
| GLU 148 | 5.27 | 4.50 |
| GLU 150 | 5.08 | 4.50 |
| GLU 151 | 4.10 | 4.50 |
| GLU 167 | 4.42 | 4.50 |
| GLU 187 | 4.70 | 4.50 |
| GLU 189 | 3.57 | 4.50 |
| GLU 200 | 4.18 | 4.50 |
| GLU 224 | 4.29 | 4.50 |
| GLU 225 | 4.55 | 4.50 |
| GLU 238 | 4.49 | 4.50 |
| GLU 251 | 4.60 | 4.50 |
| GLU 276 | 4.43 | 4.50 |
| GLU 280 | 4.75 | 4.50 |
| GLU 288 | 3.94 | 4.50 |
| GLU 293 | 4.71 | 4.50 |
| GLU 294 | 3.67 | 4.50 |
| GLU 300 | 4.26 | 4.50 |
| GLU 303 | 4.59 | 4.50 |
| GLU 306 | 4.72 | 4.50 |
| GLU 314 | 5.00 | 4.50 |
| GLU 321 | 4.64 | 4.50 |
| GLU 325 | 4.87 | 4.50 |
| GLU 330 | 7.31 | 4.50 |
| GLU 354 | 5.67 | 4.50 |
| GLU 366 | 6.07 | 4.50 |
| GLU 374 | 4.64 | 4.50 |
| GLU 376 | 3.89 | 4.50 |
| GLU 391 | 4.65 | 4.50 |
| GLU 393 | 3.42 | 4.50 |
| GLU 426 | 4.46 | 4.50 |
| GLU 430 | 4.75 | 4.50 |
| GLU 436 | 4.54 | 4.50 |
| GLU 458 | 4.49 | 4.50 |
| GLU 459 | 3.84 | 4.50 |
| GLU 475 | 4.11 | 4.50 |
| GLU 508 | 4.65 | 4.50 |
| GLU 511 | 3.78 | 4.50 |
| GLU 519 | 4.91 | 4.50 |
| GLU 522 | 4.09 | 4.50 |
| GLU 527 | 2.97 | 4.50 |
| GLU 529 | 4.67 | 4.50 |
| GLU 530 | 4.53 | 4.50 |
| GLU 554 | 4.84 | 4.50 |
| GLU 562 | 4.46 | 4.50 |
| GLU 576 | 5.03 | 4.50 |
| GLU 578 | 3.64 | 4.50 |
| GLU 580 | 4.99 | 4.50 |
| GLU 599 | 5.35 | 4.50 |
| GLU 600 | 6.04 | 4.50 |
| GLU 609 | 5.62 | 4.50 |
| GLU 617 | 4.45 | 4.50 |
| GLU 621 | 4.96 | 4.50 |
| GLU 628 | 4.02 | 4.50 |
| GLU 637 | 5.22 | 4.50 |
| GLU 638 | 4.75 | 4.50 |
| GLU 645 | 4.50 | 4.50 |
| GLU 664 | 4.36 | 4.50 |
| GLU 719 | 4.28 | 4.50 |
| GLU 730 | 4.72 | 4.50 |
| GLU 734 | 4.98 | 4.50 |
| GLU 742 | 3.65 | 4.50 |
| C-750 | 3.25 | 3.20 |
| HIS 59 | 6.13 | 6.50 |
| HIS 89 | 4.69 | 6.50 |
| HIS 103 | 7.00 | 6.50 |
| HIS 147 | 7.17 | 6.50 |
| HIS 257 | 4.01 | 6.50 |
| HIS 416 | 5.54 | 6.50 |
| HIS 439 | 6.77 | 6.50 |
| HIS 545 | 2.90 | 6.50 |

TABLE 5-continued

Candidate amino acids for substitution in Therminator ™ DNA polymerase

| Amino Acid Residue | pKa (calc) | pKa (model) |
|---|---|---|
| HIS 633 | 6.96 | 6.50 |
| HIS 663 | 5.84 | 6.50 |
| HIS 679 | 6.64 | 6.50 |
| CYS 223 | 11.84 | 9.00 |
| CYS 428 | 99.99 | 99.99 |
| CYS 442 | 99.99 | 99.99 |
| CYS 506 | 99.99 | 99.99 |
| CYS 509 | 99.99 | 99.99 |
| TYR 7 | 10.59 | 10.00 |
| TYR 30 | 10.26 | 10.00 |
| TYR 37 | 17.23 | 10.00 |
| TYR 39 | 14.20 | 10.00 |
| TYR 86 | 10.20 | 10.00 |
| TYR 110 | 11.95 | 10.00 |
| TYR 112 | 10.49 | 10.00 |
| TYR 120 | 13.12 | 10.00 |
| TYR 146 | 11.21 | 10.00 |
| TYR 162 | 11.82 | 10.00 |
| TYR 180 | 11.47 | 10.00 |
| TYR 209 | 13.47 | 10.00 |
| TYR 218 | 11.91 | 10.00 |
| TYR 261 | 10.23 | 10.00 |
| TYR 273 | 9.77 | 10.00 |
| TYR 279 | 11.96 | 10.00 |
| TYR 291 | 10.52 | 10.00 |
| TYR 311 | 14.21 | 10.00 |
| TYR 320 | 10.89 | 10.00 |
| TYR 362 | 11.49 | 10.00 |
| TYR 384 | 11.17 | 10.00 |
| TYR 388 | 12.23 | 10.00 |
| TYR 402 | 14.32 | 10.00 |
| TYR 409 | 14.74 | 10.00 |
| TYR 431 | 10.05 | 10.00 |
| TYR 481 | 10.52 | 10.00 |
| TYR 494 | 12.59 | 10.00 |
| TYR 496 | 16.00 | 10.00 |
| TYR 497 | 14.40 | 10.00 |
| TYR 499 | 11.49 | 10.00 |
| TYR 505 | 11.27 | 10.00 |
| TYR 520 | 11.38 | 10.00 |
| TYR 538 | 13.52 | 10.00 |
| TYR 566 | 11.47 | 10.00 |
| TYR 579 | 11.62 | 10.00 |
| TYR 583 | 11.55 | 10.00 |
| TYR 594 | 12.23 | 10.00 |
| TYR 701 | 14.24 | 10.00 |
| TYR 731 | 10.99 | 10.00 |
| TYR 732 | 11.88 | 10.00 |
| TYR 750 | 10.81 | 10.00 |
| LYS 13 | 10.18 | 10.50 |
| LYS 20 | 11.10 | 10.50 |
| LYS 21 | 10.56 | 10.50 |
| LYS 27 | 11.24 | 10.50 |
| LYS 43 | 10.25 | 10.50 |
| LYS 52 | 11.08 | 10.50 |
| LYS 53 | 10.63 | 10.50 |
| LYS 57 | 10.28 | 10.50 |
| LYS 64 | 10.26 | 10.50 |
| LYS 66 | 10.51 | 10.50 |
| LYS 70 | 11.41 | 10.50 |
| LYS 73 | 9.02 | 10.50 |
| LYS 74 | 10.47 | 10.50 |
| LYS 84 | 10.64 | 10.50 |
| LYS 118 | 10.50 | 10.50 |
| LYS 124 | 10.20 | 10.50 |
| LYS 174 | 10.01 | 10.50 |
| LYS 175 | 10.42 | 10.50 |
| LYS 188 | 10.15 | 10.50 |
| LYS 192 | 11.36 | 10.50 |
| LYS 201 | 12.01 | 10.50 |
| LYS 220 | 10.65 | 10.50 |
| LYS 221 | 10.80 | 10.50 |
| LYS 229 | 10.54 | 10.50 |
| LYS 240 | 10.09 | 10.50 |
| LYS 253 | 11.39 | 10.50 |
| LYS 285 | 10.22 | 10.50 |
| LYS 287 | 11.74 | 10.50 |
| LYS 289 | 9.16 | 10.50 |
| LYS 317 | 10.31 | 10.50 |
| LYS 360 | 8.91 | 10.50 |
| LYS 363 | 10.27 | 10.50 |
| LYS 371 | 9.91 | 10.50 |
| LYS 390 | 10.38 | 10.50 |
| LYS 429 | 10.64 | 10.50 |
| LYS 440 | 10.41 | 10.50 |
| LYS 443 | 10.92 | 10.50 |
| LYS 462 | 11.52 | 10.50 |
| LYS 464 | 8.83 | 10.50 |
| LYS 466 | 10.69 | 10.50 |
| LYS 468 | 10.07 | 10.50 |
| LYS 476 | 10.26 | 10.50 |
| LYS 477 | 10.91 | 10.50 |
| LYS 487 | 10.75 | 10.50 |
| LYS 501 | 10.22 | 10.50 |
| LYS 507 | 10.64 | 10.50 |
| LYS 531 | 11.77 | 10.50 |
| LYS 535 | 10.87 | 10.50 |
| LYS 557 | 10.51 | 10.50 |
| LYS 558 | 10.76 | 10.50 |
| LYS 559 | 10.31 | 10.50 |
| LYS 561 | 10.04 | 10.50 |
| LYS 565 | 10.25 | 10.50 |
| LYS 591 | 10.45 | 10.50 |
| LYS 592 | 10.20 | 10.50 |
| LYS 593 | 9.74 | 10.50 |
| LYS 602 | 10.54 | 10.50 |
| LYS 620 | 10.49 | 10.50 |
| LYS 632 | 10.36 | 10.50 |
| LYS 644 | 10.24 | 10.50 |
| LYS 684 | 10.40 | 10.50 |
| LYS 692 | 10.25 | 10.50 |
| LYS 705 | 9.57 | 10.50 |
| LYS 746 | 11.49 | 10.50 |
| ARG 17 | 12.25 | 12.50 |
| ARG 32 | 13.03 | 12.50 |
| ARG 58 | 12.29 | 12.50 |
| ARG 67 | 14.10 | 12.50 |
| ARG 78 | 12.36 | 12.50 |
| ARG 97 | 11.98 | 12.50 |
| ARG 99 | 12.16 | 12.50 |
| ARG 101 | 14.07 | 12.50 |
| ARG 119 | 16.80 | 12.50 |
| ARG 169 | 13.55 | 12.50 |
| ARG 193 | 12.78 | 12.50 |
| ARG 196 | 12.44 | 12.50 |
| ARG 199 | 12.34 | 12.50 |
| ARG 222 | 13.63 | 12.50 |
| ARG 234 | 12.80 | 12.50 |
| ARG 243 | 12.36 | 12.50 |
| ARG 247 | 12.27 | 12.50 |
| ARG 255 | 10.00 | 12.50 |
| ARG 265 | 13.14 | 12.50 |
| ARG 266 | 11.19 | 12.50 |
| ARG 307 | 12.83 | 12.50 |
| ARG 310 | 13.21 | 12.50 |
| ARG 324 | 12.66 | 12.50 |
| ARG 335 | 12.16 | 12.50 |
| ARG 346 | 13.10 | 12.50 |
| ARG 359 | 10.29 | 12.50 |
| ARG 364 | 11.85 | 12.50 |
| ARG 375 | 12.65 | 12.50 |
| ARG 379 | 12.22 | 12.50 |
| ARG 380 | 12.33 | 12.50 |
| ARG 381 | 12.44 | 12.50 |
| ARG 394 | 12.45 | 12.50 |
| ARG 406 | 12.99 | 12.50 |
| ARG 425 | 11.45 | 12.50 |
| ARG 460 | 11.44 | 12.50 |

TABLE 5-continued

Candidate amino acids for substitution in Therminator ™ DNA polymerase

| Amino Acid Residue | pKa (calc) | pKa (model) |
|---|---|---|
| ARG 465 | 12.42 | 12.50 |
| ARG 482 | 10.68 | 12.50 |
| ARG 484 | 12.31 | 12.50 |
| ARG 503 | 13.11 | 12.50 |
| ARG 518 | 13.62 | 12.50 |
| ARG 526 | 12.48 | 12.50 |
| ARG 585 | 12.11 | 12.50 |
| ARG 606 | 13.59 | 12.50 |
| ARG 612 | 12.73 | 12.50 |
| ARG 613 | 12.46 | 12.50 |
| ARG 625 | 12.48 | 12.50 |
| ARG 641 | 12.85 | 12.50 |
| ARG 685 | 13.07 | 12.50 |
| ARG 689 | 13.04 | 12.50 |
| ARG 694 | 12.46 | 12.50 |
| ARG 713 | 12.20 | 12.50 |
| ARG 743 | 12.30 | 12.50 |
| N + 1 | 7.38 | 8.00 |

TABLE 6

Candidate amino acids for substitution in KOD DNA polymerase

| Amino Acid Residue | pKa (calc) | pKa (model) |
|---|---|---|
| ASP 4 | 7.06 | 3.80 |
| ASP 6 | −1.72 | 3.80 |
| ASP 11 | 3.94 | 3.80 |
| ASP 31 | 1.79 | 3.80 |
| ASP 44 | 3.94 | 3.80 |
| ASP 45 | 2.58 | 3.80 |
| ASP 92 | 2.18 | 3.80 |
| ASP 98 | 3.41 | 3.80 |
| ASP 108 | 3.11 | 3.80 |
| ASP 113 | −0.42 | 3.80 |
| ASP 123 | 1.89 | 3.80 |
| ASP 132 | 3.23 | 3.80 |
| ASP 141 | 15.80 | 3.80 |
| ASP 164 | 3.36 | 3.80 |
| ASP 177 | 3.87 | 3.80 |
| ASP 182 | 3.31 | 3.80 |
| ASP 202 | −1.29 | 3.80 |
| ASP 204 | 1.17 | 3.80 |
| ASP 212 | −3.07 | 3.80 |
| ASP 215 | 4.76 | 3.80 |
| ASP 235 | −0.47 | 3.80 |
| ASP 246 | 4.01 | 3.80 |
| ASP 259 | 4.82 | 3.80 |
| ASP 315 | 3.17 | 3.80 |
| ASP 343 | 3.50 | 3.80 |
| ASP 373 | 2.82 | 3.80 |
| ASP 404 | 3.03 | 3.80 |
| ASP 421 | 3.55 | 3.80 |
| ASP 432 | 3.68 | 3.80 |
| ASP 444 | 3.15 | 3.80 |
| ASP 455 | 3.74 | 3.80 |
| ASP 472 | 2.98 | 3.80 |
| ASP 480 | 3.62 | 3.80 |
| ASP 540 | 3.09 | 3.80 |
| ASP 542 | 8.78 | 3.80 |
| ASP 552 | 3.53 | 3.80 |
| ASP 598 | 3.43 | 3.80 |
| ASP 614 | −1.00 | 3.80 |
| ASP 633 | 3.59 | 3.80 |
| ASP 635 | 3.18 | 3.80 |
| ASP 718 | −2.60 | 3.80 |
| ASP 721 | −4.20 | 3.80 |
| ASP 728 | −5.80 | 3.80 |
| ASP 754 | −7.40 | 3.80 |
| GLU 10 | 4.03 | 4.50 |

TABLE 6-continued

Candidate amino acids for substitution in KOD DNA polymerase

| Amino Acid Residue | pKa (calc) | pKa (model) |
|---|---|---|
| GLU 22 | 3.47 | 4.50 |
| GLU 25 | 4.06 | 4.50 |
| GLU 29 | 3.91 | 4.50 |
| GLU 35 | 3.43 | 4.50 |
| GLU 49 | 3.79 | 4.50 |
| GLU 50 | 4.50 | 4.50 |
| GLU 57 | 4.71 | 4.50 |
| GLU 69 | 3.54 | 4.50 |
| GLU 81 | 3.98 | 4.50 |
| GLU 102 | 4.78 | 4.50 |
| GLU 111 | 2.22 | 4.50 |
| GLU 130 | 4.78 | 4.50 |
| GLU 133 | 4.36 | 4.50 |
| GLU 134 | 4.50 | 4.50 |
| GLU 143 | 9.42 | 4.50 |
| GLU 148 | 4.64 | 4.50 |
| GLU 150 | 5.76 | 4.50 |
| GLU 151 | 15.70 | 4.50 |
| GLU 154 | 4.10 | 4.50 |
| GLU 165 | 3.26 | 4.50 |
| GLU 166 | 4.35 | 4.50 |
| GLU 187 | 0.05 | 4.50 |
| GLU 189 | 4.21 | 4.50 |
| GLU 200 | 4.43 | 4.50 |
| GLU 224 | 4.64 | 4.50 |
| GLU 238 | 3.49 | 4.50 |
| GLU 251 | 4.31 | 4.50 |
| GLU 276 | 0.56 | 4.50 |
| GLU 280 | 4.78 | 4.50 |
| GLU 288 | 4.61 | 4.50 |
| GLU 293 | 4.50 | 4.50 |
| GLU 294 | 3.98 | 4.50 |
| GLU 300 | 4.85 | 4.50 |
| GLU 303 | 4.57 | 4.50 |
| GLU 306 | 4.69 | 4.50 |
| GLU 314 | 3.66 | 4.50 |
| GLU 321 | 3.37 | 4.50 |
| GLU 325 | 4.50 | 4.50 |
| GLU 330 | 6.95 | 4.50 |
| GLU 354 | 3.49 | 4.50 |
| GLU 363 | 1.46 | 4.50 |
| GLU 366 | 4.66 | 4.50 |
| GLU 374 | 4.36 | 4.50 |
| GLU 376 | 3.83 | 4.50 |
| GLU 385 | 4.50 | 4.50 |
| GLU 391 | 4.64 | 4.50 |
| GLU 393 | 3.84 | 4.50 |
| GLU 398 | 3.91 | 4.50 |
| GLU 426 | 2.90 | 4.50 |
| GLU 430 | 4.57 | 4.50 |
| GLU 458 | 4.50 | 4.50 |
| GLU 459 | 4.53 | 4.50 |
| GLU 475 | 4.54 | 4.50 |
| GLU 508 | 3.90 | 4.50 |
| GLU 511 | 4.19 | 4.50 |
| GLU 519 | 4.57 | 4.50 |
| GLU 527 | 4.04 | 4.50 |
| GLU 529 | 3.93 | 4.50 |
| GLU 530 | 4.05 | 4.50 |
| GLU 554 | 4.60 | 4.50 |
| GLU 562 | 4.64 | 4.50 |
| GLU 576 | 4.47 | 4.50 |
| GLU 578 | 5.53 | 4.50 |
| GLU 580 | 4.12 | 4.50 |
| GLU 599 | 4.05 | 4.50 |
| GLU 600 | 4.64 | 4.50 |
| GLU 609 | 14.10 | 4.50 |
| GLU 617 | 12.50 | 4.50 |
| GLU 621 | 10.90 | 4.50 |
| GLU 628 | 4.47 | 4.50 |
| GLU 637 | 4.50 | 4.50 |
| GLU 645 | 4.50 | 4.50 |
| GLU 648 | 4.50 | 4.50 |
| GLU 654 | 4.50 | 4.50 |
| GLU 658 | 3.94 | 4.50 |

TABLE 6-continued

Candidate amino acids for substitution in KOD DNA polymerase

| Amino Acid Residue | pKa (calc) | pKa (model) |
|---|---|---|
| GLU 664 | 9.30 | 4.50 |
| GLU 719 | 7.70 | 4.50 |
| GLU 730 | 6.10 | 4.50 |
| GLU 734 | 4.50 | 4.50 |
| GLU 742 | 2.90 | 4.50 |
| GLU 753 | 1.30 | 4.50 |
| HIS 59 | 6.43 | 6.50 |
| HIS 89 | 4.54 | 6.50 |
| HIS 103 | 6.15 | 6.50 |
| HIS 147 | 6.36 | 6.50 |
| HIS 257 | 4.00 | 6.50 |
| HIS 416 | 2.74 | 6.50 |
| HIS 439 | 7.09 | 6.50 |
| HIS 663 | 6.50 | 6.50 |
| HIS 679 | 6.50 | 6.50 |
| HIS 725 | 6.50 | 6.50 |
| CYS 223 | 10.07 | 9.00 |
| CYS 428 | 99.99 | 9.00 |
| CYS 442 | 99.99 | 9.00 |
| CYS 506 | 6.50 | 9.00 |
| CYS 509 | 16.78 | 9.00 |
| TYR 7 | 10.67 | 10.00 |
| TYR 30 | 10.00 | 10.00 |
| TYR 37 | 17.98 | 10.00 |
| TYR 39 | 12.92 | 10.00 |
| TYR 86 | 13.65 | 10.00 |
| TYR 110 | 12.67 | 10.00 |
| TYR 112 | 10.84 | 10.00 |
| TYR 120 | 13.53 | 10.00 |
| TYR 146 | 10.06 | 10.00 |
| TYR 162 | 10.41 | 10.00 |
| TYR 180 | 10.00 | 10.00 |
| TYR 209 | 11.28 | 10.00 |
| TYR 218 | 7.75 | 10.00 |
| TYR 261 | 9.34 | 10.00 |
| TYR 273 | 9.22 | 10.00 |
| TYR 279 | 13.15 | 10.00 |
| TYR 291 | 10.00 | 10.00 |
| TYR 311 | 16.84 | 10.00 |
| TYR 320 | 14.28 | 10.00 |
| TYR 362 | 12.68 | 10.00 |
| TYR 384 | 10.00 | 10.00 |
| TYR 388 | 10.00 | 10.00 |
| TYR 402 | 17.93 | 10.00 |
| TYR 409 | 12.25 | 10.00 |
| TYR 431 | 9.81 | 10.00 |
| TYR 481 | 11.76 | 10.00 |
| TYR 493 | 12.60 | 10.00 |
| TYR 494 | 9.46 | 10.00 |
| TYR 496 | 14.11 | 10.00 |
| TYR 497 | 15.66 | 10.00 |
| TYR 499 | 9.84 | 10.00 |
| TYR 505 | 8.20 | 10.00 |
| TYR 520 | 11.19 | 10.00 |
| TYR 532 | 11.04 | 10.00 |
| TYR 538 | 12.70 | 10.00 |
| TYR 566 | 13.34 | 10.00 |
| TYR 579 | 10.65 | 10.00 |
| TYR 583 | 13.57 | 10.00 |
| TYR 594 | 10.60 | 10.00 |
| TYR 653 | 9.87 | 10.00 |
| TYR 701 | 10.00 | 10.00 |
| TYR 750 | 10.24 | 10.00 |
| N+ | 17.37 | 8.00 |
| LYS 13 | 10.15 | 10.50 |
| LYS 20 | 10.22 | 10.50 |
| LYS 21 | 9.87 | 10.50 |
| LYS 27 | 10.36 | 10.50 |
| LYS 43 | 10.43 | 10.50 |
| LYS 52 | 10.08 | 10.50 |
| LYS 53 | 10.08 | 10.50 |
| LYS 66 | 10.01 | 10.50 |
| LYS 70 | 9.94 | 10.50 |
| LYS 73 | 10.06 | 10.50 |
| LYS 74 | 10.50 | 10.50 |
| LYS 84 | 9.60 | 10.50 |
| LYS 99 | 10.50 | 10.50 |
| LYS 118 | 11.22 | 10.50 |
| LYS 124 | 9.94 | 10.50 |
| LYS 174 | 10.43 | 10.50 |
| LYS 192 | 10.36 | 10.50 |
| LYS 199 | 8.13 | 10.50 |
| LYS 201 | 9.94 | 10.50 |
| LYS 220 | 10.29 | 10.50 |
| LYS 221 | 10.22 | 10.50 |
| LYS 225 | 10.50 | 10.50 |
| LYS 240 | 10.01 | 10.50 |
| LYS 253 | 12.95 | 10.50 |
| LYS 287 | 14.68 | 10.50 |
| LYS 289 | 11.48 | 10.50 |
| LYS 317 | 10.23 | 10.50 |
| LYS 324 | 10.08 | 10.50 |
| LYS 360 | 11.55 | 10.50 |
| LYS 371 | 9.51 | 10.50 |
| LYS 375 | 10.50 | 10.50 |
| LYS 429 | 10.50 | 10.50 |
| LYS 443 | 10.22 | 10.50 |
| LYS 462 | 10.50 | 10.50 |
| LYS 466 | 10.22 | 10.50 |
| LYS 468 | 10.29 | 10.50 |
| LYS 477 | 10.50 | 10.50 |
| LYS 487 | 10.24 | 10.50 |
| LYS 507 | 11.91 | 10.50 |
| LYS 526 | 10.22 | 10.50 |
| LYS 531 | 10.15 | 10.50 |
| LYS 535 | 10.36 | 10.50 |
| LYS 557 | 10.01 | 10.50 |
| LYS 565 | 10.50 | 10.50 |
| LYS 570 | 10.36 | 10.50 |
| LYS 592 | 10.50 | 10.50 |
| LYS 602 | 10.43 | 10.50 |
| LYS 632 | 10.36 | 10.50 |
| LYS 638 | 10.15 | 10.50 |
| LYS 726 | 9.87 | 10.50 |
| ARG 17 | 15.49 | 12.50 |
| ARG 32 | 12.15 | 12.50 |
| ARG 58 | 11.45 | 12.50 |
| ARG 67 | 11.73 | 12.50 |
| ARG 78 | 11.94 | 12.50 |
| ARG 97 | 12.43 | 12.50 |
| ARG 101 | 12.08 | 12.50 |
| ARG 119 | 17.00 | 12.50 |
| ARG 169 | 12.15 | 12.50 |
| ARG 188 | 11.94 | 12.50 |
| ARG 193 | 13.69 | 12.50 |
| ARG 196 | 12.29 | 12.50 |
| ARG 222 | 14.49 | 12.50 |
| ARG 234 | 14.17 | 12.50 |
| ARG 243 | 12.50 | 12.50 |
| ARG 247 | 12.01 | 12.50 |
| ARG 255 | 9.85 | 12.50 |
| ARG 265 | 12.01 | 12.50 |
| ARG 266 | 10.80 | 12.50 |
| ARG 307 | 12.15 | 12.50 |
| ARG 310 | 12.22 | 12.50 |
| ARG 335 | 8.74 | 12.50 |
| ARG 346 | 11.16 | 12.50 |
| ARG 359 | 9.85 | 12.50 |
| ARG 364 | 11.90 | 12.50 |
| ARG 379 | 12.08 | 12.50 |
| ARG 380 | 11.96 | 12.50 |
| ARG 381 | 12.15 | 12.50 |
| ARG 394 | 12.50 | 12.50 |
| ARG 406 | 12.39 | 12.50 |
| ARG 425 | 11.45 | 12.50 |
| ARG 440 | 12.50 | 12.50 |
| ARG 460 | 11.45 | 12.50 |
| ARG 476 | 12.22 | 12.50 |
| ARG 482 | 11.15 | 12.50 |
| ARG 484 | 12.22 | 12.50 |

TABLE 6-continued

Candidate amino acids for substitution in KOD DNA polymerase

| Amino Acid Residue | pKa (calc) | pKa (model) |
|---|---|---|
| ARG 501 | 12.22 | 12.50 |
| ARG 503 | 13.21 | 12.50 |
| ARG 518 | 11.94 | 12.50 |
| ARG 585 | 11.66 | 12.50 |
| ARG 606 | 12.29 | 12.50 |
| ARG 612 | 12.50 | 12.50 |
| ARG 613 | 12.50 | 12.50 |
| ARG 625 | 12.29 | 12.50 |
| ARG 641 | 12.15 | 12.50 |
| ARG 685 | 12.50 | 12.50 |
| ARG 713 | 12.50 | 12.50 |
| ARG 743 | 12.50 | 12.50 |
| ARG 746 | 11.94 | 12.50 |
| ARG 751 | 12.50 | 12.50 |
| ARG 756 | 12.01 | 12.50 |

TABLE 7

Candidate amino acids for modification in B103-type polymerases

| Amino Acid Residue | Substituted Amino Acid | Amino Acid Residue | Substituted Amino Acid |
|---|---|---|---|
| H58 | R | E290 | A |
| H73 | R | E293 | A |
| H74 | R | E311 | A |
| H103 | R | E319 | A |
| H146 | R | E322 | A |
| H153 | R | E331 | A |
| H336 | R | E335 | A |
| H370 | R | E338 | A |
| H458 | R | E343 | A |
| H482 | R | E352 | A |
| E11 | A | | |
| E28 | A | E359 | A |
| E43 | A | E371 | A |
| E50 | A | E405 | A |
| E72 | A | E416 | A |
| E81 | A | E417 | A |
| E148 | A | E463 | A |
| E154 | A | E466 | A |
| E158 | A | E483 | A |
| E159 | A | E505 | A |
| E161 | A | E512 | A |
| E168 | A | E517 | A |
| E216 | A | C7 | S |
| E236 | A | C19 | S |
| E238 | A | C103 | S |
| E241 | A | C445 | S |
| E273 | A | C452 | S |
| E276 | A | C513 | S |
| E288 | A | C527 | S |

What is claimed:

1. A modified Bst DNA polymerase comprising three or more amino acid substitutions selected from the group consisting of H46R, H273R, H281R, E446Q, H473R, Y477F, H528R, and H572R, the numbering of amino acid residues being in accordance with that of SEQ ID NO: 1, wherein the modified polymerase has reduced buffering capacity compared to wild type Bst DNA polymerase, retains the ability to catalyze nucleotide polymerization, and comprises an amino acid sequence having at least 90% identity to the amino acid sequence of SEQ ID NO: 1.

2. The modified Bst DNA polymerase of claim 1, wherein the amino acid substitutions comprise H46R, E446Q, and H572R.

3. The modified Bst DNA polymerase of claim 2, further comprising one or more amino acid substitutions of one or more amino acid residues shown in Table 2 or 3.

4. The modified Bst DNA polymerase of claim 1, wherein the modified polymerase has reduced buffering capacity compared to wild type Bst DNA polymerase within a range of about pH 4 to about pH 10.

5. The modified Bst DNA polymerase of claim 1, wherein the modified polymerase has reduced buffering capacity compared to wild type Bst DNA polymerase within a range of about pH 7 to about pH 9.

6. The modified Bst DNA polymerase of claim 1, wherein polymerase activity of the modified Bst DNA polymerase is at least 90% compared to wild type Bst DNA polymerase.

7. An aqueous solution comprising the modified Bst DNA polymerase of claim 1, wherein said aqueous solution further comprises a template nucleic acid and nucleotides.

8. A method of detecting a nucleotide incorporation, comprising:
   (a) performing a nucleotide incorporation by contacting a template nucleic acid with the modified Bst DNA polymerase of claim 1 in the presence of nucleotides, wherein one or more hydrogen ions are generated as a by-product of the nucleotide incorporation; and
   (b) detecting the one or more hydrogen ions generated as a by-product of the nucleotide incorporation, thereby detecting the nucleotide incorporation.

9. The method of claim 8, wherein the amino acid substitutions comprise H46R, E446Q, and H572R.

10. The method of claim 9, wherein the modified Bst DNA polymerase further comprises one or more amino acid substitutions of one or more amino acid residues shown in Table 2 or 3.

11. The method of claim 8, wherein the modified Bst DNA polymerase has reduced buffering capacity compared to wild type Bst DNA polymerase within a range of about pH 4 to about pH 10.

12. The method of claim 8, wherein the modified Bst DNA polymerase has reduced buffering capacity compared to wild type Bst DNA polymerase within a range of about pH 7 to about pH 9.

13. The method of claim 8, wherein the buffering capacity of the modified Bst DNA polymerase between pH 7 and pH 9 has been removed.

14. A method of sequencing a nucleic acid, comprising:
   (a) contacting a template nucleic acid with the modified Bst DNA polymerase of claim 1 and nucleotides;

(b) synthesizing a new nucleic acid strand by sequentially incorporating one or more of the nucleotides into a nucleic acid molecule; and (c) detecting such incorporation by detecting one or more hydrogen ion byproducts generated when the nucleotide is complementary to a corresponding nucleotide in the template nucleic acid.

15. The method of claim 14, wherein the amino acid substitutions comprise H46R, E446Q, and H572R.

16. The method of claim 15, wherein the modified Bst DNA polymerase further comprises one or more amino acid substitutions of one or more amino acid residues shown in Table 2 or 3.

17. The method of claim 14, wherein the modified Bst DNA polymerase has reduced buffering capacity compared to wild type Bst DNA polymerase within a range of about pH 4 to about pH 10.

18. The method of claim 14, wherein the modified Bst DNA polymerase has reduced buffering capacity compared to wild type Bst DNA polymerase within a range of about pH 7 to about pH 9.

19. The method of claim 14, wherein the buffering capacity of the modified Bst DNA polymerase between pH 7 and pH 9 has been removed.

20. The method of claim 14, wherein the template nucleic acid is hybridized to a sequencing primer when contacting the modified Bst DNA polymerase and synthesizing the new nucleic acid strand by incorporating the one or more nucleotides at the 3' end of the sequencing primer.

* * * * *